US009465038B2

(12) United States Patent
Sarkadi et al.

(10) Patent No.: US 9,465,038 B2
(45) Date of Patent: Oct. 11, 2016

(54) QUANTITATIVE DETERMINATION OF BIOMARKERS IN THE ERYTHROCYTE MEMBRANE

(71) Applicants: Balázs Sarkadi, Budapest (HU); György Várady, Budapest (HU); Ildikó Kasza, Tata (HU)

(72) Inventors: Balázs Sarkadi, Budapest (HU); György Várady, Budapest (HU); Ildikó Kasza, Tata (HU)

(73) Assignee: AdvanCell Diagnosztika Kft., Budapest (HU)

( * ) Notice: Subject to any disclaimer, the term of this patent is extended or adjusted under 35 U.S.C. 154(b) by 0 days.

(21) Appl. No.: 14/395,524

(22) PCT Filed: Apr. 22, 2013

(86) PCT No.: PCT/HU2013/000034
§ 371 (c)(1),
(2) Date: Oct. 20, 2014

(87) PCT Pub. No.: WO2013/156806
PCT Pub. Date: Oct. 24, 2013

(65) Prior Publication Data
US 2015/0111770 A1    Apr. 23, 2015

Related U.S. Application Data

(60) Provisional application No. 61/635,893, filed on Apr. 20, 2012.

(30) Foreign Application Priority Data

Apr. 20, 2012   (HU) .................................. P 1200239

(51) Int. Cl.
C40B 30/04 (2006.01)
G01N 33/68 (2006.01)
G01N 33/80 (2006.01)
G01N 21/64 (2006.01)
G01N 15/14 (2006.01)
G01N 15/10 (2006.01)

(52) U.S. Cl.
CPC .......... *G01N 33/6872* (2013.01); *G01N 21/64* (2013.01); *G01N 33/6893* (2013.01); *G01N 33/80* (2013.01); *G01N 15/1459* (2013.01); *G01N 2015/1006* (2013.01); *G01N 2015/1488* (2013.01); *G01N 2333/705* (2013.01); *G01N 2333/70596* (2013.01)

(58) Field of Classification Search
None
See application file for complete search history.

(56) References Cited

U.S. PATENT DOCUMENTS 4,731,238 A * 3/1988 Neville .................. C07K 16/30
                                                        424/140.1
5,691,157 A    11/1997 Gong et al.
2007/0274919 A1  11/2007 Dertinger
2011/0020849 A1   1/2011 Spence

FOREIGN PATENT DOCUMENTS

EP   1 174 498 A2   1/2002
EP   1 378 519 A1   1/2004
WO   95/08116 A1    3/1995
WO   01/16326 A2    3/2001

OTHER PUBLICATIONS

Antonelou et al.: "Apolipoprotein J/Clusterin Is a Novel Structural Component of Human Erythrocytes and a Biomarker of Cellular Stress and Senescence", PLoS One, 2011, vol. 6, Issue 10, e26032.
Bozdech et al.: "The human malaria parasite Plasmodium falciparum exports the ATP-binding cassette protein PFGCN20 to membrane structures in the host red blood cell", Molecular and Biochemical Parasitology, 1998, vol. 97, pp. 81-95.
De,ák et al.: "HbA1c levels and erythrocyte transport functions in complication-free type 1 diabetic children and adolescents", Acta Diabetol, 2003, vol. 40, pp. 9-13.
Fukuda et al: "Deficiency of complement decay-accelerating factor (DAF, CD55) in non-Hodgkin's lymphoma", Immunology Letters, 1991, vol. 29, pp. 205-210.
Ghinassi et al.: "Comparative Blood Group Profiling of Human Erythroid Cells (EBs) Generated from Adult Blood (AB), Cord Blood (CB), Human Embryonic Stem Cells (hESC) and Induced Pluripotent Stem Cells (iPS)", 53rd ASH Annual Meeting and Exposition, 2011, Oral Abstracts and Poster, San Diego, USA.
Goodman et al.: "The Human Red Blood Cell Proteome and Interactome", Experimental Biology and Medicine, 2007, vol. 232, pp. 1391-1408.
Hernández-Hernández et al.: "Alterations in erythrocyte membrane protein composition in advanced non-small cell lung cancer", Blood Cells, Molecules & Diseases, 2006, vol. 36, pp. 355-363.
Kasza et al.: "Expression Levels of the ABCG2 Multidrug Transporter in Human Erythrocytes Correspond to Pharmacologically Relevant Genetic Variations", PLOS One, Nov. 2012, vol. 7, issue 11, e48423.
Koren et al.: "Enhanced erythrocyte Na+/H+ exchange predicts diabetic nephropathy in patients with IDDM", Diabetologia, 1998, vol. 41, pp. 201-205.

(Continued)

*Primary Examiner* — Catherine S Hibbert
(74) *Attorney, Agent, or Firm* — Jason D. Voight

(57) ABSTRACT

This invention relates to determination of quantitative expression of plasma membrane proteins as biomarkers in the erythrocytes. The invention includes simple, quantitative assay platforms which can be made available in most diagnostic laboratories. The platform allows performing personalized, quantitative tests for the direct expression level of a wide range of membrane proteins from small volume blood samples and connecting them to individual genetic variability, disease conditions, disease stages and complications, treatment protocols, pharmacological responses, or toxic side effects.

12 Claims, 43 Drawing Sheets

(56) References Cited

OTHER PUBLICATIONS

Mackintosh et al.: "Acquisition of naturally occurring antibody responses to recombinant protein domains of Plasmodium falciparum erythrocyte membrane protein I", Malaria Journal, 2008, 7:155.

Pasini et al.: "Red blood cell (RBC) membrane proteomics—Part I: Proteomics and RBC physiology", Journal of Proteomics, 2010, vol. 73, pp. 403-420.

Saison et al.: "Null alleles of ABCG2 encoding the breast cancer resistance protein define the new blood group system Junior" (including Supplementary Figures 1-5, Supplementary Tables 1-2), Nature Genetics, 2012, vol. 44, No. 2, pp. 174-177.

Sharma et al.: "RLIP76 Is the Major ATP-Dependent Transporter of Glutathione-Conjugates and Doxorubicin in Human Erythrocytes", Archives of Biochemistry and Biophysics, 2001, vol. 391, No. 2, pp. 171-179.

Smolarek et al.: "A recombinant dromedary antibody fragment (VHH or nanobody) directed against human Duffy antigen receptor for chemokines", Cell. Mol. Life Sci., 2010, vol. 67, pp. 3371-3387.

Sprague et al.: "Reduced Expression of Gi in Erythrocytes of Humans With Type 2 Diabetes Is Associated With Impairment of Both cAMP Generation and ATP Release", Diabetes, 2006, vol. 55, pp. 3588-3593.

Weder et al.: "Erythrocyte Sodium-Lithium Countertransport and Blood Pressure, A Genome-Wide Linkage Study", Hypertension, 2003, vol. 41 [part 2], pp. 842-846.

Várady et al.: "Cell surface membrane proteins as personalized biomarkers: where we stand and where we are headed", Biomarkers Med., Oct. 2013, vol. 7(5), pp. 803-819.

* cited by examiner

ABCG2(5D3)+
GAM-PE(IgG2b)

Glycophorin-A-
FITC

Figure 2A. ABCG2 is differentially expressed in the red blood cells of individuals carrying wild-type, polymorphyic or mutant *ABCG2* alleles
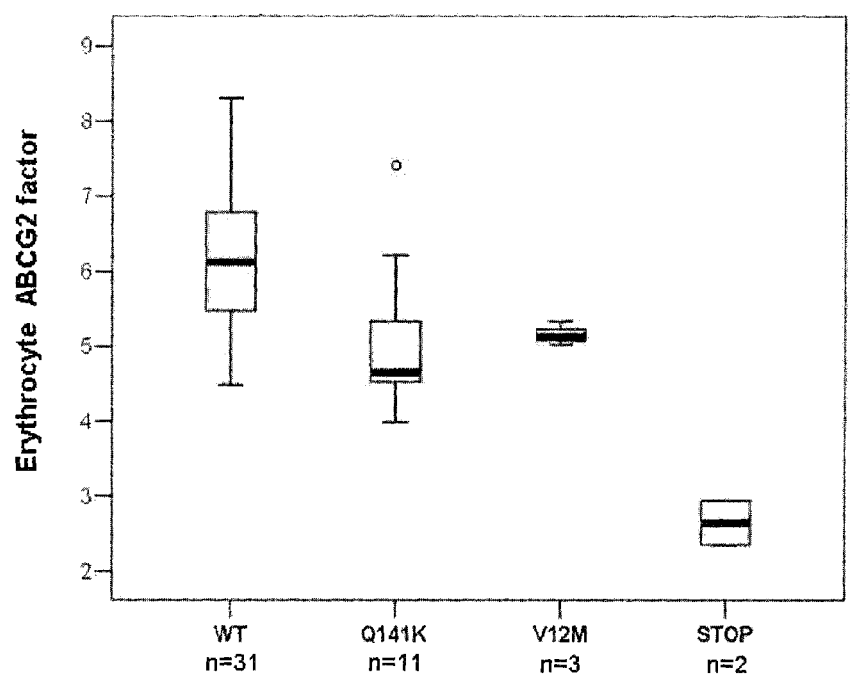

Figure 2B. Pedigrees of two families carrying different ABCG2 premature stop mutations – co-segragation of the heterozygous mutation with reduced erythrocytic ABCG2 expression levels.
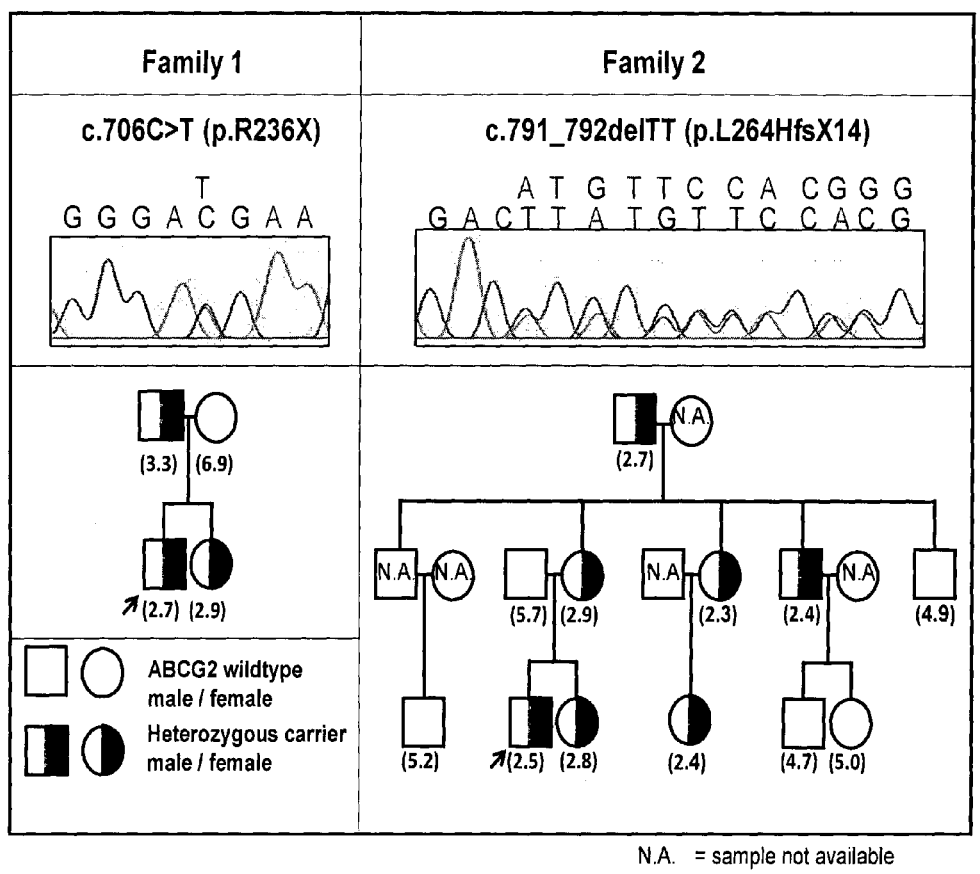
N.A. = sample not available Figure 3. Western blot examination of the human ABCG2 protein in human red cells, ABCG2 heterologously expressed in Sf9 insect cells and ABCG2 expressed in human K652 tumor cells.
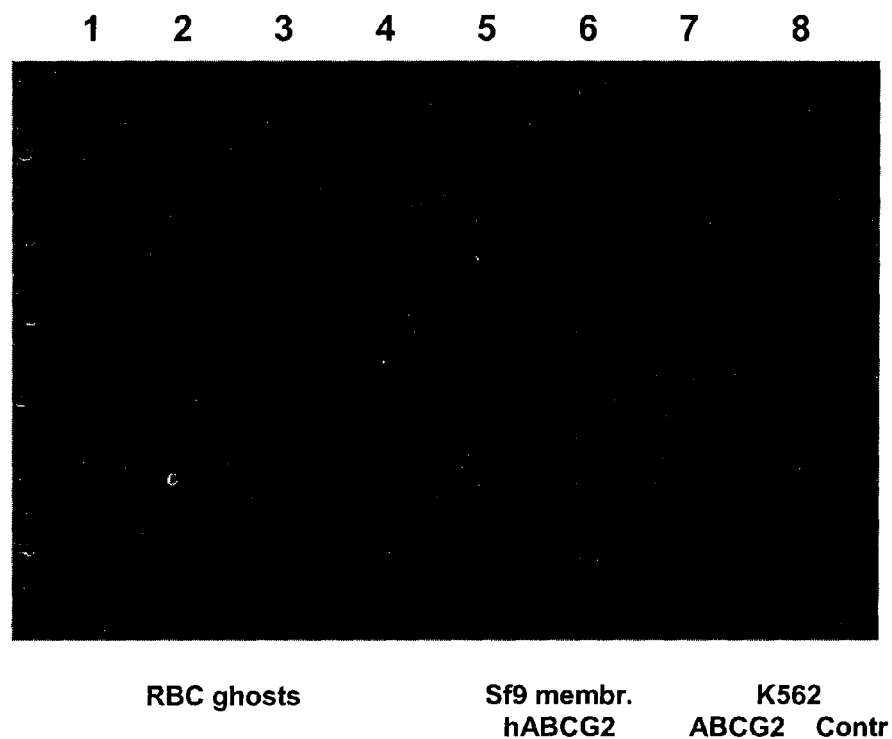

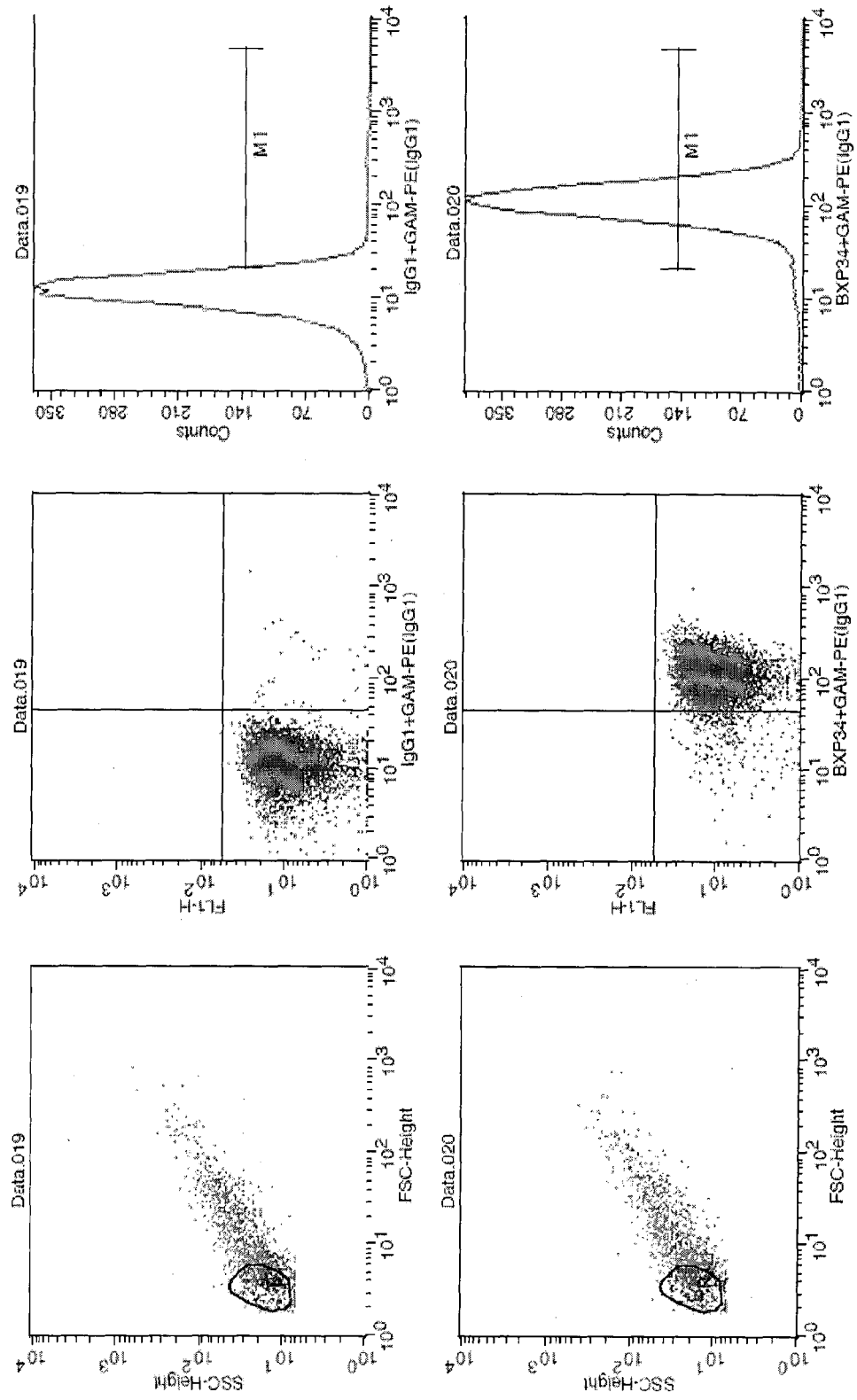
Figure 6. Determination of the erythrocyte membrane ABCG2 expression level in frozen-thawed blood samples.
Figure 6A peripheral blood samples – frozen stored and thawed erythrocytes. Determination of ABCG2 expression by using specific monoclonal antibodies. SSC/FSC view, control IgG and BXP34 binding to frozen stored human red cells.

Figure 6B Detection of the ABCG2 protein by using 3 monoclonal antibodies
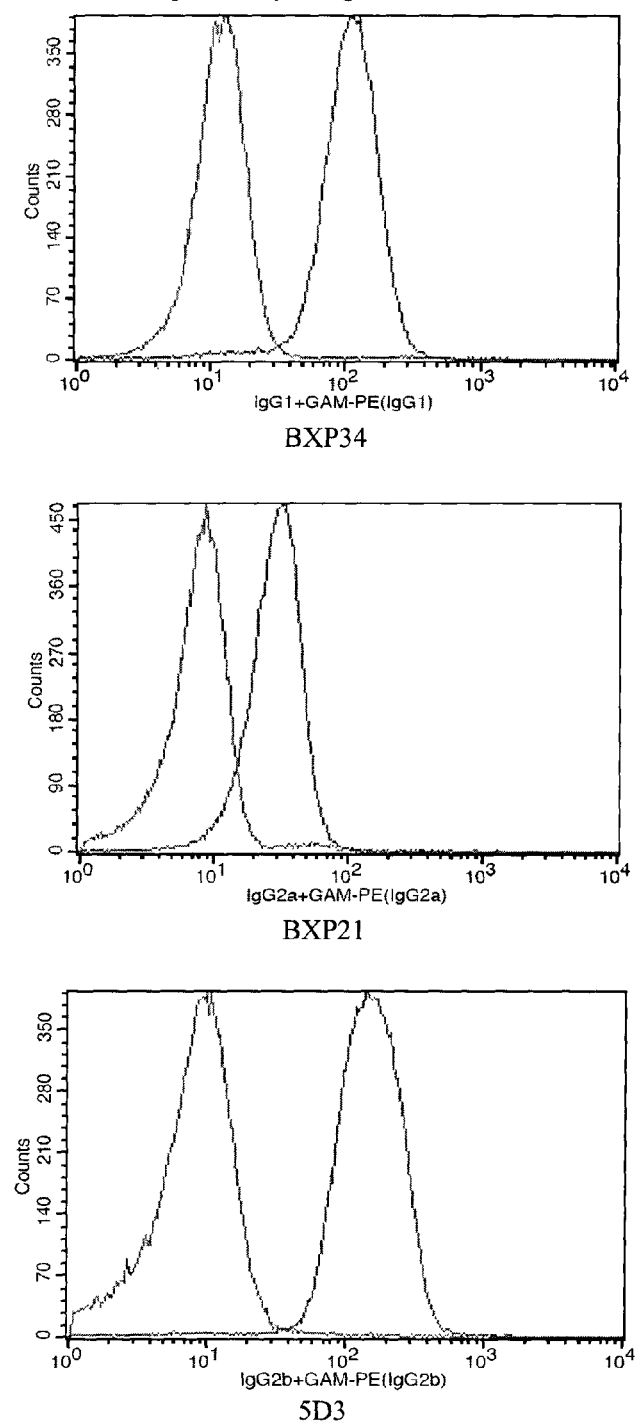

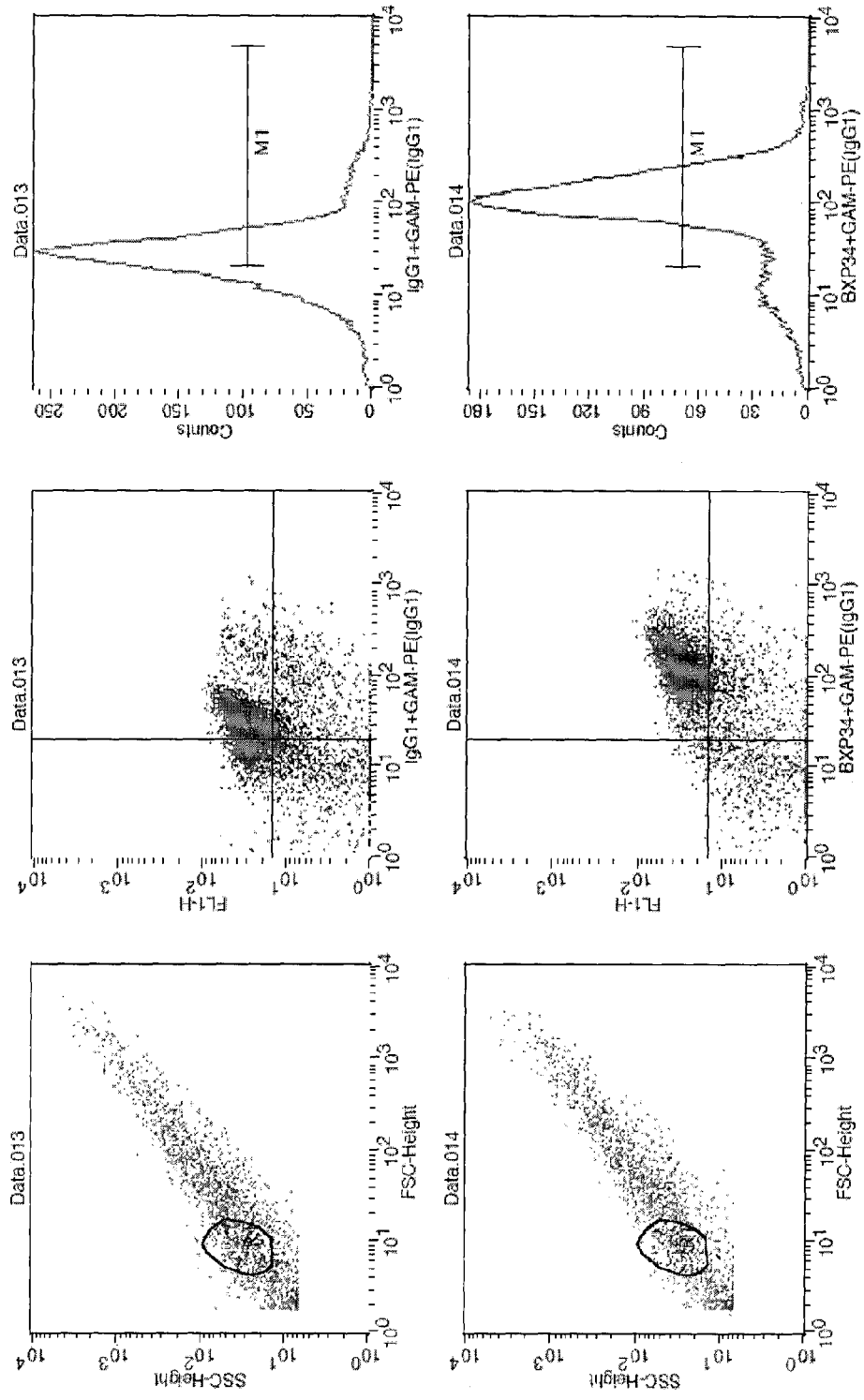
Figure 7. Determination of the erythrocyte membrane ABCG2 expression level in frozen-thawed bone marrow aspirate samples. Application of three different anti-ABCG2 monoclonal antibodies.
Figure 7A Bone marrow aspirate samples –SSC/FSC view, control IgG and BXP34 binding to frozen stored human red cells.

Figure 7B Detection of the ABCG2 protein by using 3 monoclonal antibodies
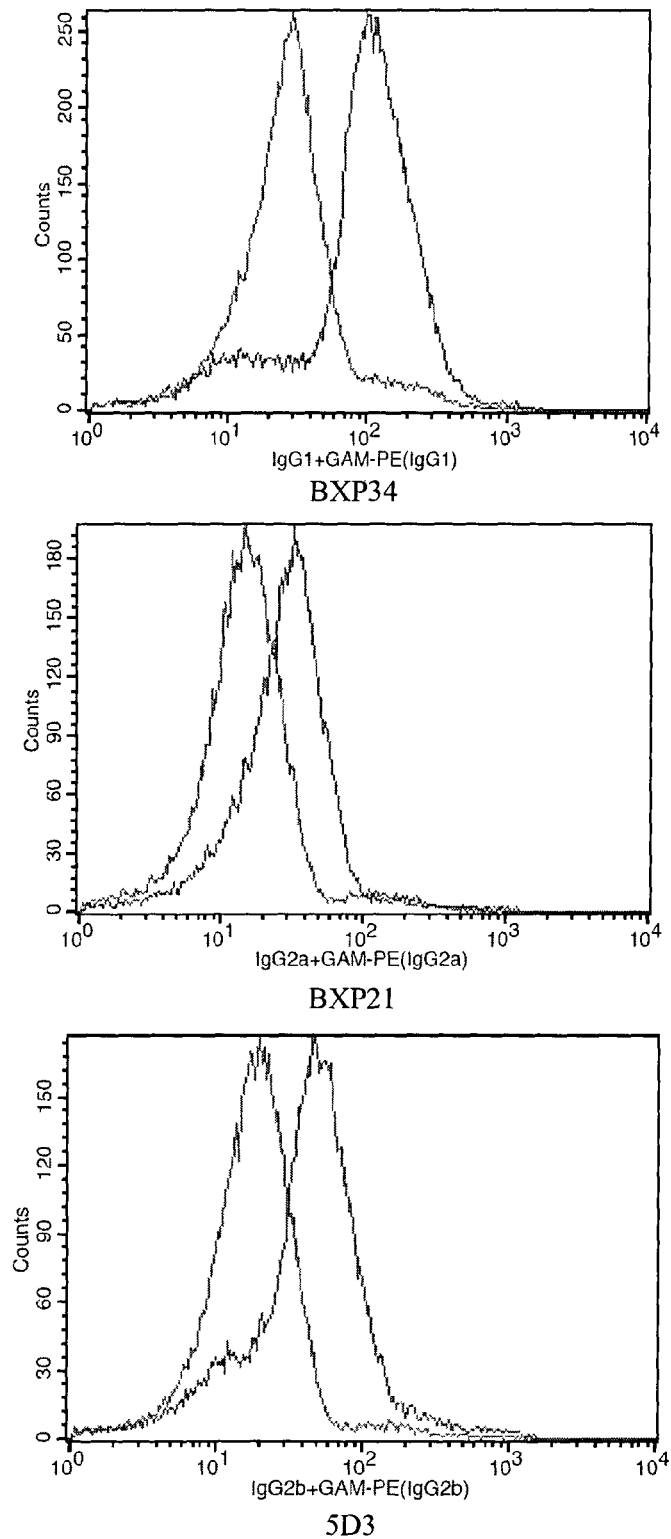

Figure 8. Quantitative determination of erythrocyte membrane ABCG2 expression in frozen-thawed blood samples.

Figure 9. Quantitative determination of erythrocyte membrane ABCG2 expression in microplates.
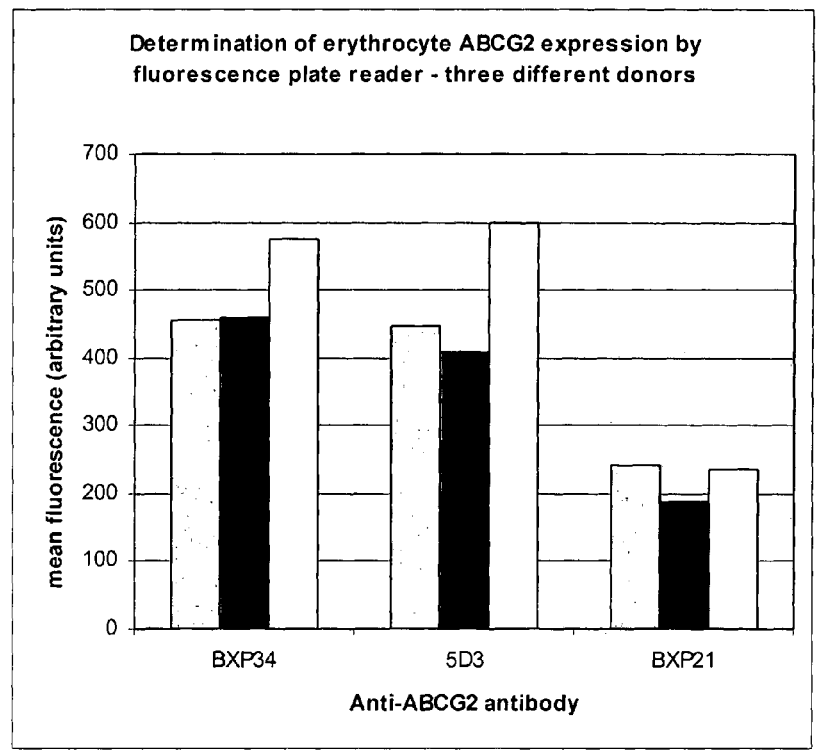

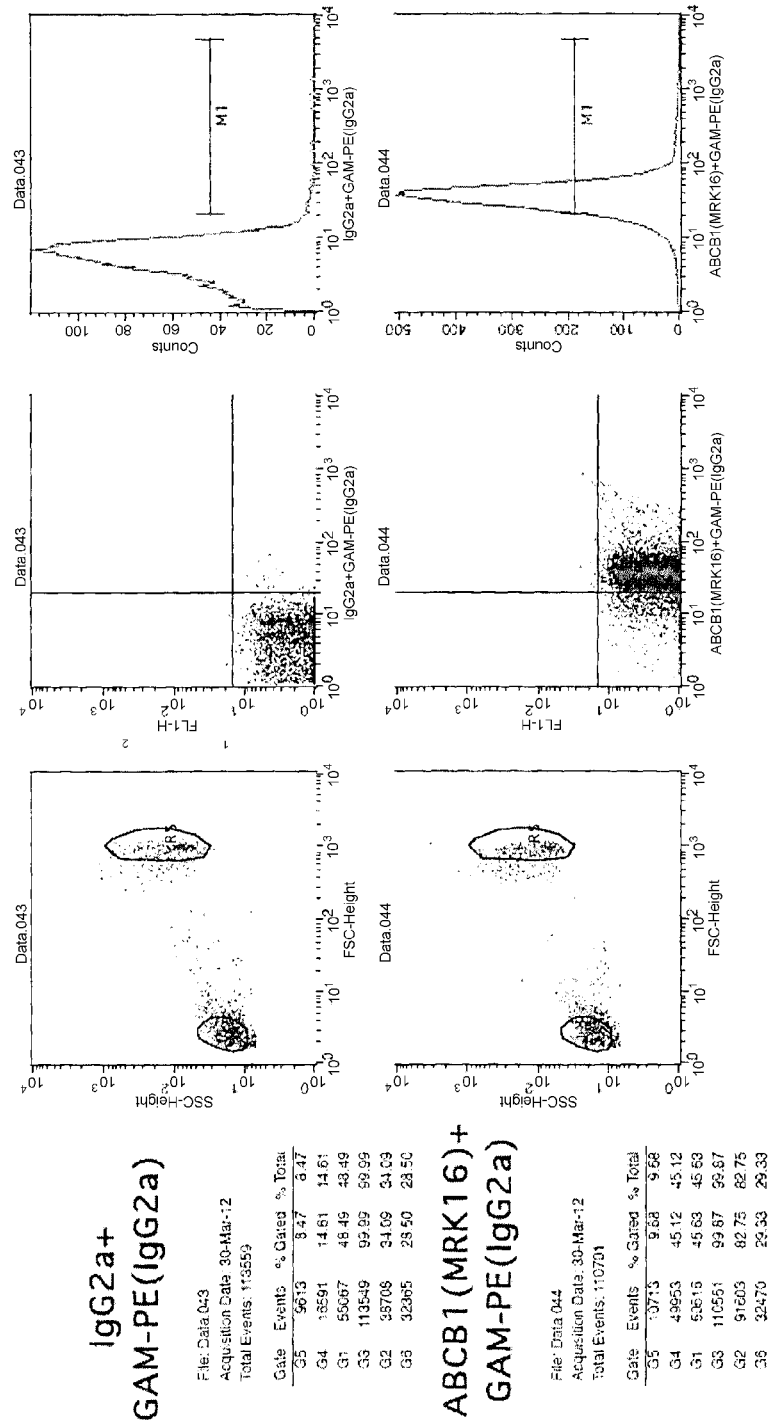
Figure 10A. Detection of ABCB1 in human red cells by a specific monoclonal antibody MRK16.

Figure 10B. Detection of ABCB1 in human rec cells by a specific monoclonal antibody MRK16.
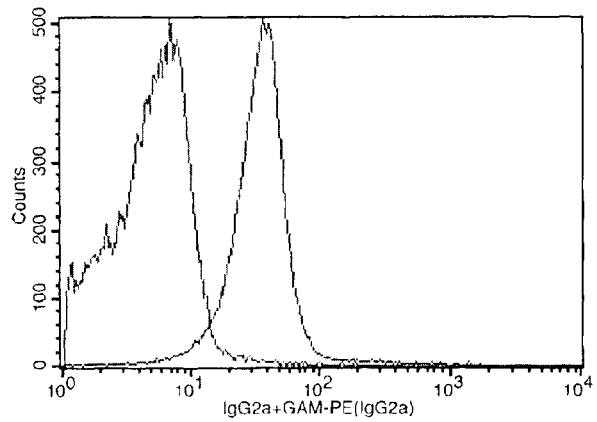
Figure 11. Detection of ABCB1 in human red cells by two ABCB1 specific monoclonal antibodies.
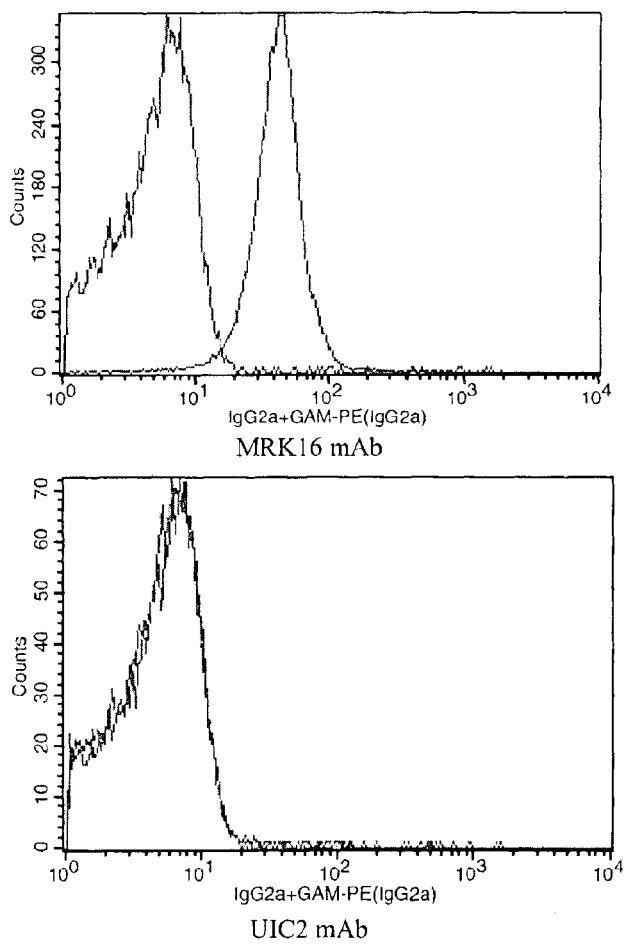
MRK16 mAb
UIC2 mAb Figure 12. Detection of ABCB1 in human red cells by two ABCB1 specific monoclonal antibodies:
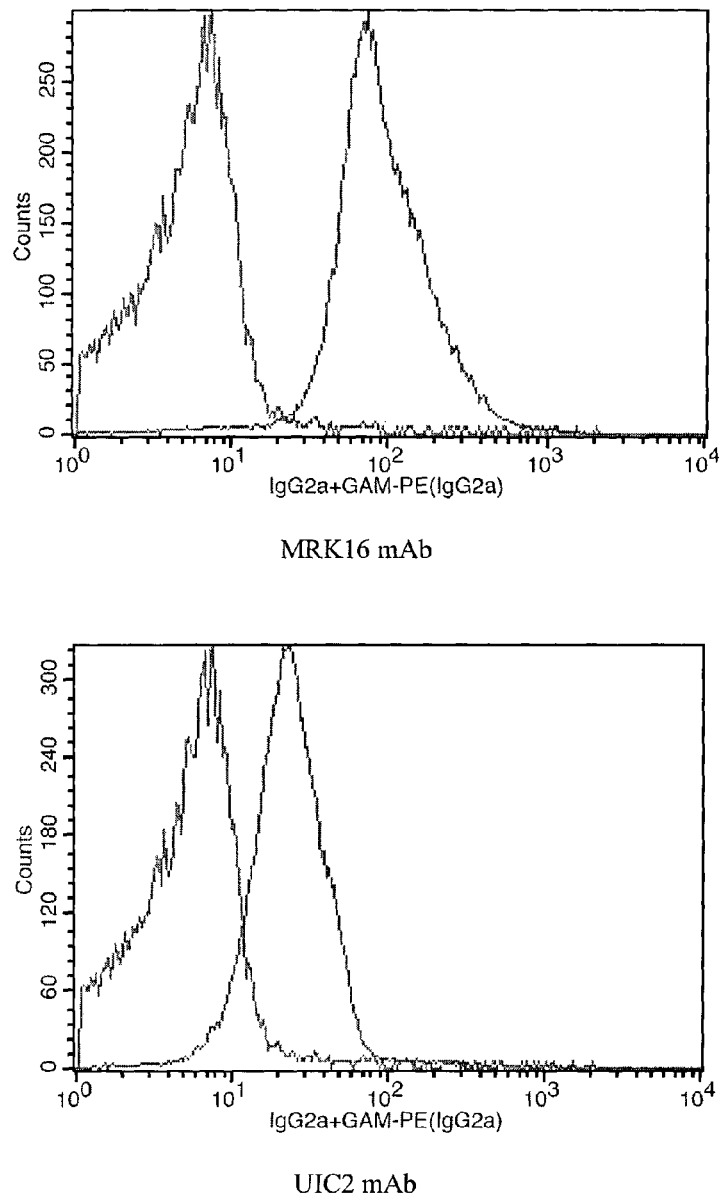

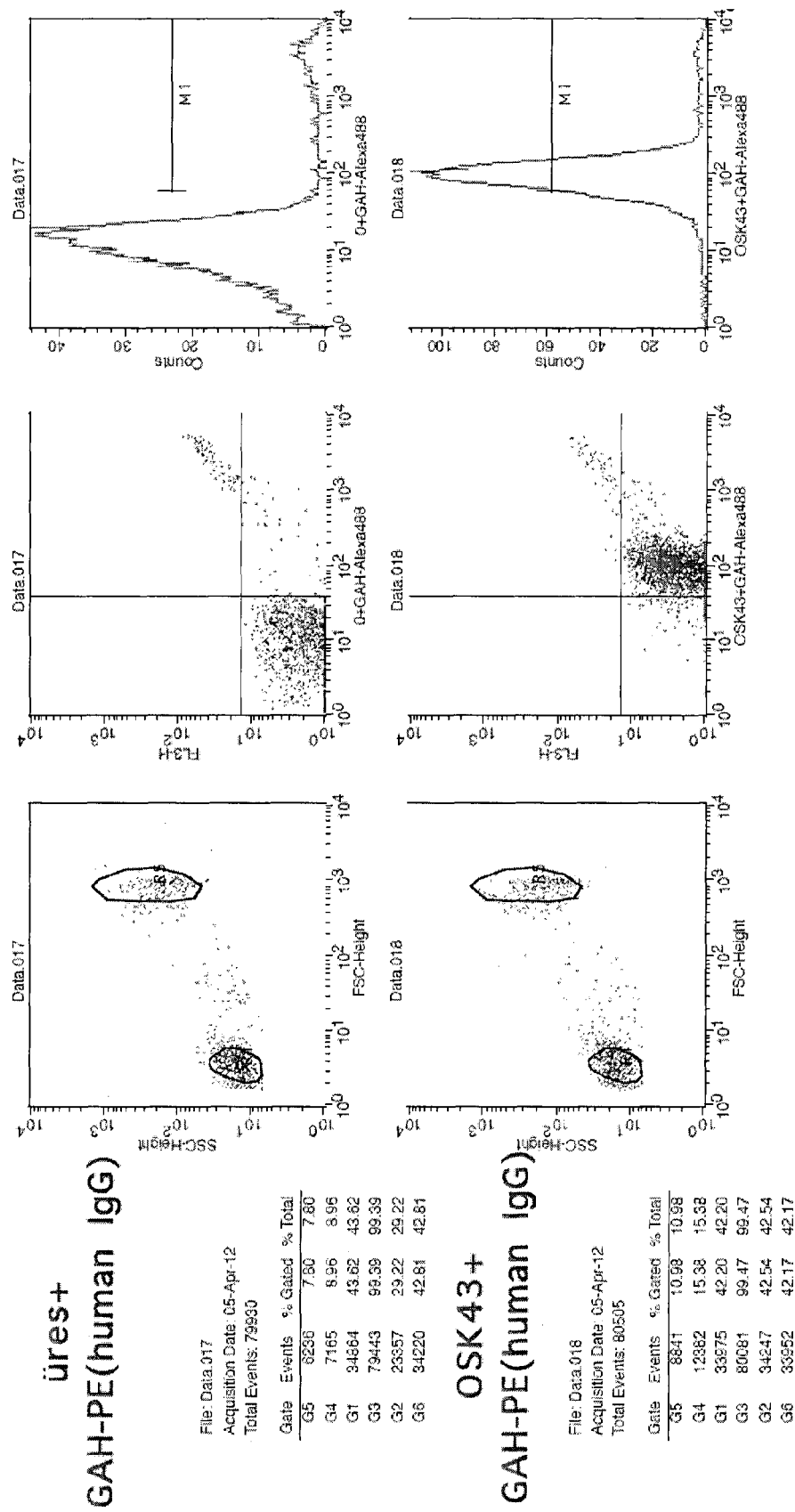
Figure 13A_1 Detection of ABCB6 in human red cells by a monoclonal antibody reacting with a cell-surface epitope of human ABCB6 (freshly drawn blood cells fixed in 1% PFA)

Figure 13A_2 Detection of ABCB6 in human red cells by a monoclonal antibody reacting with a cell-surface epitope of human ABCB6 (freshly drawn blood cells fixed in 1% PFA)
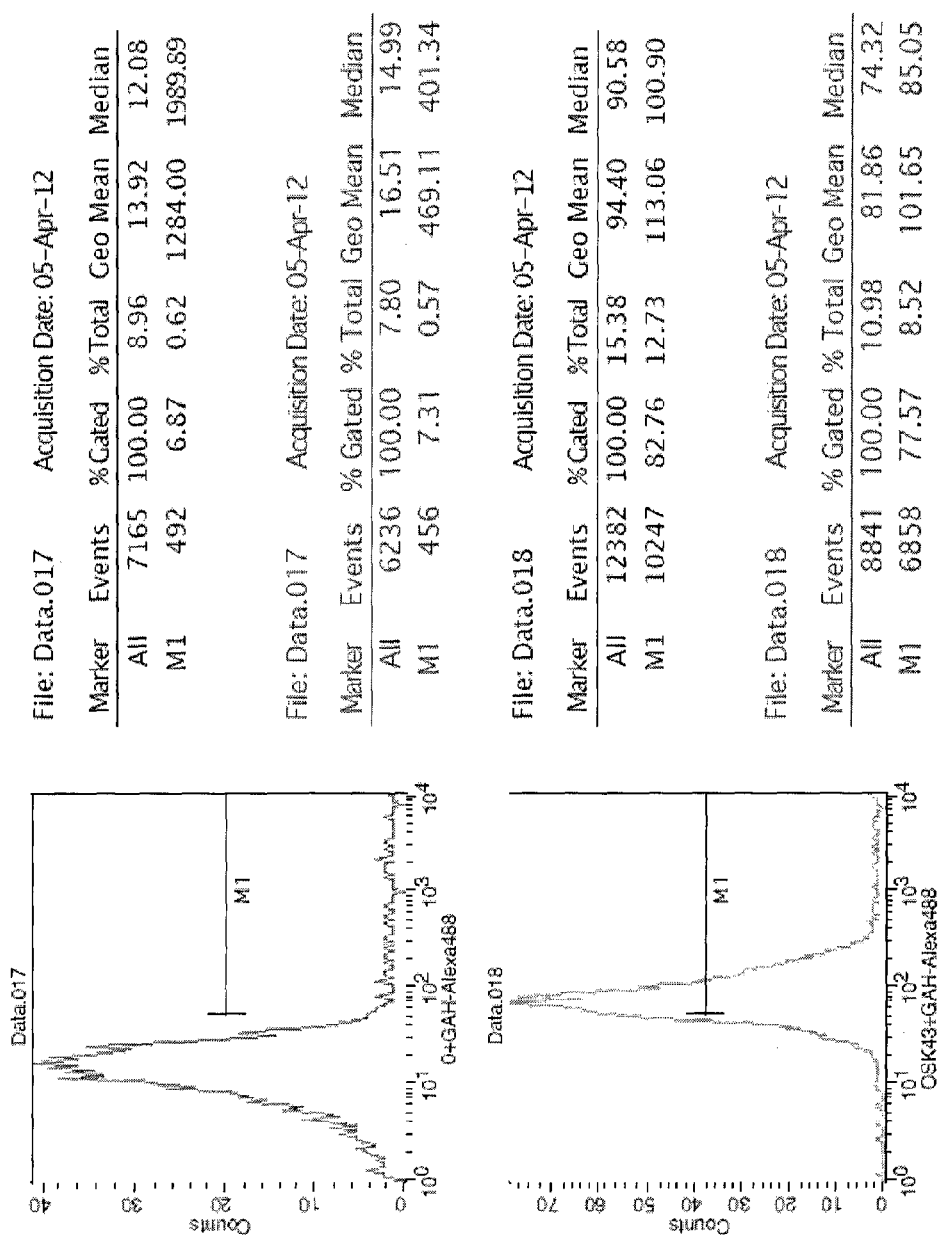

Figure 13A_3 Detection of ABCB6 in human red cells by a monoclonal antibody reacting with a cell-surface epitope of human ABCB6 (freshly drawn blood cells fixed in 1% PFA)
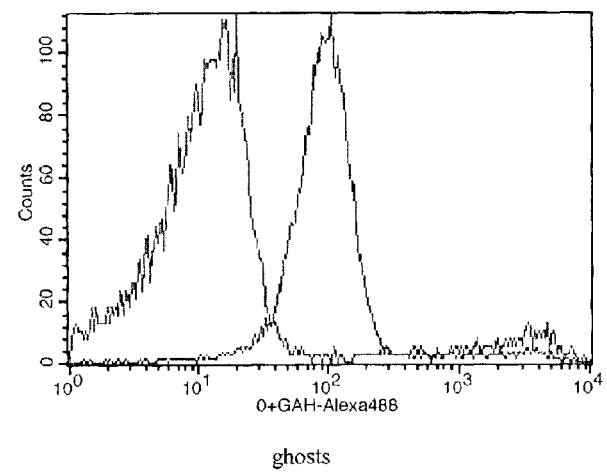
ghosts
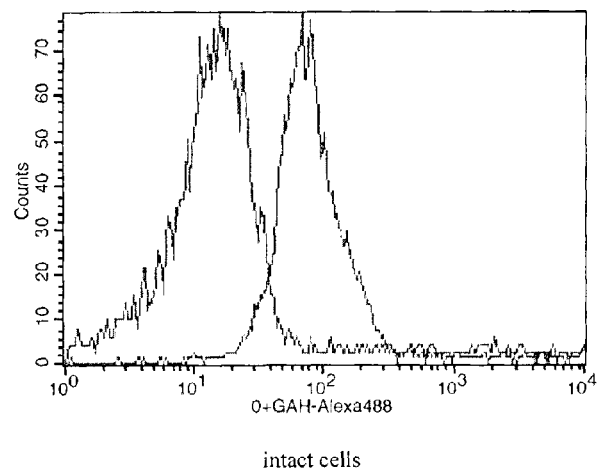
intact cells Figure 13B: Quantitative determination of erythrocyte membrane ABCB6 expression in blood samples of individuals carrying wild-type or mutant ABCB6 alleles
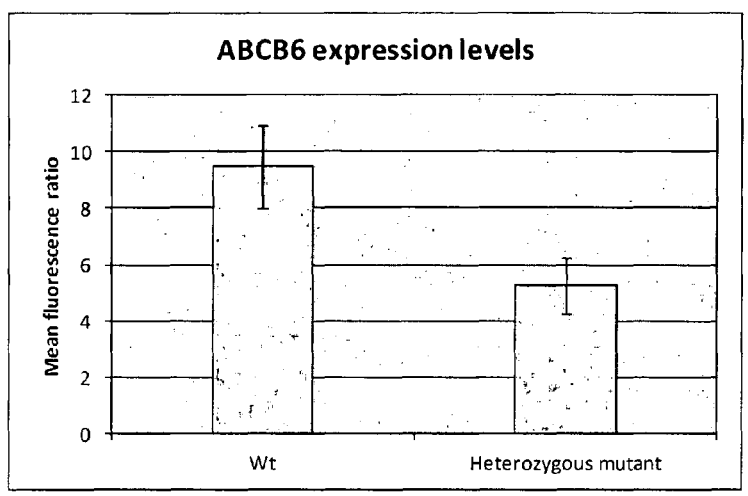
Figure 13C: Pedigree of a family carrying ABCB6 mutations – co-segregation of the mutations with reduced erythrocytic ABCB6 expression levels
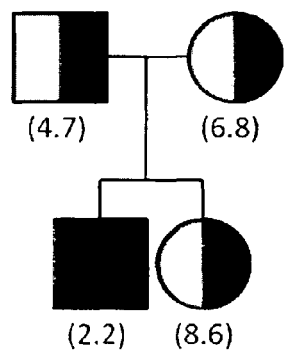

Total Events: 200000

| Marker | Events | %Gated | %Total | GeoMean | Median |
|---|---|---|---|---|---|
| All | 63334 | 100.00 | 31.67 | 9.33 | 9.82 |
| M1 | 459 | 0.72 | 0.23 | 54.86 | 40.68 |

Total Events: 200000

| Marker | Events | %Gated | %Total | GeoMean | Median |
|---|---|---|---|---|---|
| All | 138538 | 100.00 | 69.27 | 32.76 | 34.91 |
| M1 | 81090 | 58.53 | 40.54 | 48.03 | 44.91 |

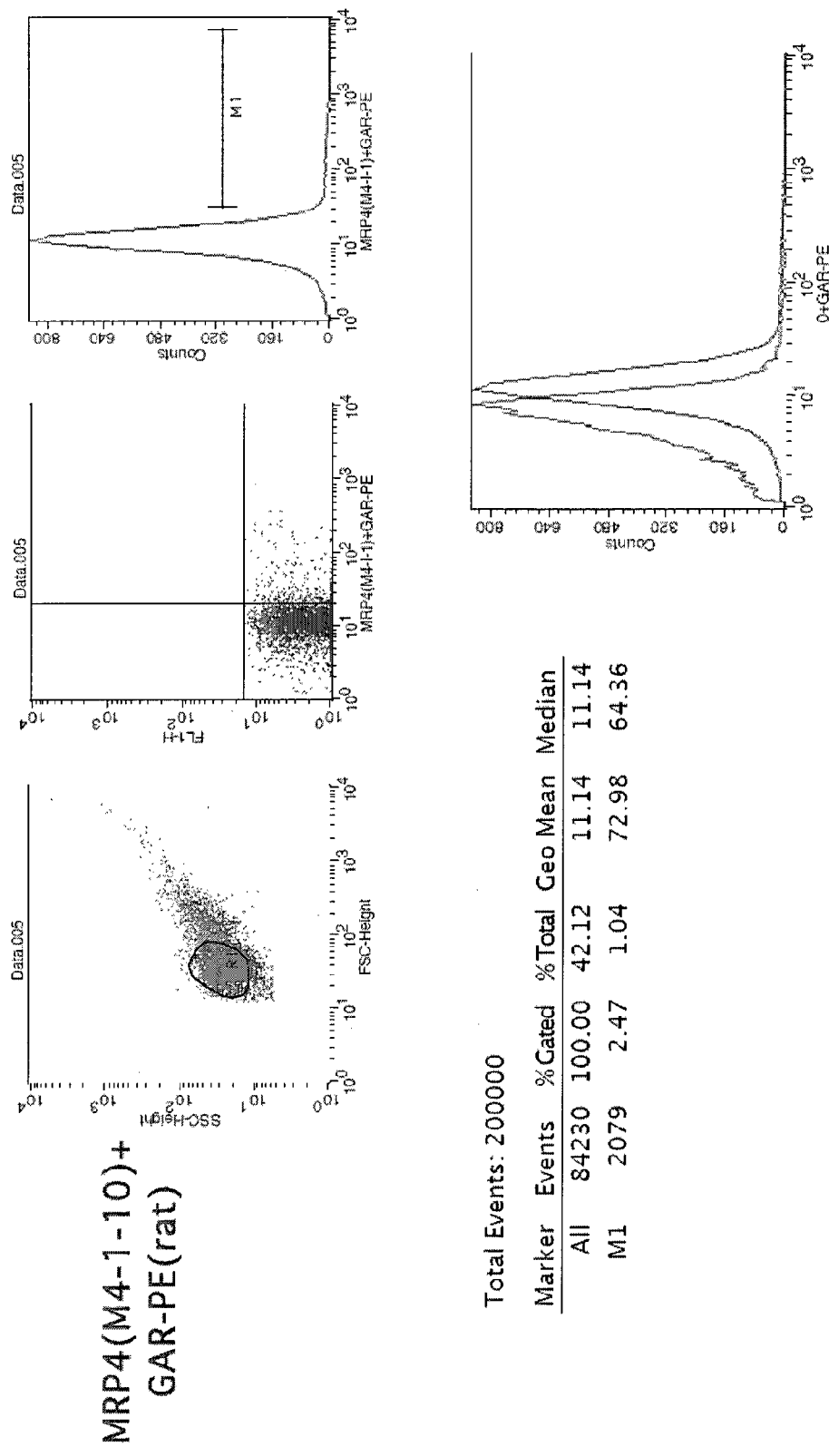
Figure 15. Detection of ABCC4 in human red cells by a mouse monoclonal antibody (M4-1-10) reacting with an intracellular epitope of the human ABCC1 protein (freshly drawn blood cells, unfixed membranes).

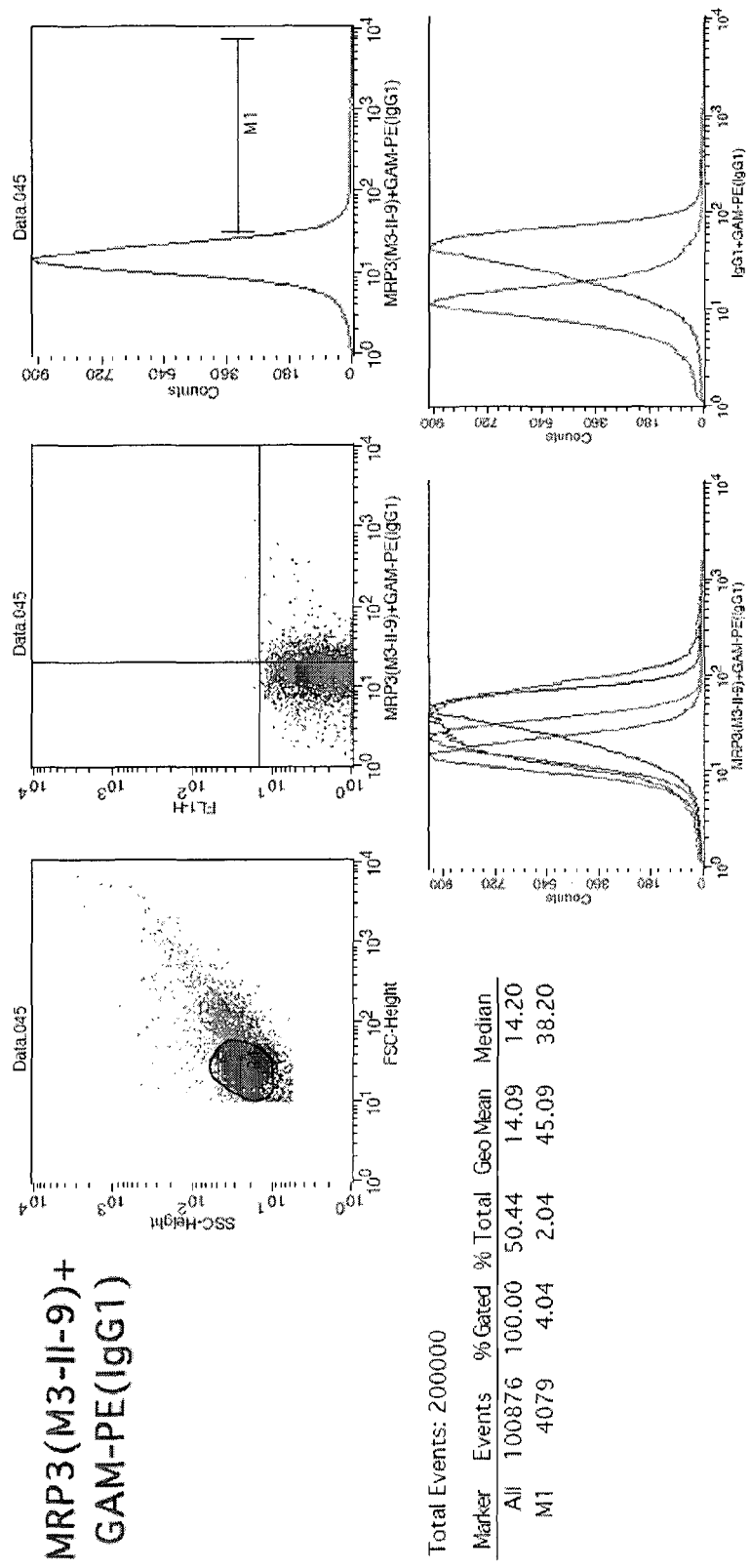
Figure 17. Detection of ABCC3 protein in human red cells by a monoclonal antibody M3-II-9, reacting with an intracellular epitope of the human ABCC3 protein (freshly drawn blood cells fixed in 1% PFA).

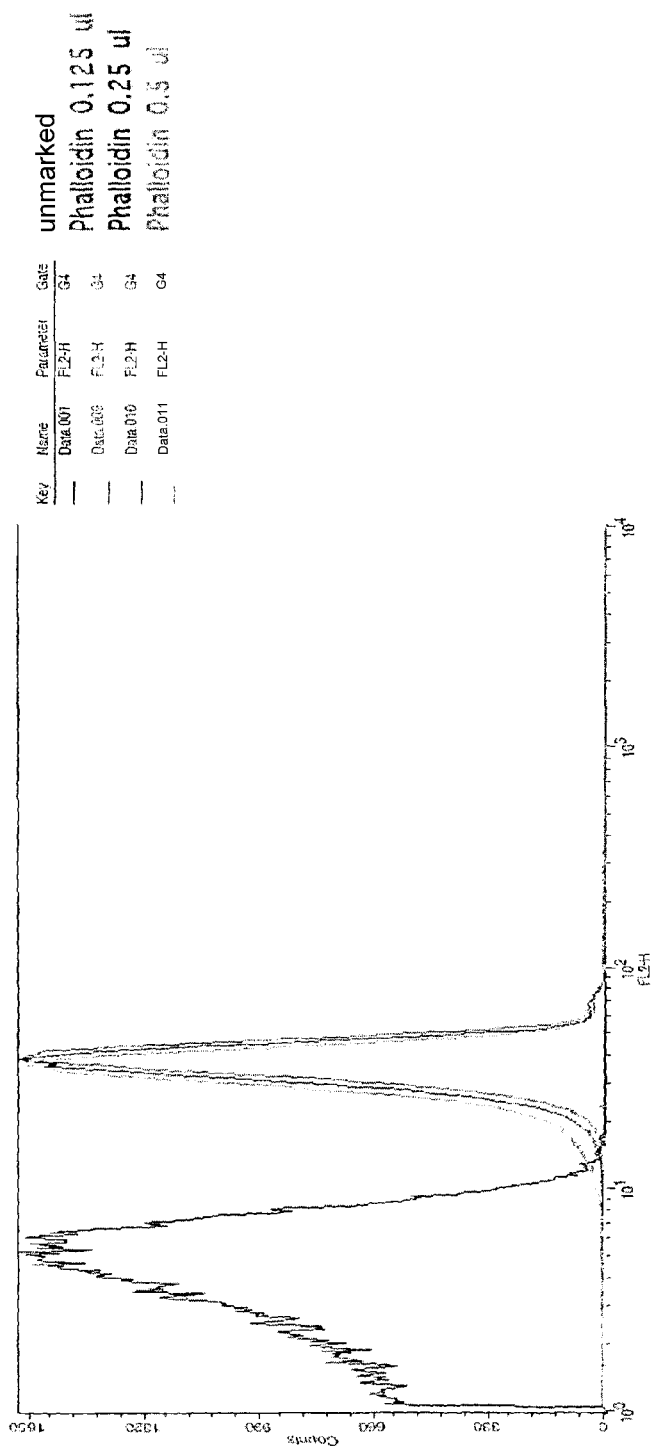
Figure 18A. Ghost fraction

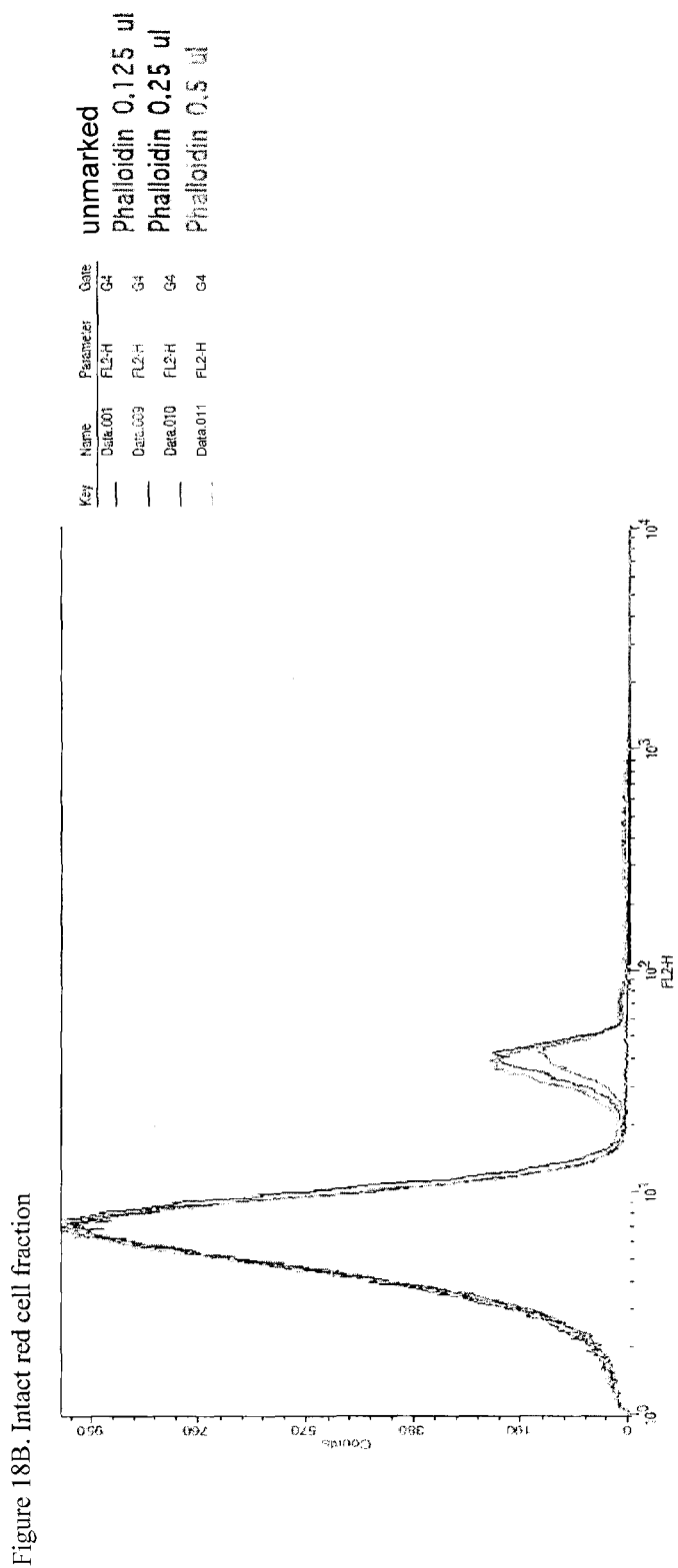
Figure 18B. Intact red cell fraction

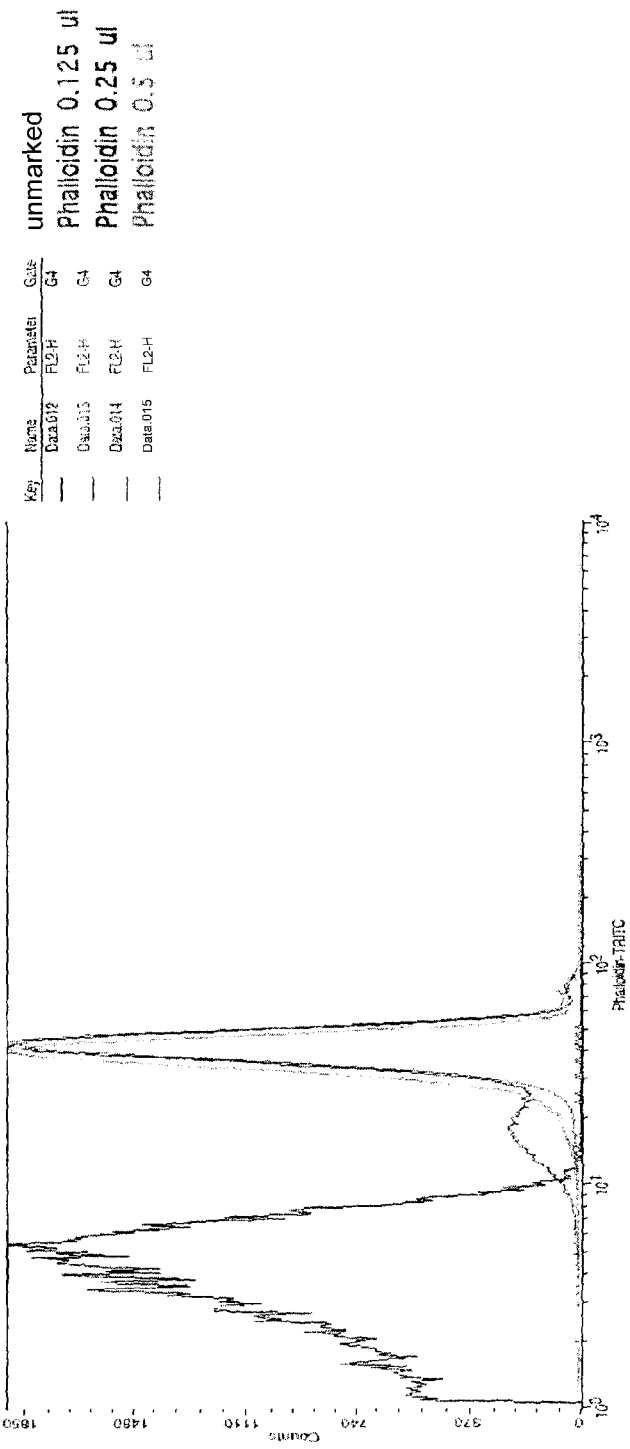
Figure 18C. Saponin permeabilized red cells

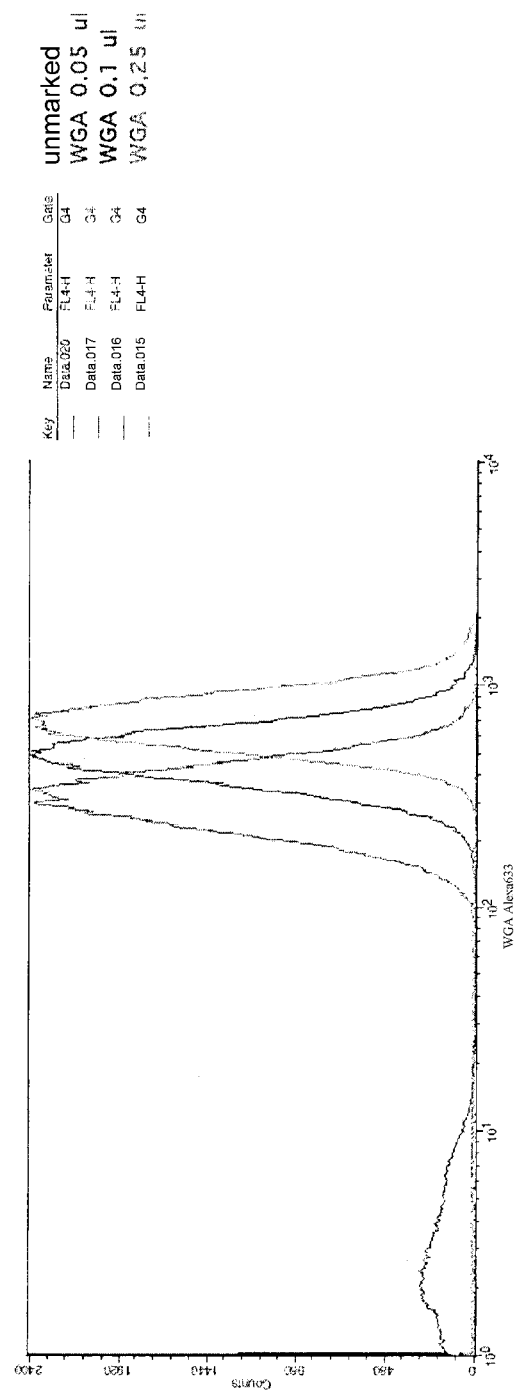
Figure 19A. Ghost fraction

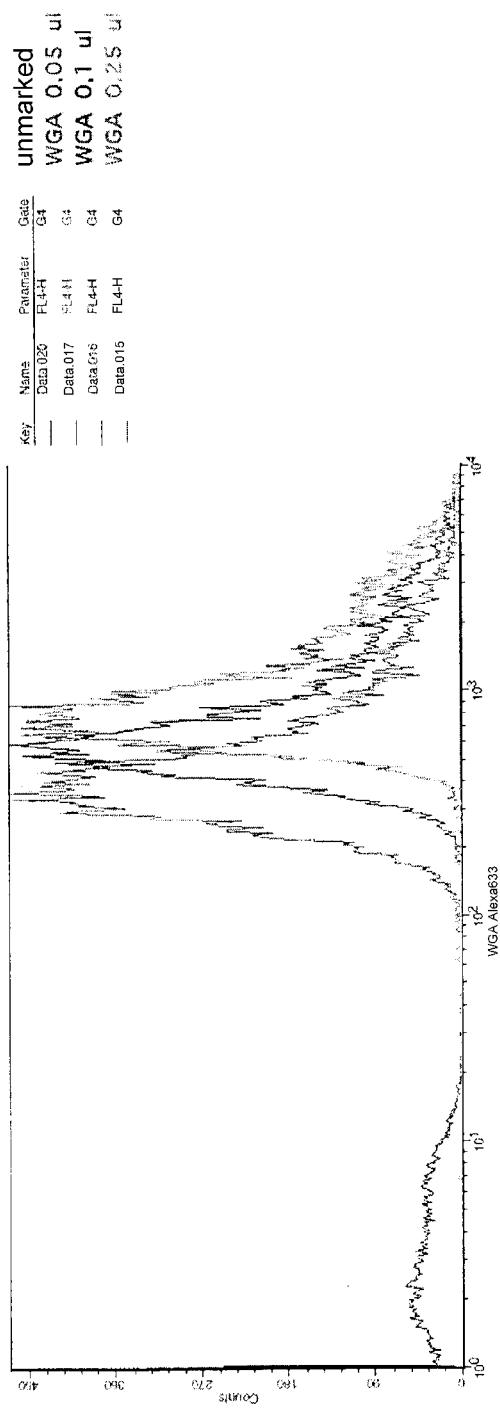
Figure 19B. Intact red cell fraction

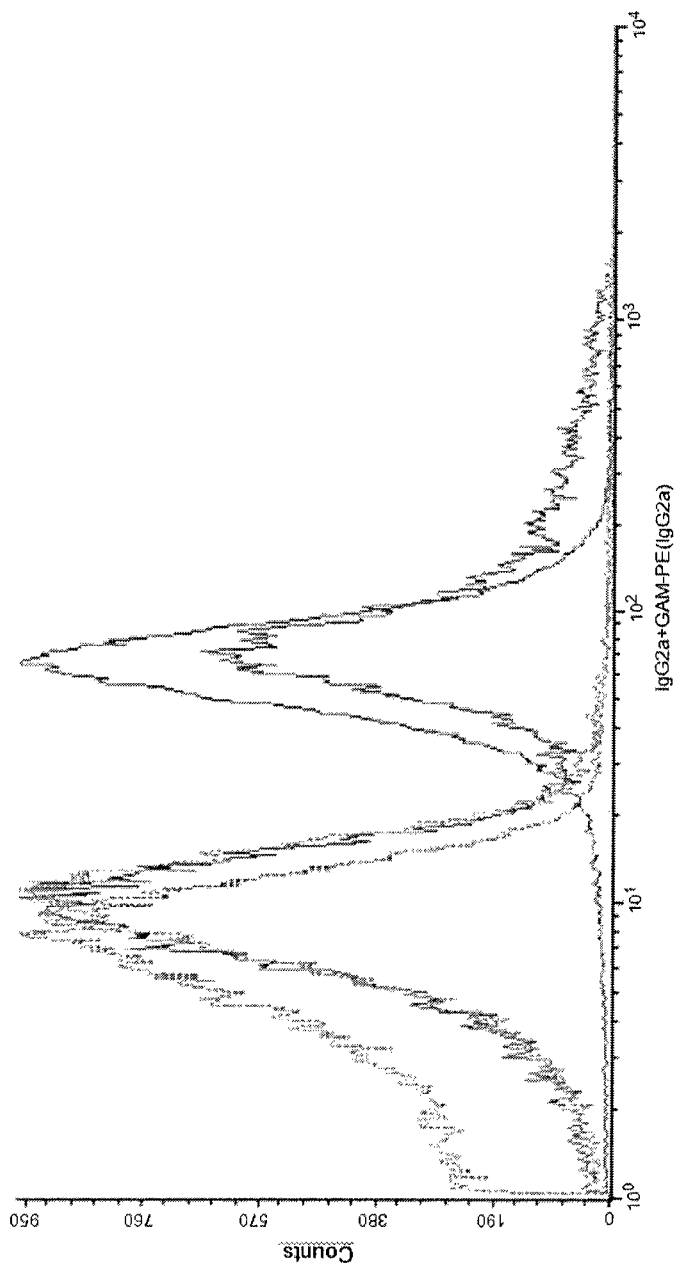
Figure 20. Recognition of the PMCA protein in fixed human RBCs by the 5F10 monoclonal antibody recognizing all PMCA isoforms.

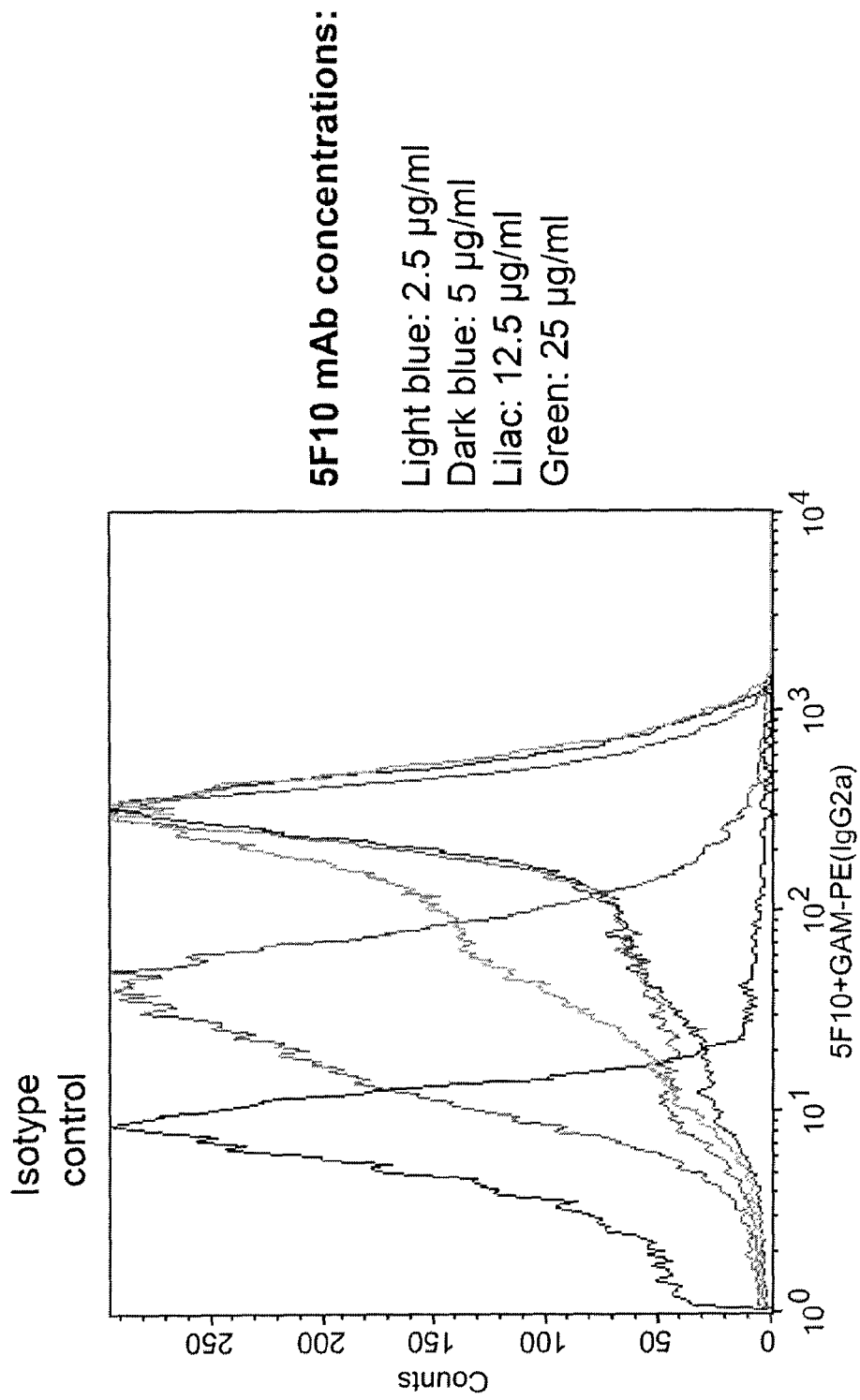
Figure 21. Calibration of 5F10 antibody binding and saturation. Human RBC were fixed and the PMCA protein was quantitated in the ghost fraction by the 5F10 monoclonal antibody, recognizing all PMCA isoforms.

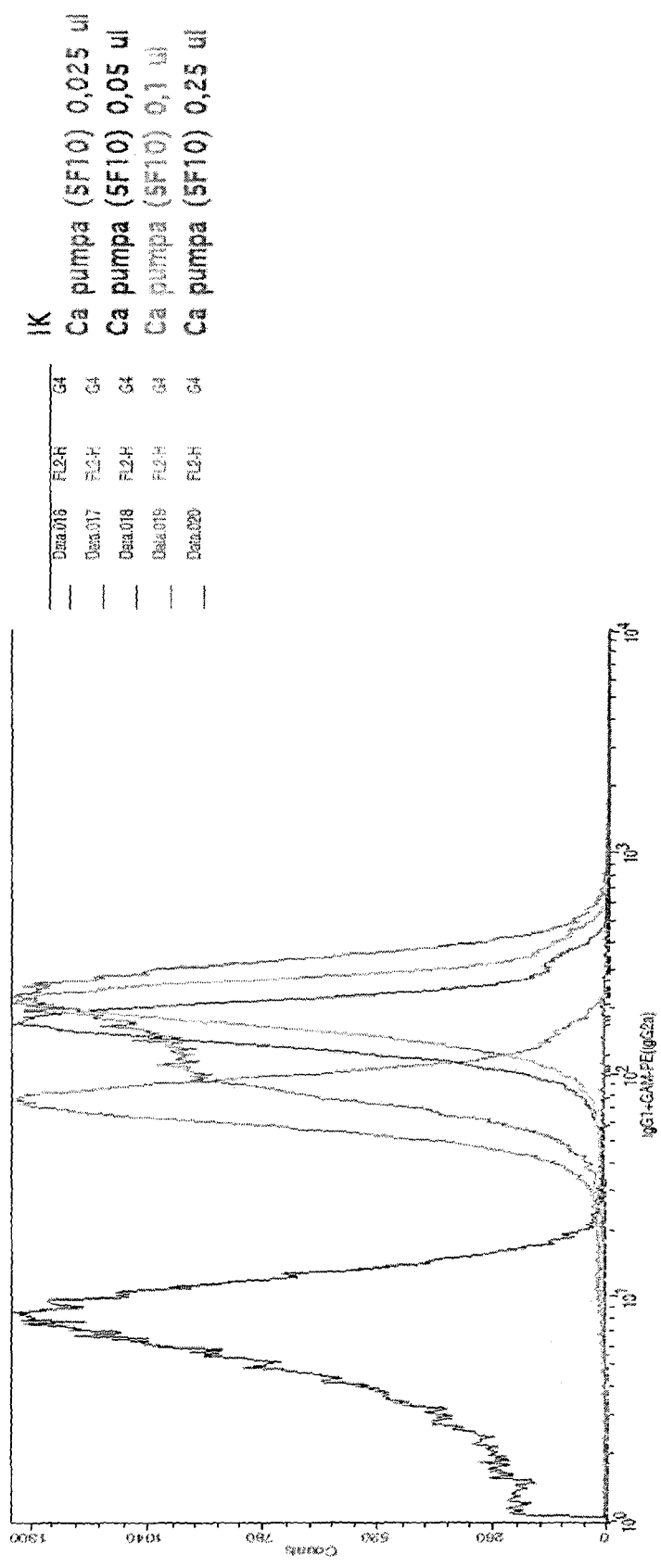
Figure 22. Calibration of 5F10 antibody binding and saturation. Human RBC were fixed and saponin permeabilized (see methods).

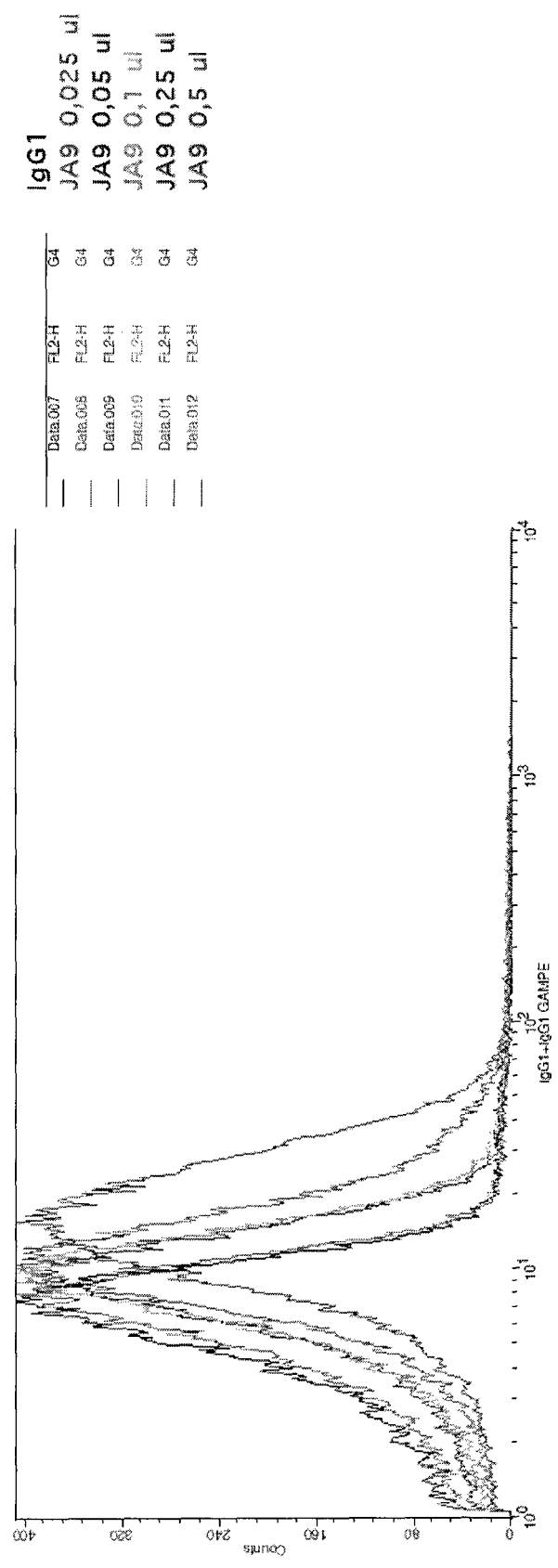
Figure 23. Recognition of the PMCA4 protein in fixed human RBCs by the JA9 monoclonal antibody.

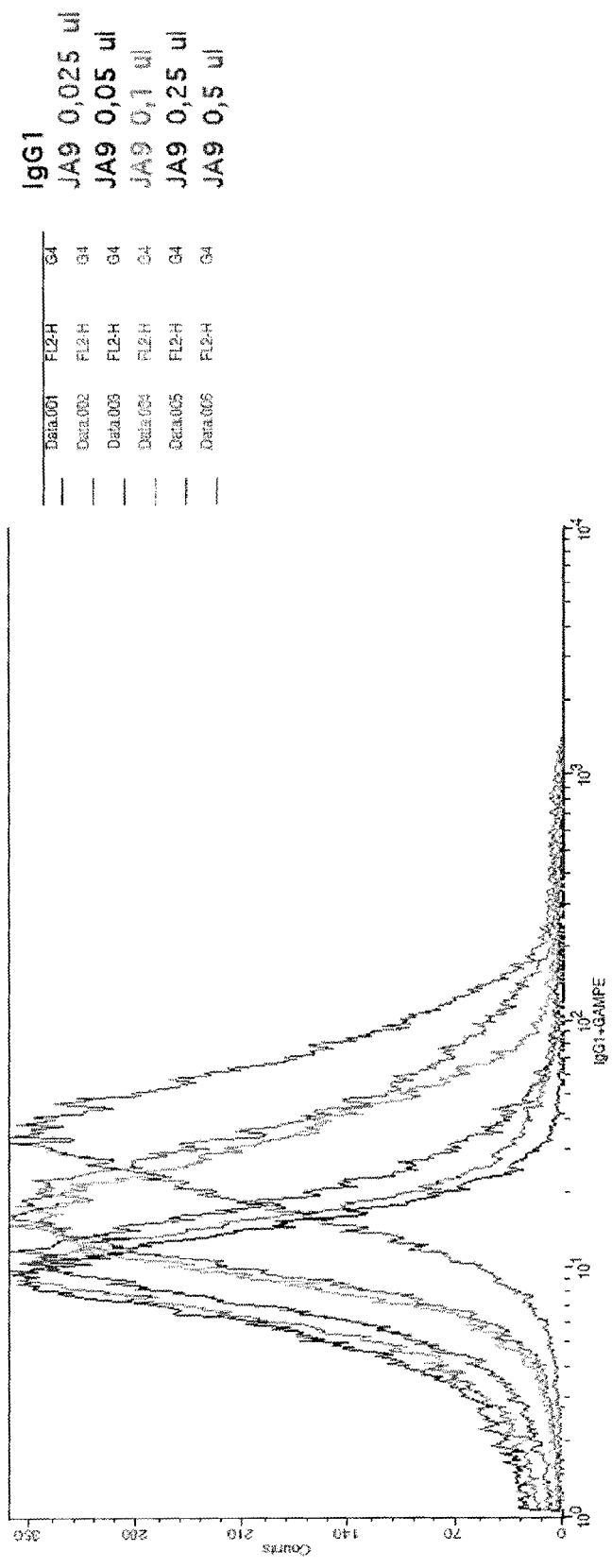
Figure 24. Calibration of JA9 antibody binding and saturation. Human RBC were fixed and saponin permeabilized (see methods).

Figure 25. Recognition of the PMCA4b protein in fixed human RBCs by the JA3 monoclonal antibody.
A.
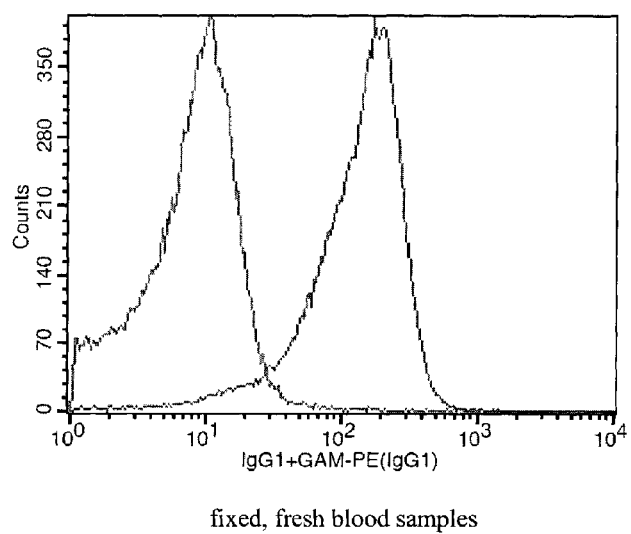
fixed, fresh blood samples
B.
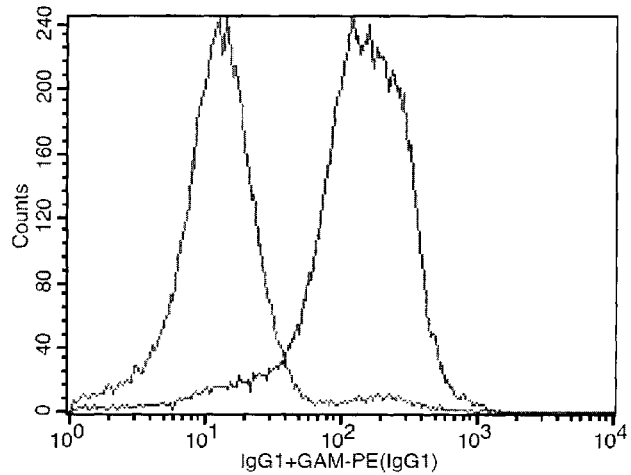
fixed, frozen-thawed blood samples Figure 26. Expression of ABCG2, ABCB1 and Glycophorin A in the erythrocytes of family members carrying wild type *ABCG2* genes or a heterozygous stop mutation in the *ABCG2* gene.
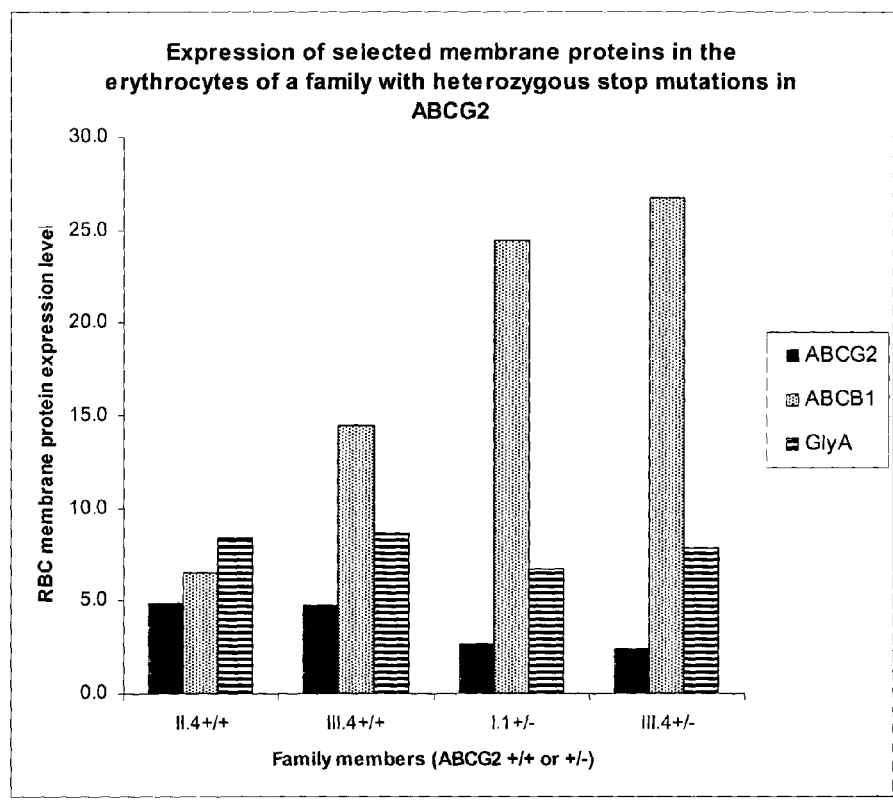

Figure 27. Western blot analysis of isolated red cell membrane preparations, compared to ABCG2-expressing Sf9 cell membrane preparations or A431 tumor cells, expressing ABCG2
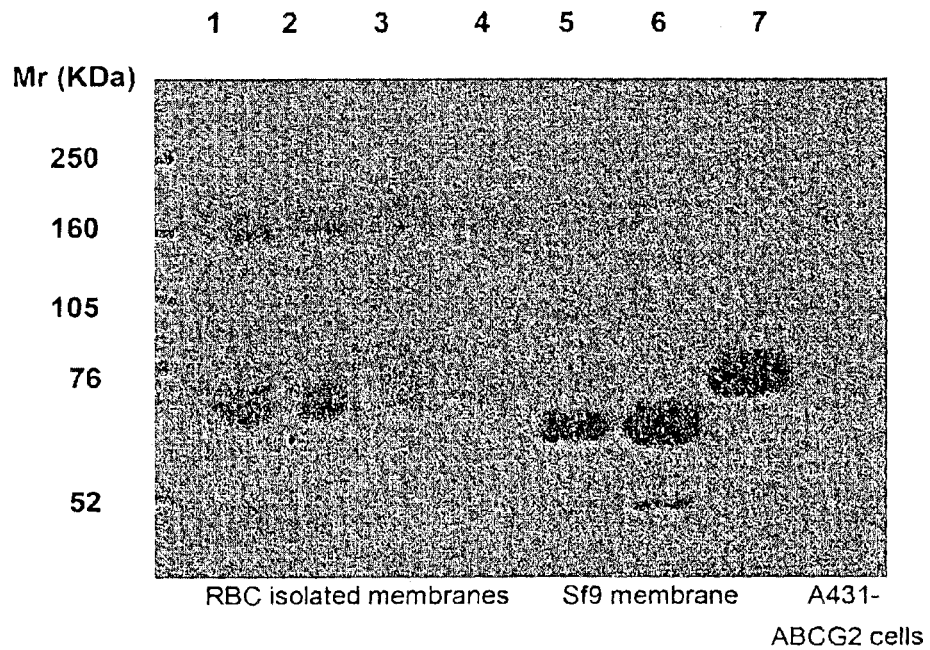
Figure 28. Comparison of ABCG2 expression on Western blot – detection by BXP21 antibody
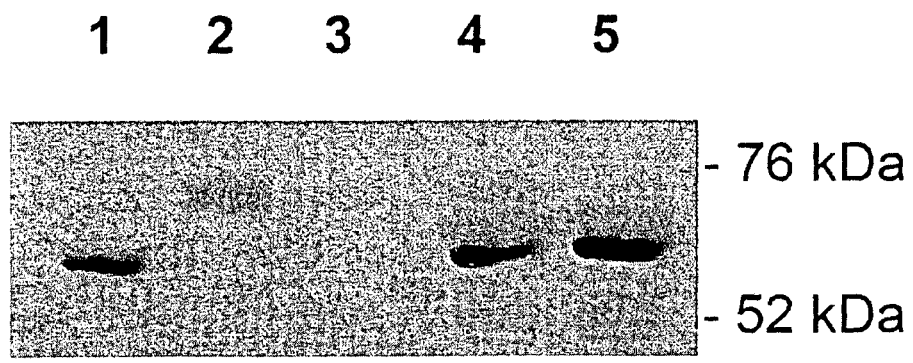

QUANTITATIVE DETERMINATION OF BIOMARKERS IN THE ERYTHROCYTE MEMBRANE

This application is the national stage of International Application PCT/HU2013/000034, filed Apr. 22, 2013, and claims priority to Provisional Application No. 61/635,893, filed Apr. 20, 2012.

FIELD OF THE INVENTION

This invention relates to determination of quantitative expression of plasma membrane proteins as biomarkers in the erythrocyte membrane. The invention includes simple, quantitative assay platforms which can be made available in most diagnostic laboratories. The platform allows performing personalized, quantitative tests for the direct expression level of a wide range of membrane proteins from small volume blood samples and connecting them to individual genetic variability, disease conditions, disease stages and complications, treatment protocols, pharmacological responses, or toxic side effects.

BACKGROUND OF THE INVENTION

Personalized medicine requires the development of biomarker diagnostic assays, reflecting individual variations and thus allowing tailored therapeutic interventions. Plasma membrane proteins play a key role in various physiological functions and pathological conditions, while currently no proper and simple assays are available for their quantitative determination. Since these proteins undergo complex processing and trafficking, mRNA levels do not correspond to their final expression level in the target membrane. Moreover, neither mRNA nor the final protein levels can be properly quantitated in human tissue samples, due to difficulties in obtaining and processing the most relevant human tissues. There are numerous data for genetic polymorphisms and mutations, potentially affecting membrane protein expression, but data are scarce for actual protein expression levels in the human body. As mentioned above, mRNA expression levels do not coincide with protein expression for most membrane proteins, and human tissue samples are also difficult to obtain. Transporters and receptors responsible for ADME-Tox properties, drug sensitivity, receptor-stimulation and inhibition, or cellular response modulation, corresponding to various diseases and drug treatments, show great individual variations. The exact determination of these variations in particular at the protein level, allowing the advance of personalized medicine, is still lacking.

It has been demonstrated that human erythrocytes (red blood cells, RBC) express numerous membrane proteins, including transporters and receptors in their single plasma membrane [Goodman S. R. et al., "The Human Red Blood Cell Proteome and Interactome" Experimental Biology and Medicine (2007), 232:1391-1408; Pasini, E. et al. (2010). "Red blood cell (RBC) membrane proteomics—Part I: Proteomics and RBC physiology." J Proteomics 73(3): 403-20]. According to currently available information on the erythrocyte membrane proteome, numerous membrane proteins with known involvement in human diseases and thought to be characteristic for special organs and tissues, are expressed in measurable quantities in the erythrocyte membrane [see Hernández-Hernández A et al., "Alterations in erythrocyte membrane protein composition in advanced non-small cell lung cancer" Blood Cells Mol Dis. (2006) 36(3):355-63; Goodman S. R. et al., see above].

Various techniques have already been applied to measure the function and/or the expression of red cell membrane proteins related to disease conditions. Erythrocyte Na—Li and Na—H countertransport activity was found to predict susceptibility to diabetes and hypertension (see Koren W, et al., Enhanced erythrocyte Na+/H+ exchange predicts diabetic nephropathy in patients with IDDM. Diabetologia. 1998 February; 41(2):201-5; Weder A. B. et al. Erythrocyte Sodium-Lithium Countertransport and Blood Pressure, Hypertension 2003, 41:842-846, Deak B, et al., Diabetes and erythrocyte Na—Li exchanger, Acta Diabetol (2003) 40:9-13).

For example, Sprague R. S. et al. ["Reduced Expression of $G_i$ in Erythrocytes of Humans With Type 2 Diabetes Is Associated With Impairment of Both cAMP Generation and ATP Release" Diabetes (2006) 55 3588-3593] assessing protein expression levels by Western analysis, reported that the expression of the heterotrimeric G-protein Gi is selectively decreased in erythrocytes of type 2 diabetes patients. Antonelou M. H. et al. ["Apolipoprotein J/Clusterin Is a Novel Structural Component of Human Erythrocytes and a Biomarker of Cellular Stress and Senescence" PLoS ONE, (2011) 6(10) e26032 1-9] identified Secretory Apolipoprotein J/Clusterin (sCLU), a chaperone that has been implicated in several pathological conditions, as a component attached to human RBCs. The authors studied the erythrocytic membrane-bound sCLU by using a combination of molecular, biochemical and high resolution microscopical methods. They have concluded that reduced sCLU protein levels are sensitive biomarkers of senescence and cellular stress. Moreover, sCLI is not an integral membrane protein All these studies used technologies (e.g. Western blot, transport activity measurements, special microscopy techniqes) are only available in specialized research laboratories, and by using these technologies it is inherently very difficult to quantify membrane protein expression. In some cases flow cytometry was also used to detect erythrocyte membrane proteins [see Saison, C. et al, (2012). "Null alleles of ABCG2 encoding the breast cancer resistance protein define the new blood group system Junior." Nat Genet 44(2): 174-7], but there was no attempt to offer a technology to quantitate this membrane protein expression.

Therefore there is still a need in the art for effective and simple biomarker diagnostic assays based on erythrocyte membrane protein expression, as well as for such assays reflecting individual variations of patients. There is also a need for such assays to allow tailored therapeutic interventions. It further appears that there is a need in the art for an effective and fast method for quantitative assessment membrane protein expression levels in erythrocytes and thereby obtain information on the condition of a subject. The recognition of membrane protein in their native or mildly fixed, membrane embedded form is a great advantage in such a technology. Moreover, it seems that there is no clear proposal in the art for the diagnostic use of membrane protein expression, including membrane receptor, and in particular membrane transporter or ABC transporter expression in the erythrocyte membranes as a reporter of a patient's condition.

The present inventors have recognized that a rapid, reliable and quantitative immunological type assay useful for diagnostic purposes can be performed if red blood cells are maintained as whole cells and thereby the membrane proteins are maintained in their original environment. Thereby membrane protein expression levels can be quantitated by measuring the levels of said proteins in the red blood cell membranes. By using the rapid, sensitive and quantitative membrane protein detection method it was possible to find a correlation of erythrocyte membrane protein expression with genetic mutations, polymorphisms, as well as drug-, and cellular responses. It has been found that the potential reflection of tissue-specific membrane protein expression in the erythrocyte membrane make this platform feasible for simple and rapid quantitative biomarker reporter assays. It has also been found that the relatively slow turnover and long life-span of the human red cells (about 120 days) makes this system a stable, relatively slowly responding biomarker platform, best reflecting individual variations or chronic alterations in membrane proteins.

BRIEF DESCRIPTION OF THE INVENTION

In an aspect the present invention relates to a method for quantitative measurement of the membrane expression level of a cell membrane protein (CMP) in a subject, said method comprising the steps of
    taking from said subject a blood sample comprising erythrocytes,
    preparing an erythrocyte test sample from the blood sample wherein one or more epitope(s) of a CMP present in the erythrocyte membrane is/are made available to a membrane protein (MP) binding agent capable of specifically binding to the one or more epitope(s), and wherein the erythrocytes are whole cells,
    adding said CMP binding agent to the test sample under conditions wherein said CMP binding agent is specifically bound to the one or more epitope(s) of said CMP present in the erythrocyte membrane, in a saturating amount to saturate said one or more epitope(s), wherein preferably said saturating amount is an amount determined based on a saturation experiment or calculated based on the determination of the amount of epitopes or CMPs,
    obtaining signal elicited by the specific binding in a cellular detection experiment wherein the erythrocyte membranes are presented in the form of whole cells and wherein the CMP binding agent is bound to said CMP present in the erythrocyte membrane in the test sample,
    converting the obtained signal into a value correlating with the number/amount of the molecules of said CMP present in the membrane of said erythrocytes, wherein said value is considered as indicative of the membrane expression level of said CMP.

In a further aspect the invention relates to a method for assessing a condition related to expression of a CMP of interest in a subject by quantitative measurement of the expression level of the CMP in the erythrocyte membranes of said subject, wherein the typical or normal or regular membrane expression range of said CMP in the erythrocyte membrane is pre-determined or known,
    said method comprising the steps of
        taking from said subject a blood sample comprising erythrocytes,
        preparing an erythrocyte test sample from the blood sample wherein one or more epitope(s) of said CMP present in the erythrocyte membrane is/are made available to a CMP binding agent capable of specifically binding to the one or more epitope(s) and wherein the erythrocytes are whole cells,
        adding the CMP binding agent to the test sample under conditions wherein said CMP binding agent is specifically bound to the one or more epitope(s) of the CMP present in the erythrocyte membrane, in a saturating amount to saturate said one or more epitope(s), wherein said saturating amount is an amount determined based on a saturation experiment or calculated based on the determination of the amount of epitopes or CMPs,
        obtaining signal elicited by the specific binding in a cellular detection experiment wherein the erythrocyte membranes are presented in the form of whole cells and wherein said CMP binding agent is bound to said CMP present in the erythrocyte membrane in the test samples,
        converting the obtained signal into a value correlating with the number/amount of the molecules of the CMP present in the membrane of said erythrocytes, wherein said value is considered as the membrane expression level of said CMP,
        comparing the obtained membrane expression level of said CMP in said subject with the typical or normal or regular membrane expression level of said CMP in the erythrocyte membrane, and
        a lack of significant difference from the typical or normal or regular membrane expression range is considered as indicative of a typical or normal or regular normal condition in said subject,
        a significant difference from the typical or normal or regular membrane expression range is considered as indicative of an atypical or irregular or not normal condition in said subject.

Preferably, the condition in said subject is related to the altered expression of said CMP in a tissue other than erythrocytes in said subject.

More preferably, the condition related to expression of a CMP in said subject is selected from the group consisting of genetic variations, genetic diseases, conditions due to a mutation in the gene of said CMP, conditions due to altered regulation of the gene expression of said CMP, preferably the up-regulation or down-regulation of said CMP.

In a preferred embodiment the steps of the method are repeated multiple times and thereby the condition of the subject is monitored, preferably to monitor any alteration in the condition of said subject upon time or any effect, e.g. a drug regimen, onset of a disease, aging etc.

Preferably the erythrocytes are whole cells, preferably a combination of intact cell and ghost cells. Preferably, in the test sample intact cells and/or erythrocyte ghosts are used.

In a preferred embodiment of the invention a control binding agent and/or a control CMP is used. In a preferred embodiment saturating amount is determined by titration of the binding sites or epitopes of the CMP by the CMP binding agent.

In a preferred embodiment of the invention in the preparation of the erythrocyte test sample fixation is used, preferably by a crosslinking fixative and/or an aldehyde fixative.

Preferably, the membrane of at least a part of the erythrocytes is permeabilized to allow intracellular binding of the CMP binding agent (e.g. antibody) by a membrane permeabilization agent causing membrane permeabilization, more preferably by a detergent or a saponin.

In an embodiment in said test sample the amount of membranes different from erythrocyte membranes is negligible in said quantitative measurement.

In an embodiment of the method the signal is obtained by adding a further, labelled binding agent capable of binding to the CMP binding agent. Alternatively, the CMP binding agent is labelled and the signal is obtained due to said label. Preferably, the label is a light absorbing moiety, a fluorescent moiety, a label with enzymatic activity or a radioactive label.

Highly preferably, the signal is obtained in a flow cytometry experiment and the number of cells comprising the CMP in their membranes is assessed.

Alternatively the signal is obtained in an assay wherein parallel samples are handled is separate containers, preferably in a plate format assay and the amount of signal is assessed, preferably in an immunosorbant assay. Preferably, the assay is an ELISA assay.

Preferably, either or both (a) the signal due to or specific to or elicited by the binding events in intact red blood cell fraction and (b) signal due to or specific to or elicited by the binding events in ghost red blood cell fraction are obtained, and converted to the value correlating with the number or amount of the molecules of the CMPs in each fraction. In an embodiment the intact red blood cell fraction and the ghost red blood cell fraction are separated.

In a preferred embodiment the preparation step cells are obtained from the blood sample, preferably by centrifugation and resuspension.

In a further aspect the invention relates to a use of an antibody specifically binding to one or more epitopes of a CMP present in the erythrocyte membrane for assessing a condition related to expression of a CMP of interest in a subject by quantitative measurement of the expression level of the CMP in the erythrocyte membranes of said subject.

Preferably, the condition in said subject is related to the altered expression of said CMP in a tissue other than erythrocytes in said subject.

More preferably, the condition related to expression of a CMP in said subject is selected from the group consisting of genetic variations, genetic diseases, conditions due to a mutation in the gene of said CMP, conditions due to altered regulation of the gene expression of said CMP, preferably the up-regulation or down-regulation of said CMP.

In a further aspect the invention relates to a system for assessing a condition related to expression of a CMP of interest in a subject by quantitative measurement of the expression level of the CMP in the erythrocyte membranes of said subject, wherein the typical or normal or regular membrane expression range of said CMP in the erythrocyte membrane is pre-determined or known, said system comprising or including means for obtaining a signal or signals elicited by the specific binding of a CMP binding agent to one or more epitope(s) of the CMP present in the erythrocyte membrane of erythrocytes of an erythrocyte test sample prepared from a blood sample taken from a subject, wherein one or more epitope(s) of the CMP present in the erythrocyte membrane is/are made available to a CMP binding agent capable of specifically binding to the one or more epitope(s), if the binding molecules are bound to the CMP present in the erythrocyte membrane in the test sample, means for converting the obtained signal into a value correlating with the number/amount of the molecules of the CMP present in the membrane of said erythrocytes, wherein said value is considered as the membrane expression level of said CMP, means for comparing the obtained membrane expression level of said CMP in said subject with the typical or normal or regular membrane expression level of said CMP in the erythrocyte membrane.

Said system may be e.g. a device or a kit or a combination of a device and a kit.

Preferably, said system is a flow cytometer device under the control of a computer, wherein said means for obtaining signal is a detector, preferably a fluorescent detector.

Preferably, said system is a plate reader under the control of a computer, wherein said means for obtaining signal is a detector, preferably an UV/VIS or a fluorescence detector. Preferably, the plate reader is an ELISA plate reader In a preferred embodiment the system of the invention is equipped with a computer programmed to analyse signals, convert signals into a value correlating with the number/amount of the molecules of the CMP present in the membrane of said erythrocytes, wherein said value is considered as the membrane expression level of said CMP, compare the obtained membrane expression level of said CMP in said subject with the typical or normal or regular membrane expression level of said CMP in the erythrocyte membrane.

In a preferred embodiment the system of the invention further comprises, preferably in the form of a kit, one or more selected from the group consisting of a CMP binding agent, means for taking from said subject a blood sample comprising erythrocytes, means for preparing an erythrocyte test sample from the blood sample wherein one or more epitope(s) of the CMP present in the erythrocyte membrane is/are made available to a CMP binding agent capable of specifically binding to the one or more epitope(s), means for processing an erythrocyte test sample prepared from a blood sample taken from a subject, preferably to provide measurement conditions wherein one or more epitope(s) of the CMP present in the erythrocyte membrane is/are made available to a CMP binding agent capable of specifically binding to the one or more epitope(s) and a CMP binding agent is capable of specifically binding to the one or more epitope(s) of the CMP present in the erythrocyte membrane.

In a preferred embodiment of the invention the condition related to expression of a CMP in said subject in any or all aspects of the invention is selected from the group consisting of genetic variations, genetic diseases, conditions due to a mutation in the gene of said CMP, conditions due to altered regulation of the gene expression of said CMP, preferably the up-regulation or down-regulation of said CMP.

In further preferred embodiments the condition is a disorder associated with overexpression of the CMP, wherein the membrane expression level of the CMP is above the typical or regular or normal expression range, or a disorder associated with underexpression or impaired expression of the CMP, wherein the membrane expression level of the CMP is under the regular/normal expression range, or a disorder associated with the lack of expression of the CMP, wherein the membrane expression level of the CMP is not significantly different from the background membrane expression level.

Preferably the genetic variation is a genetic polymorphism of the CMP affecting CMP expression.

Preferably the genetic variation is a mutant form of said CMP affecting CMP expression.

Preferably the altered regulation of the gene expression of said CMP is due to a modulation by previous medical treatment (e.g. drugs), environmental conditions, toxic effect, or somatic or psychosomatic disease or a combination thereof.

In a preferred embodiment of the invention the CMP is a membrane integrated protein or a specifically membrane attached protein or an integral membrane protein.

In a preferred embodiment of the invention the CMP is selected from the group of
- membrane transporter proteins, preferably ABC membrane transporters, ATP-dependent ion transporters and solute carrier (SLC) type transporters,—membrane channels
- membrane receptors.

In a highly preferred embodiment the CMP is an ABC membrane transporter, preferably an ABCG membrane transporter.

In an embodiment the CMP binding agent is a ligand, an aptamer, a minibody or an antibody, preferably a monoclonal antibody. In a preferred embodiment the binding agent is a monoclonal antibody or fragment or variant thereof.

According to an embodiment of the invention CMP binding agent capable of binding to the intracellular portion of the CMP is applied. In a further embodiment an CMP binding agent capable of binding to the extracellular portion of the CMP is applied. In an embodiment, both type of binding agents are applied. In a particular embodiment multiple epitope binding molecules are applied.

In a preferred embodiment of the invention at least one reference CMP binding agent is applied being capable of specifically binding to a different CMP present in the erythrocyte membrane.

In a preferred embodiment of the invention the subject is a vertebrate, preferably a mammalian, preferably a human subject or patient.

DEFINITIONS

An "epitope" is understood herein as a part of or a site on a protein molecule which is specifically recognized and bound by a protein binding molecule, preferably an antibody or a specific epitope recognition molecule. The epitope can be any part or site which provides a possibility of binding with a sufficient strength. For example, the epitope can be a linear epitope or a conformational epitope.

An "erythrocyte" is a blood cell of vertebrates that in its active form transports oxygen and carbon dioxide, combined with the red pigment haemoglobin, to and from the tissues. Human erythrocytes have a morphology of biconcave discs. Mature erythrocytes have no nucleus in mammals whereas their nucleus is contracted and chromatin is condensed in other vertebrates. In a broad sense, erythrocytes include all forms of erythrocytes, including intact or impaired forms e.g. erythrocytes ghosts. In a narrower sense, erythrocytes, or red cells or red blood cells include all forms of erythrocytes comprising their cytoplasmic content including haemoglobin.

"Erythrocyte ghosts" maintain the membrane and cytoskeletal elements of the erythrocyte as well as their original morphology, but do not comprise their original cytoplasmic contents. Erythrocyte ghosts are considered as whole cells in the sense of the present invention.

The "erythrocyte membrane" is the outer portion of the erythrocyte or red blood cell separating the inner or intracellular space and the outer or extracellular space when the erythrocytes are whole cells.

"Significant" is to be understood herein as statistically significant according to any statistical hypothesis testing method appropriate in the given assay method. The skilled person is familiar with statistical hypothesis testing methods.

A "significant difference" between two sets of measured values or between a measured value and a set of measured values defining a range (e.g. as a confidence interval) is understood as a statistically significant difference. Preferably, in this case a hypotheses that there is no relationship between two sets of values or between the value and the set of values cannot be rejected based on the given statistical method applied.

"Whole cells" are understood herein as cells the cell membrane of which forms a compartment or defines an inner and an outer space even if said membrane is permeabilized or said cell is functionally impaired.

"Intact cells" are cells which maintain their essential cellular functions.

A "population" of subjects is to be understood herein as a total number of subjects sharing a common feature. Without limitation, the common feature can be e.g. being inhabitant of a specific geographic area, belonging to a nation, race, age or sex, sharing a common phenotype or genotype, or a condition said subjects are characterized by or a disorder or disease or symptom they suffer in.

A "cohort of subjects" is understood herein as a plurality of subjects selected from a larger group of subjects either arbitrarily or based on a common feature or characteristic, e.g. a phenotype or genotype they share, a condition they are characterized by or a disorder or disease or symptom they suffer in. The number of subjects in a cohort is not specifically limited but rather is to be defined or decided based on the experiment they are to be involved in.

A "condition" is a purposive selection of features of a subject or a group of subject. A condition may describe the state or status of said subject. A condition may be for example a disorder or disease or set of symptoms, a healthy status or a genetic feature or a phenotype.

A "genetic feature" includes conditions due to or related to or being genetic variations, genetic diseases, conditions due to a mutation in the gene of cell membrane protein, conditions due to altered regulation of the gene expression, conditions changing the specific membrane expression level of the membrane protein or different membrane expression levels due to different isoforms of the same protein.

A "typical range" or a "regular range" of values measured in connection with a cohort or a population of subjects is a range of values typical for the majority of subject or for a subgroup of subjects sharing a common feature wherein said subgroup comprises the majority of the subjects in said cohort or population.

A "typical condition" or a "regular condition" of subjects is characteristic to the majority of subjects in a cohort or in a population.

A "normal range" of values measured in connection with a cohort or a population of subjects is a range of values having some or any advantage for subjects characterized thereby over values falling outside the range and being typical for other subjects.

A "normal condition" of a subject is a condition having some or any advantage for said subject over other condition characteristic to other subjects.

A "cell membrane protein" (CMP) is a protein molecule or assembly of protein molecules that is specifically attached to, or associated with the cell membrane of a cell.

A "membrane integrated protein" or an integral membrane protein is CMP that is permanently attached or firmly anchored in the membrane of a cell via its hydrophobic domains interacting with the membrane phospholipids.

A "membrane transporter" is a membrane integrated protein which is capable of transporting, e.g. exporting or extruding or importing entities, either actively or passively through the membrane into which it is integrated in. The entity can be e.g. a molecule or an ion.

"ABC transporter" stands for ATP-binding cassette transporters which are a superfamily of membrane transporters that utilize the energy of adenosine triphosphate (ATP) hydrolysis to carry out certain biological processes including transport of entities across membranes. Denominations and subfamilies of ABC transporters are used herein as assigned by the HUGO Gene Nomenclature Committee (HGNC).

For example, membrane transporters of the "ABCG family" belong to the G subfamily of ABC transporters consisting of half-transporters, which oligomerise to form the functional transporter.

As used herein the singular forms "a", "an" and if context allows "the" include plural forms as well unless the context dictates otherwise.

"Isolated" means altered "by the hand of man" from the natural state. If a molecule or composition occurs in nature, it has been "isolated" if it has been changed and/or removed from its original environment.

The term "comprises" or "comprising" or "including" are to be construed here as having a non-exhaustive meaning and allow the addition or involvement of further features or method steps or components to anything which comprises the listed features or method steps or components.

The expression "consisting essentially of" or "comprising substantially" is to be understood as consisting of mandatory features or method steps or components listed in a list e.g. in a claim whereas allowing to contain additionally other features or method steps or components which do not materially affect the essential characteristics of the use, method, composition or other subject matter. It is to be understood that "comprises" or "comprising" or "including" can be replaced herein by "consisting essentially of" or "comprising substantially" if so required without addition of new matter.

ABBREVIATIONS

| | |
|---|---|
| GlyA: Glycophorin A, | IgG: immunoglobulin G, |
| mAb: monoclonal antibody, | PFA: paraformaldehyde, |
| PMCA: Plasma membrane calcium ATPase, | SNP: single nucleotide polymorphism, |
| uL: microliter | PBS: phosphate buffered saline |
| CMP: cell membrane protein | FSC: forward scatter |
| SSC: side scatter | ABC: ATP binding cassette |
| ATP: adenosine triphosphate | |

Freshly drawn human blood (25 uL) was diluted in 4 mL of phosphate buffered saline (PBS) containing 1% paraformaldehyde (PFA) and fixed for 60 min at 25° C. The cells were centrifuged with 3,000×g for 10 min and the pellet was resuspended in 100 uL PBS. Antibody staining was performed for 40 min at 37° C. by using the BXP34 (Panel B), the BXP21 (Panel C) the 5D3 (Panel D) monoclonal antibodies specific for ABCG2, or the respective IgG control antibodies. Secondary antibodies corresponding to the IgG type and labeled with phycoerythrin (PE) were added to the cells, incubated for 30 min at 37° C., washed and resuspended in PBS. In Panel E cells were directly stained with an FITC-conjugated anti-Glycophorin A monoclonal antibody.

Intact erythrocytes and erythrocyte ghost were gated out based on the forward scatter (FSC) and side scatter (SSC) parameters (Panel A). Both fractions were analyzed for antibody staining. In each case the IgG control staining is shown by a thin line, antibody staining in the ghost or intact cell fractions by a thick line.

FIG. 2. ABCG2 is differentially expressed in the red blood cells of individuals carrying wild-type, polymorphyic or mutant ABCG2 alleles FIG. 2A. ABCG2 expression in individuals carrying wild-type (WT) or polymorphic (Q141K, V12M) ABCG2 alleles or a heterozygous stop mutation (STOP)

The Figure shows a box-interpretation of the data and the conidentiality intervals. ABCG2 expression is calculated based on the combined reactivity of anti-ABCG2 mAbs, by calculating a weighed average of the specific binding results obtained by using three independent antibodies.

FIG. 2B. Pedigrees of two families carrying different ABCG2 premature stop mutations—co-segregation of the heterozygous mutation with reduced erythrocytic ABCG2 expression levels.

Blood samples of obtained from the family members of the two healthy volunteers carrying the premature stop mutations (see FIG. 2A—indicated with arrowheads) were analyzed for ABCG2 expression and the respective mutations. The RBC-G2 factor values, reflecting ABCG2 expression in erythrocytes, are shown in parentheses. As documented, all heterozygous carriers of the two different ABCG2 stop mutations show significantly reduced ABCG2 expression levels in the erythrocyte membrane. Family members not available (N.A.) for blood donation are also labeled.

FIG. 3. Western blot examination of the human ABCG2 protein in human red cells, ABCG2 heterologously expressed in Sf9 insect cells and ABCG2 expressed in human K562 tumor cells.

Lanes 1-4: human RBC membrane preparations, 70 ug membrane protein; Lanes 5 and 6: Sf9 cell membrane preparations, 0.1 ug and 0.2 ug membrane protein; Lanes 7-8: K562 human tumor cells retrovirally overexpressing ABCG2 (lane 7) or control K562 cells (lane 8), 10 ug membrane protein.

Figure 1B:
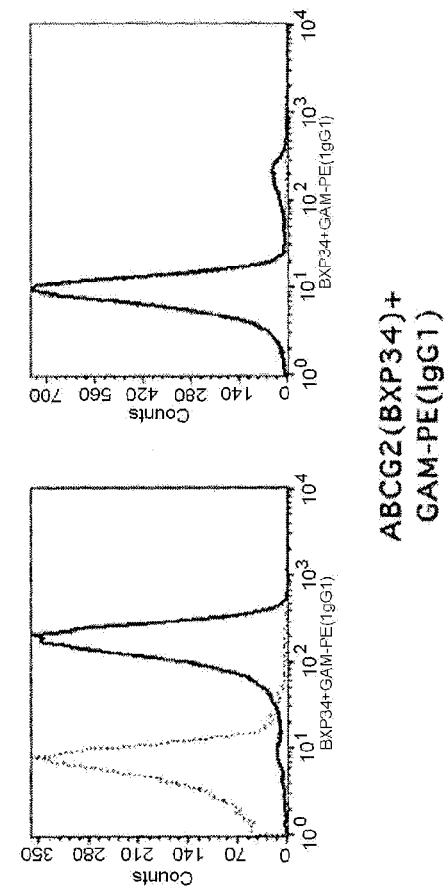
FIGS. 1A to 1E. Quantitative determination of ABCG2 expression in the erythrocyte membrane by flow cytometry.
Figure 1C:
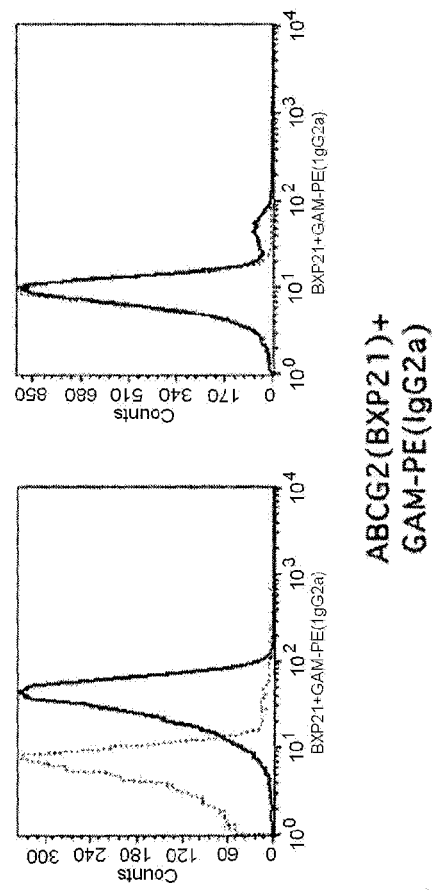
Figure 1A:
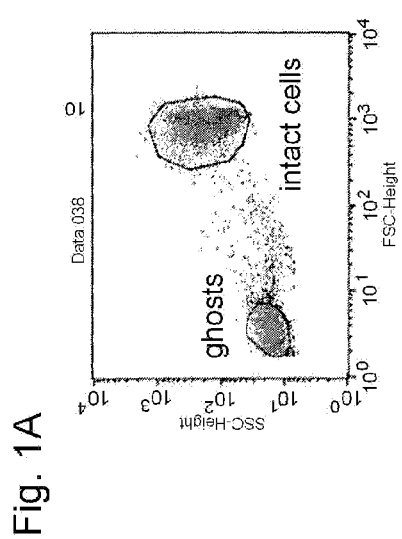
Figure 1D:
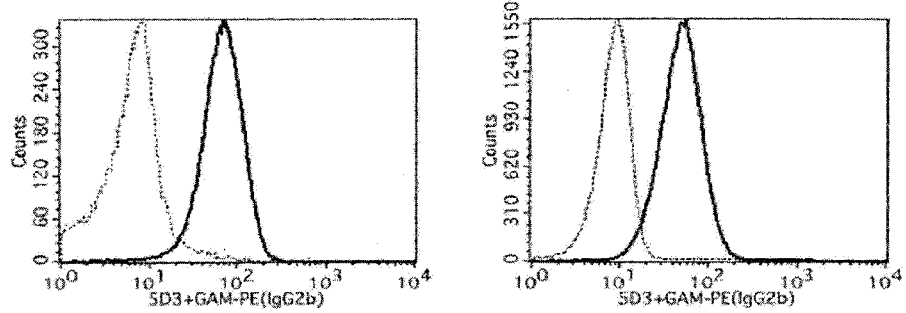
Figure 1E:
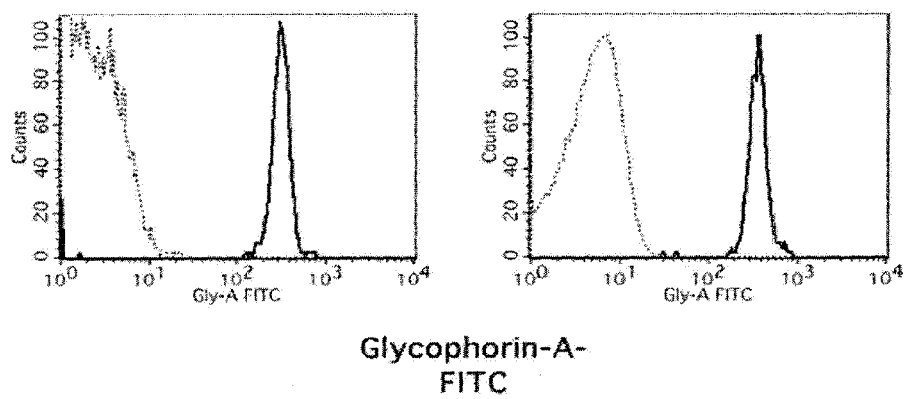
Figure 4:
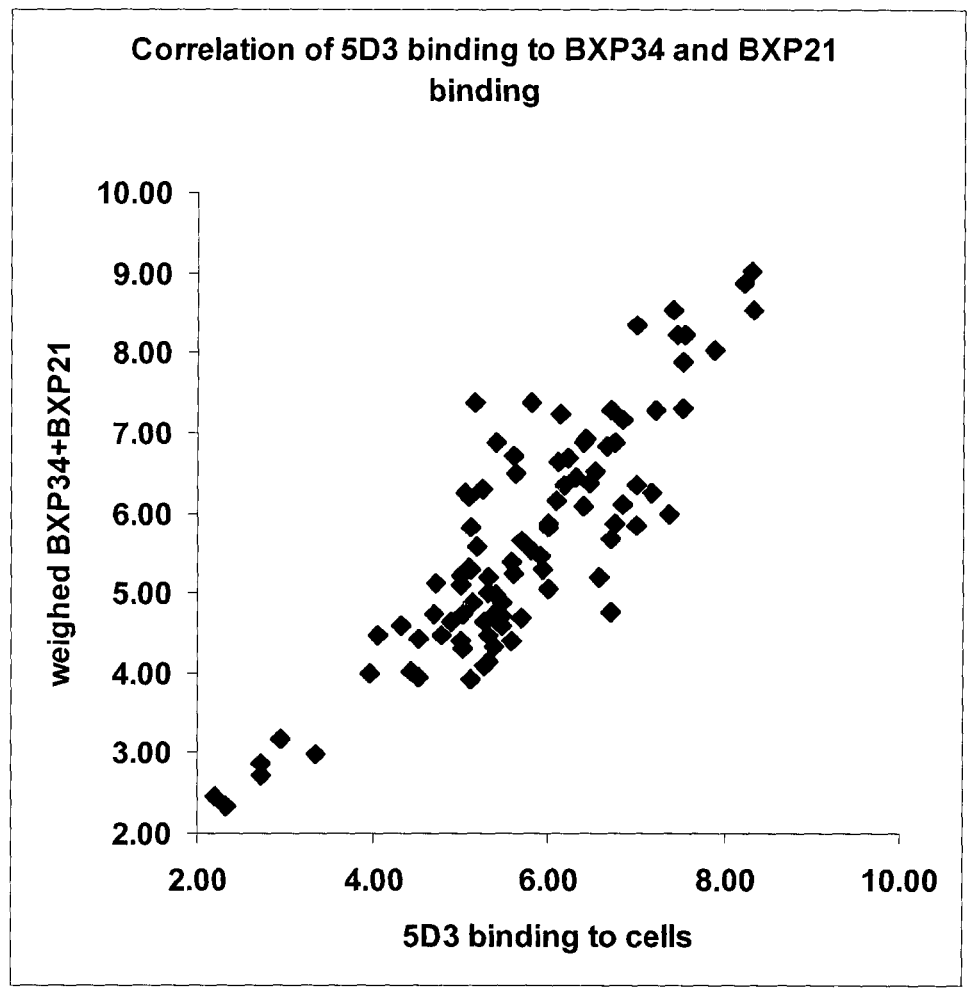

FIG. 4. Correlation of the ABCG2 expression level detected by the 5D3 monoclonal antibody, recognizing the ABCG2 protein on an extracellular epitope, and the weighed average of BXP21 and BXP34 antibodies (BXP34/3+BXP21)/2. The correlation is linear; the value of the correlation coefficient R is 0.859

Figure 5:
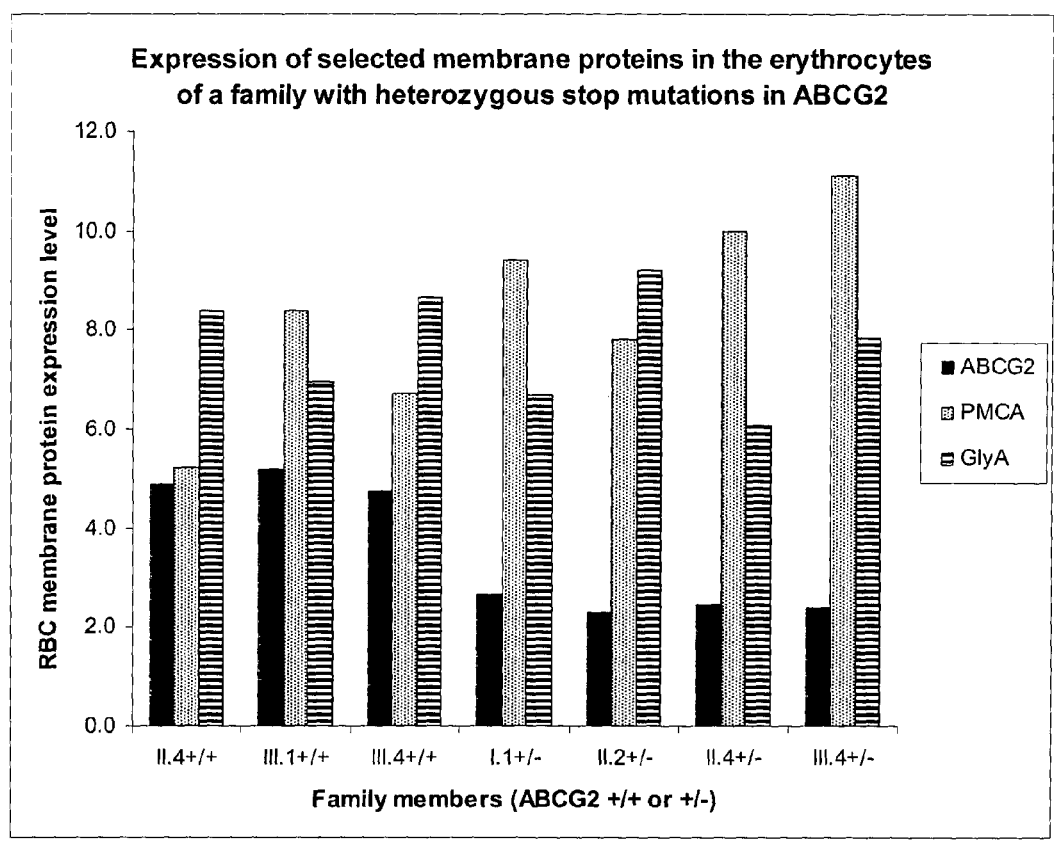

FIG. 5. Expression of three selected membrane proteins in the erythrocyte membrane in family 2 with members having a heterozygous frameshift mutation on one of the ABCG2 alleles (labeled as +/−), as compared to ABCG2 wild type individuals of the same family (labeled as +/+) Family members are labeled according to generations (I, II, III), and blood samples obtained (1-4).

FIG. 6. Determination of the erythrocyte membrane ABCG2 expression level in frozen-thawed blood samples. Application of three different anti-ABCG2 monoclonal antibodies.

FIG. 6A: peripheral blood samples—frozen stored and thawed erythrocytes. Determination of ABCG2 expression by using specific monoclonal antibodies. SSC/FSC view, control IgG and BXP34 binding to frozen stored human red cells.

FIG. 6B: Detection of the ABCG2 protein by using 3 monoclonal antibodies BXP34, BXP21, 5D3

FIG. 7. Determination of the erythrocyte membrane ABCG2 expression level in frozen-thawed bone marrow aspirate samples. Application of three different anti-ABCG2 monoclonal antibodies.

FIG. 7A: Bone marrow aspirate samples—SSC/FSC view, control IgG and BXP34 binding to frozen stored human red cells.

FIG. 7B: Detection of the ABCG2 protein by using 3 monoclonal antibodies BXP34, BXP21, 5D3

FIG. 8. Quantitative determination of erythrocyte membrane ABCG2 expression in frozen-thawed blood samples.

Figure 8A:
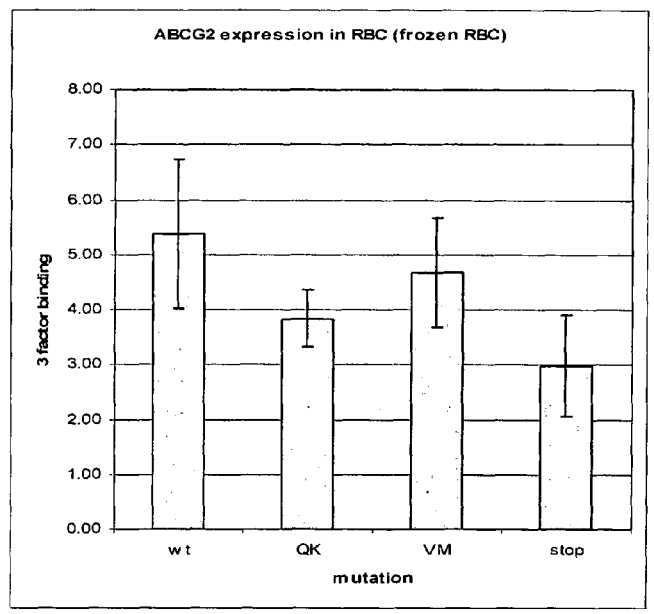

FIG. 8A: Expression levels as described by the average of the 3 mAb binding (mean values +/−SD values).

Figure 8B:
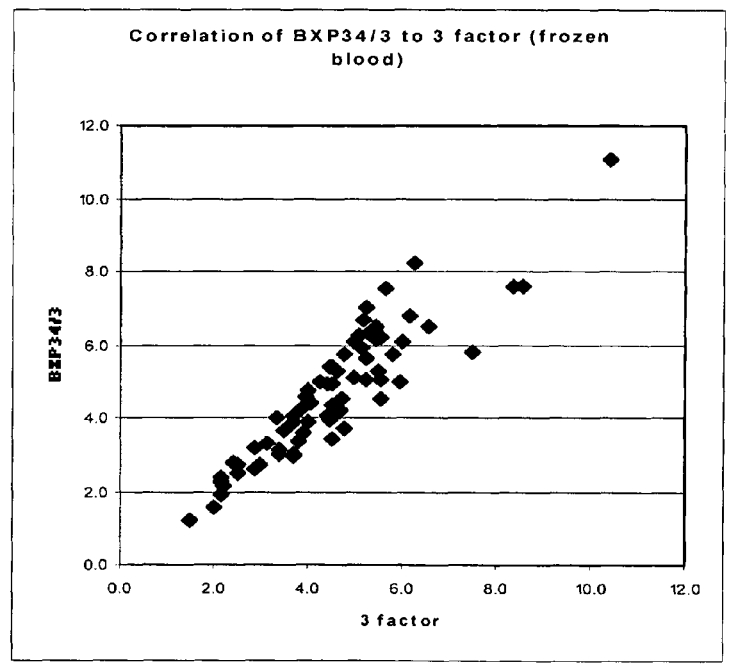
Figure 14A:
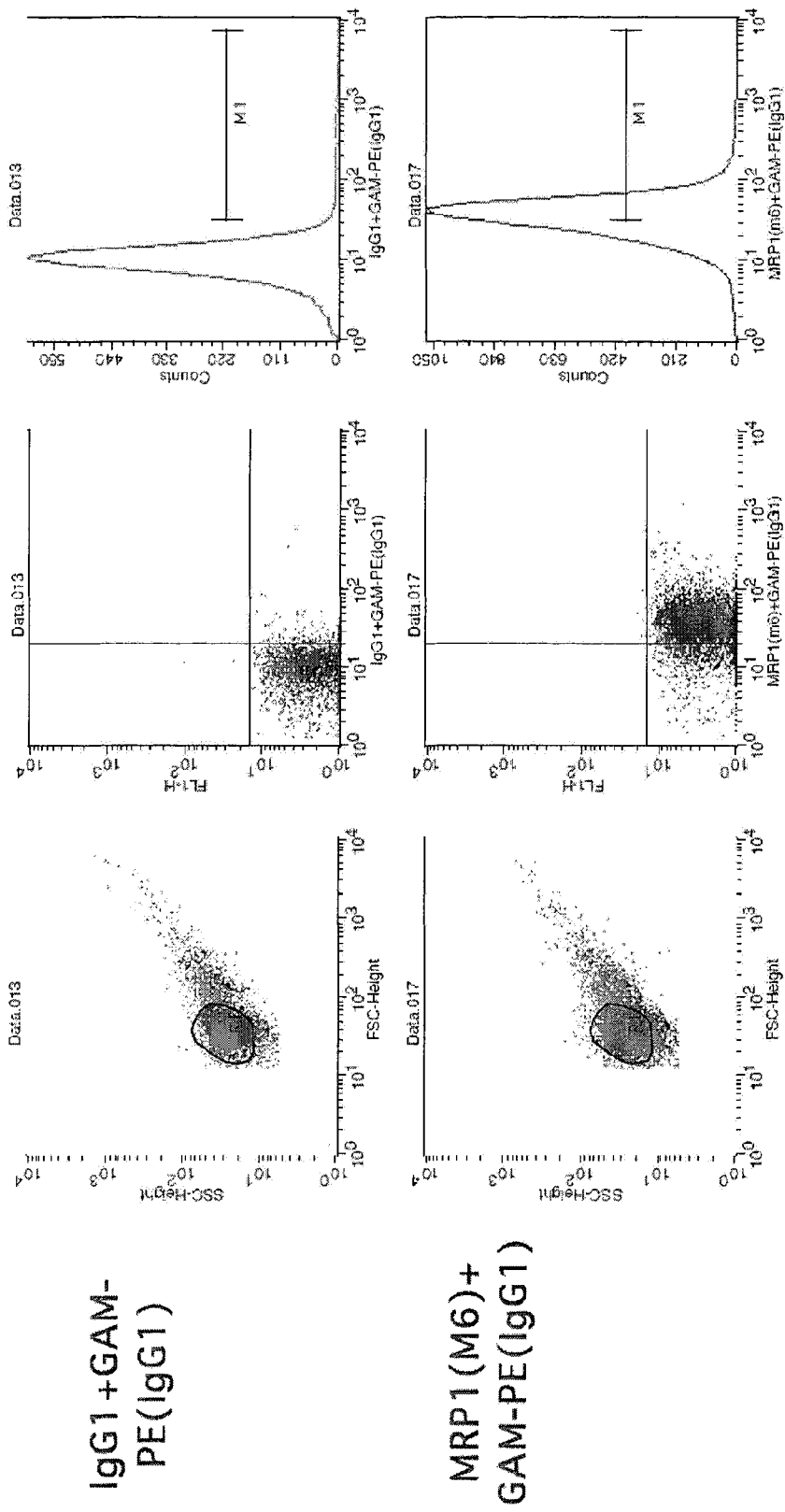
Figure 14B:
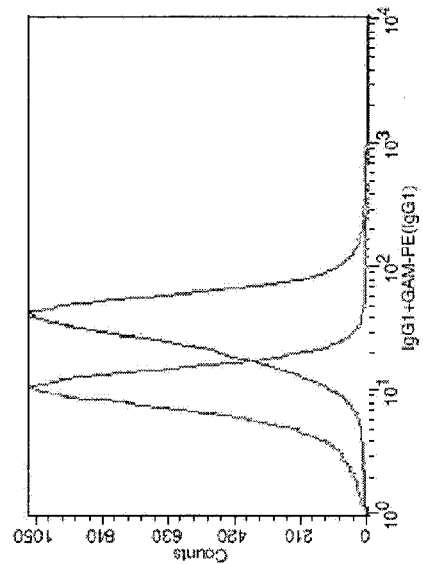
Figure 14C:
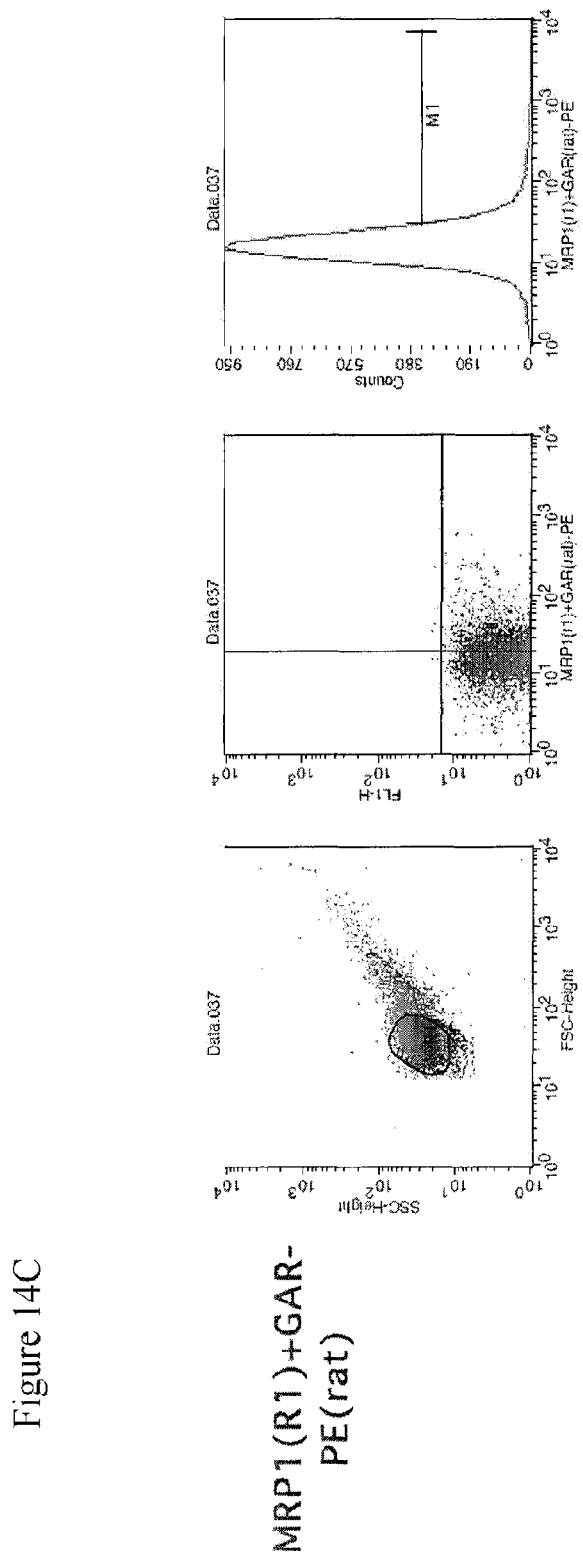
Figure 14D:
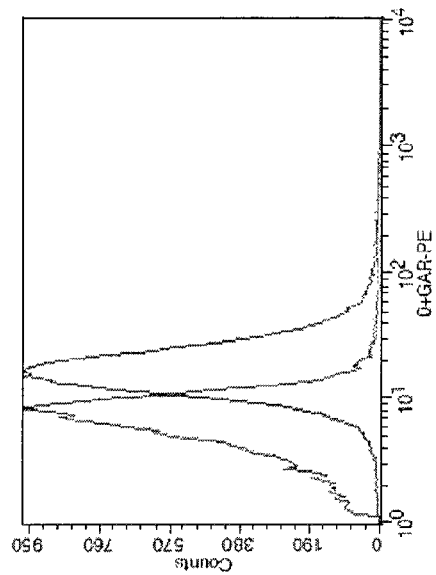

FIG. 8B: Correlation of BXP34 binding to the average mAb binding, calculated from the values of three independent anti-ABCG2 antibodies. Linear correlation with a high correlation coefficient (R=0.88)

FIG. 9. Quantitative determination of erythrocyte membrane ABCG2 expression in microplates. Blood samples of three independent donors showing similar ABCG2 expression (ABCG2 wild-type) values, as determined by flow cytometry, were distributed in microplates in triplicates. The average values of fluorescence reflecting mAb binding values are shown for the three donors, labeled with different colors.

FIGS. 10A to 10B. Detection of ABCB1 in human red cells by a specific monoclonal antibody MRK16. Freshly drawn human blood cells were fixed in 1% PFA Specific labeling in the ghost fraction—MRK16 mAb:

FIG. 11. Detection of ABCB1 in human red cells by two ABCB1 specific monoclonal antibodies. Freshly drawn blood sample—fixed and saponin-permeabilized cells—specific labeling with MRK16 and UIC2 mAbs: MRK16 mAb, UIC2 mAb FIG. 12. Detection of ABCB1 in human red cells by two ABCB1 specific monoclonal antibodies. Frozen and thawed blood sample—fixed and saponin-permeabilized cells—specific labeling with MRK16 and UIC2 mAbs: MRK16 mAb, UIC2 mAb

FIG. 13.

FIGS. 13A1 to 13A3: Detection of ABCB6 in human red cells by a monoclonal antibody reacting with a cell-surface epitope of human ABCB6 (freshly drawn blood cells fixed in 1% PFA); ghosts; intact cells FIG. 13B: Quantitative determination of erythrocyte membrane ABCB6 expression in blood samples of individuals carrying wild-type or mutant ABCB6 alleles (mean fluorescence ratio, ABCB6 antibody/isotype control). 44 donors with wild-type ABCB6, 3 donors with heterozygous mutations in the ABCB6 gene FIG. 13C: Pedigree of a family carrying ABCB6 mutations—co-segregation of the mutations with reduced erythrocytic ABCB6 expression levels. Values in parentheses indicate the mean fluorescence ratio (ABCB6 antibody/isotype control)

FIGS. 14A to 14D. Detection of ABCC1 in human red cells by two monoclonal antibodies (M6, a mouse monoclonal antibody, and R1, a rat monoclonal antibody) reacting with intracellular epitopes of the human ABCC1 protein (freshly drawn blood cells, unfixed membranes).

FIG. 15. Detection of ABCC4 in human red cells by a mouse monoclonal antibody (M4-1-10) reacting with an intracellular epitope of the human ABCC4 protein (freshly drawn blood cells, unfixed membranes).

FIGS. 16A to 16D. Detection of ABCA1 in human red cells by two monoclonal antibodies (Panel A: AB7360, a rabbit polyclonal antibody), and Panel B: ABH10, a mouse monoclonal antibody) reacting with intracellular epitopes of the human ABCA1 protein (freshly drawn blood cells, unfixed membranes). As a control, the lack of ABCC6 protein in the red cell membrane is indicated by using the M6-II-7, ABCC6-specific monoclonal antibody. On Panel B, a titration with the ABH10 mAb to obtain maximum binding/labeling is also documented.

FIG. 17. Detection of ABCC3 protein in human red cells by a monoclonal antibody M3-II-9, reacting with an intracellular epitope of the human ABCC3 protein (freshly drawn blood cells fixed in 1% PFA). A titration with the mAb to obtain maximum binding/labeling is also documented.

FIGS. 18A to 18C. Detection of membrane bound actin in human red cells by TRITC-Phalloidin binding. Freshly drawn human blood cells were fixed in 1% PFA. Specific labeling only in the ghost fraction (Panel A) was detected, addition of saponin (Panel C) did not alter phalloidin binding. Saturation of phalloidin binding was observed already at the addition of low amounts (0.125 uL) of labeled phalloidin. A. Ghost fraction; B. Intact red cell fraction; C. Saponin permeabilized red cells FIGS. 19A to 19B. Detection of extracellular WGA (wheat germ agglutinin) binding proteins in human red cells. Freshly drawn human blood cells were fixed in 1% PFA.

Specific WGA labeling was obtained both in the ghost fraction (Panel A), and the intact red cell fraction (Panel B), saponin did not alter WGA binding (not shown). A saturation of WGA binding was achieved only by the addition of high amounts (over 0.25 uL) of labeled WGA.

A. Ghost fraction; B. Intact red cell fraction

FIG. 20. Recognition of the PMCA protein in fixed human RBCs by the 5F10 monoclonal antibody recognizing all PMCA isoforms. A full recognition of the PMCA protein is observed in the ghost fraction (blue line), while in the intact cell fraction most of the protein is not recognized by the antibody (some permeabilized cells show mAb staining—red line). The isotype control is shown by light blue line.

FIG. 21. Calibration of 5F10 antibody binding and saturation. Human RBC were fixed and the PMCA protein was quantitated in the ghost fraction by the 5F10 monoclonal antibody, recognizing all PMCA isoforms (see Methods section). Maximum labeling was obtained by 2.5-5 µg/ml antibody concentration, higher mAb concentrations reduced specific binding.

FIG. 22. Calibration of 5F10 antibody binding and saturation. Human RBC were fixed and saponin permeabilized (see methods). The PMCA protein was quantitated by the 5F10 monoclonal antibody, recognizing all PMCA isoforms. Maximum labeling was obtained by 0.05-0.1 ul (×ug/ml) of antibody concentration, higher mAb concentrations reduced specific binding.

FIG. 23. Recognition of the PMCA4 protein in fixed human RBCs by the JA9 monoclonal antibody. Recognition of the PMCA protein is observed in the ghost fraction. Maximum labeling was obtained by 0.25 ul (×ug/ml) antibody concentration, higher mAb concentration reduced specific binding.

FIG. 24. Calibration of JA9 antibody binding and saturation. Human RBC were fixed and saponin permeabilized (see methods). The PMCA4 protein was quantitated by the JA9 monoclonal antibody, recognizing the PMCA4 isoform. Maximum labeling was obtained by 0.25 ul (×ug/ml) of antibody concentration, higher mAb concentration reduced specific binding.

FIG. 25. Recognition of the PMCA4b protein in fixed human RBCs by the JA3 monoclonal antibody. Recognition of the PMCA protein is observed in the ghost fraction. PMCA4b recognition is also observed in frozen-thawed blood samples (Panel B)

FIG. 26. Expression of ABCG2, ABCB1 and Glycophorin A in the erythrocytes of family members carrying wild type ABCG2 genes or a heterozygous stop mutation in the ABCG2 gene.

FIG. 27. Western blot analysis of isolated red cell membrane preparations, compared to ABCG2-expressing Sf9 cell membrane preparations or A431 tumor cells, expressing ABCG2 [1].

Lanes 1-4: Red cell membrane preparations from different donors, 10 μg/lane,

Lanes 5-6: Sf9 cell membrane, expressing human ABCG2, 0.1 and 0.3 μg,

Lane 7: A431 tumor cells expressing human ABCG2, 10 μg.

FIG. 28. Comparison of ABCG2 expression on Western blot—detection by BXP21 antibody.

Lane 1: Sf9 cell-ABCG2, 0.03 μg membrane protein,
Lane 2: K562-ABCG2 cells, 5 μg total protein,
Lane 3: K562 control cells, 5 μg total protein,
Lane 4: Donor red cells (wt ABCG2), 50 μg total protein,
Lane 5: Donor red cells (heterozygous stop ABCG2), 50 μg total protein.

DETAILED DESCRIPTION OF THE INVENTION

The present invention describes a rapid assay method to process human erythrocytes from a few microliters of blood samples and perform specific antibody-based detection of the erythrocyte membrane proteins in these samples. The membrane protein is particularly an integral membrane protein or a membrane anchored protein, preferably a transmembrane protein and not a protein merely attached to the membrane. Such proteins which, even if have a function in connection with membranes or membrane proteins, do not have a transmembrane segment or domain or are not integrated into the membrane, are preferably excluded from the claimed scope. For example, in a preferred embodiment, transmembrane receptors like G-protein-coupled receptors are considered as membrane proteins whereas G-proteins are preferably not. Membrane protein-specific antibodies by now are widely available to perform specific and quantitative detection of membrane proteins. In addition, specific recognition (ligand) molecules, e.g. natural compounds or artificial e.g. nucleotide-based aptamers are also available or can be selectively generated for this purpose.

In the present invention whole erythrocyte cells are used in the measurement and no separation of the membrane protein, like in Western-blot, or embedding the sample like in tissue sections is used. Also the cells are not disrupted, i.e. the erythrocyte membrane environment of the cell membrane proteins is maintained.

We have found that prior art methods for the quantitation of membrane proteins are not suitable for the diagnostic purposes of the present invention. Specifically, Western blot, while both the monomeric and dimeric forms of ABCG2 in the red cell membrane could be detected, was found not to be suitable for the proper quantitation of small changes in ABCG2 expression. (see Supplementary Materials).

Moreover, the transport function measurements are functional measurements which do not clearly report on expression of these proteins and their consequent presence in the membranes of inside-out red cell membrane vesicles. We found that in this regard that in intact human erythrocyte this function could not be properly studied by fluorescent measurements, e.g. by flow cytometry, as the fluorescence may be quenched by the high concentrations of hemoglobin, just as in case of all the available ABCG2-transported compounds.

So as to assist quantitative measurements, protein level quantitation can be performed on the basis of model system protein expression, or based on comparison of erythrocyte protein expression levels in cases of known polymorphic variants and/or mutations. Advisably, antibody specificity for selected membrane protein recognition is carefully assessed by control studies, including model system protein expression, specific (e.g. peptide, protein epitope) inhibition, multiple and competitive recognition studies. The application of isoform-specific antibodies further extends the use of this method to follow the expression of specific membrane protein isoforms.

In the present invention erythrocyte protein expression levels measured by the rapid assay method described herein are related to the condition or status of a subject, e.g. a patient. Typically this condition is not specific to erythrocytes, nevertheless the expression levels measured in erythrocyte membranes reflect the condition of the subject. The condition can be of several type, e.g. genetic variations, genetic diseases, conditions due to a mutation in the gene of cell membrane protein, conditions due to altered regulation of the gene expression, conditions changing the specific membrane expression level of the membrane protein or different membrane expression levels due to different isoforms of the same protein. Thus, it is contemplated that the regulation of the membrane protein expression in the red blood cell is related to the condition of the subject or patient even if this condition effects other tissues or body parts.

According to the present invention the individual genetic background of a subject to membrane protein studies can be connected. To this end determination of the mutations or polymorphisms relevant to the sequences coding for these proteins can be performed. Based on the genetic information, bioinformatics analysis may provide a suggestion for the expected expression level of the selected membrane protein in the relevant tissues. However, these predictions are uncertain and diagnosis cannot be relied upon them. In the present description a validation of the correlation between erythrocyte expression and genetic background for selected membrane proteins is demonstrated.

In addition to reflect the genetic background of a given membrane protein, the assay is also applicable to follow changes in membrane protein expression under various disease conditions, changing environmental conditions, depending on food consumption, or medical (e.g. drug) treatment. The regulation of membrane protein expression is expected to modulate this expression in red cells as well, and a slow, dynamic change in the expression levels (also affected by the relatively long life-span of red cells) allows to follow long-term kinetic changes in membrane protein expression. Since obtaining repeated blood samples is not limiting this diagnostic assay, changes in membrane protein expression affected by medical treatment or other conditions may be continuously followed.

In the rapid assay method of the invention the expression level of a membrane protein of erythrocytes present in the blood sample of a subject is assessed quantitatively, by adding an epitope binding agent, e.g. an antibody, directly to the erythrocyte membrane comprising the membrane protein. Thus a minimum requirement for sample preparation is that the epitope shall be exposed to the binding agent. If the epitope is present on the extracellular part of the membrane protein this requirement is met. If the epitope is an intracellular epitope the erythrocyte membrane is to be permeabilized.

A fixation step is preferred, though in certain embodiments, if there is no danger of the decay or damage of the membrane proteins and/or the erythrocyte membranes, it may be omitted. The inventors have found that a crosslinking fixative and/or an aldehyde fixative, preferably paraformaldehyde is preferred.

Preferably, the serum should be removed and/or cellular elements of blood obtained e.g. by centrifugation and resuspension. Thereby also interference with soluble proteins can be excluded.

It is advantageous if whole cells, including intact cells and erythrocytes ghosts and, if required, cells with permeabilized membranes are used. It is not necessary to prepare membrane preparations from the red cell membranes and such a step can be omitted; though in certain embodiments it may be applied.

In most cases, as the overwhelming majority of them are erythrocytes, there is no need to remove cellular elements of blood and the assay is further simplified by the omission of this step.

The binding agent is preferably added to the sample when the erythrocyte membranes, preferably the erythrocyte cells, preferably whole cells are in a cell suspension, i.e. they are in a liquid phase.

Sample preparation methods, including fixation and permeabilization are known in the art and are described e.g. in the books "Immunocytochemical Methods and Protocols" [Editor(s): Constance Oliver, Maria Célia Jamur, Series: Methods in Molecular Biology, Springer, Vol. 588, (2009)] and "Immunohistochemistry" [Methods Express Series, Edited by Simon Renshaw, Scion Publishing Ltd. (2006)]. As disclosed herein the sample preparation method shall meet the requirements of the rapid assay of the invention, i.e. preserve erythrocyte membranes comprising the membrane protein the amount or level of which is to be measured and remove possible contaminant.

The binding agent is, in a preferred embodiment an antibody, preferably a monoclonal antibody. Antibody fragments, like single chain antibody fragments (scFv) and Fab fragments carrying the variable region can be applied, too. Diagnostic antibodies may also be prepared using the phage display method or other display methods or molecular evolution methods known in the art.

Further binding agents recognizing epitopes can be used. For example, applying the principles observed with binding properties of antibodies, molecules having binding sites specific to a given target molecule on proteins that originally have no receptor characteristics have been prepared. Appropriate scaffolds are e.g. fibronectin type 3 and the lipocalin protein can be applied and the binding site recognizing the epitope can be formed by a directed evolution technique combined e.g. by a display methodology.

Binding can be detected e.g. by a labeled compound specifically binding to the binding agent. In a alternative method, the binding agent itself can be labeled.

In a preferred embodiment the binding agents themselves bound to the epitope are detected. In this case e.g. a labeled, e.g. conjugated secondary binding agent (e.g. antibody) can be used to detect binding to the membrane protein epitope. The secondary binding agent shall be specific to the first binding agent.

The label shall allow to obtain a signal which can be quantified. Thus, the label can be without limitation e.g. a conjugate comprising a chromophore or a fluorophore (a fluorescent label) or an enzymatic label or a receptor ligand pair. Labeling methods are available and taught e.g. in "Immunocytochemical Methods and Protocols" (see above), "Immunohistochemistry" (see above) or in "Immunohistochemistry: Basics and Methods" [I. B. Buchwalow and W. Böcker, Springer (2010)].

In a preferred embodiment of the assay in which the binding and detection takes place is a solution phase assay wherein the cells are suspended in a medium and both binding of the binding agent and detection of the signal is carried out in solution, preferably in the same medium.

In an alternative preferred embodiment the erythrocyte membranes, preferably erythrocyte cells having the binding agent added are bound to a surface of a container, e.g. a vial or a well of a plate, and the signal is obtained from this container. In an embodiment, binding and detection of the signal is carried out in the same container. In a further embodiment the binding agent is added and then the sample is transferred to the container, wherefrom the signal is read. Preferably, a secondary, labeled binding agent is added in the container to obtain the signal.

In a preferred embodiment appropriate controls are applied. A control for the binding agent includes non-specific binding agents like Ig molecules, like IgG or other non-specific immunoglobulins. In analogy, if other type of binding agents are applied, preferably an analogous non-specific variant.

Alternatively, a binding agent recognizing an other membrane protein present, preferably abundant and/or generally present in the erythrocyte membrane can be applied as a control. Thus, such membrane proteins can be used as control membrane proteins. For example quantitative determination of intracellular or extracellular membrane proteins or antigens in the erythrocyte membrane can serve as control experiments. There are membrane proteins known to be abundantly present in the human erythrocyte membrane, and characterized mostly by antigenic or other binding features in medical diagnostics. As non-limiting examples, Glycophorins, e.g. plasma membrane Glycophorin A protein, agglutinin binding proteins, e.g. the wheat germ agglutinin binding proteins in the human erythrocyte membrane, erythrocyte membrane actin, attached to the intracellular membrane surface, e.g. by specific phalloidin labeling, can be applied as a reference or control marker protein.

The binding agent shall be added in an excess amount to the membrane proteins so as to saturate the epitopes. Expediently, the saturating amount is determined in a separate experiment.

For example, the binding agent is added in different concentrations or amounts to the erythrocyte membrane and specific binding of the binding agent is assessed. Specific binding can be assessed by using an appropriate control. For example, non-specific binding can be shown by an alternative binding agent or a mixture thereof. This binding agent may have a non-specific binding property or may bind to an other protein present in or attached to or associated with the red cell membrane. This protein may even be a non-integral membrane protein. The level of said other protein is preferably known and it is preferably abundant in red cells.

In a flow cytometry experiment, for example, the signal indicating the membrane protein is well separable from the non-specific background.

In a preferred embodiment saturation is assessed by titration with the binding agent. For example, when the increase in the signal correlates with (preferably proportional to) the concentration or amount of the binding agent, the epitopes are still not saturated. Preferably, according to the invention a linear relationship between the membrane protein and the binding agent is provided. Above a certain concentration, amount or level of bingeing agent non-specific binding is increased. In relative terms, i.e. as compared to the number (concentration, amount or level) of binding sites (epitopes or membrane protein) the specific binding is reduced.

Preferably, the binding agent is applied in an experimentally determined multiplicity of the amount saturating the specific binding sites.

In a preferred embodiment small amount of blood samples are taken from the subject. Preferably, the volume of blood sample is less than 20 ml, 10 ml, 5 ml, 1 ml, 500 ul, 300 ul or 100 ul. Highly preferably, the blood sample is less than 80 ul, 60 ul, 50 ul, 40 ul or 30 ul. Still more preferably, the blood sample is between 50 ul and 1 ul or between 40 ul and 5 ul or between 30 ul and 10 ul.

The present invention is further illustrated below by certain embodiments of the assay methods and the membrane proteins of this invention. In addition, we also provide examples for the currently recognized membrane proteins in the human red cell membrane, with a short description of the connected diseases or medical conditions (see the section "Examples for quantitative determination of erythrocyte membrane proteins") to illustrate the range of applications of the invention. It is to be understood that the skilled person is able to find variants of these embodiments provided that he/she is able to arrive at said embodiment based on his/her general knowledge and prior art information on the given technical field.

Assay Systems for Quantitative Determination of Erythrocyte Membrane Proteins

The invention relates to the use of cellular assay systems in which a quantitative determination of the binding of a ligand to the erythrocyte membrane proteins can be performed. It is essential that the membrane proteins are not separated from or purified from the red blood cell membrane but rather is present in said membrane during the assay procedure. Quantitative results can be achieved by the fact that the binding agent is applied in the saturation amount which allows obtaining a signal strictly correlated to the number or amount of the membrane protein given. The application includes, but is not restricted to the flow cytometry and cellular plate assays described below.

The present inventors have found that flow cytometry system provides a platform for determining quantitative membrane protein expression in the erythrocyte membranes by using specific binding reagents (binding agent), preferably specific ligands (e.g. natural ligands, aptamers, etc.) or antibodies, preferably monoclonal antibodies. The binding agent shall be applied at saturating concentrations so that the quantitation of the membrane protein expression can be performed for each required membrane protein. By applying selected binding agents recognizing isoforms or variants of the given membrane protein, the quantitation of these isoforms or variants is also available.

Rapid sample preparation, the application of favorable cell fixation and processing methods disclosed herein allow the selective recognition of membrane protein epitopes on the intracellular or extracellular membrane surface. The assay can be extended to use fresh peripheral venous or capillary blood samples as well as frozen stored and thawed blood samples. The quantitative assay for a given membrane protein related to a specific medical condition or drug treatment can be further improved by the simultaneous application of the determination of an endogenous membrane proteins serving as a reference control. The platform allows a rapid and complex diagnostic application of membrane protein recognition in human red cells.

It is to be understood that the skilled person is aware of assay methods which are analogous and provide an alternative to flow cytometry, wherein whole membranes, preferably whole cells, e.g. intact cell or ghosts comprising the membrane protein expressed by the red cell are studied by a binding agent; or that such methods may be developed in the future. These methods may include single cell quantitative imaging, ligand-specific microscopic staining or other detection methods, so far as it meets the requirement of rapid sample preparation, allow sufficiently strong binding of the binding agent to one or more epitope of the red cell membrane protein, and a fast and quantitative detection of the binding allowing a quantitative assessment of the amount or number of the given red cell membrane protein.

Below examples are provided for these possibilities in this diagnostic platform.

A plate assay format, e.g. a cellular plate assay system provides a further possible platform for determining quantitative membrane protein expression in the erythrocyte membranes by using specific binding reagent or agents, preferably specific ligands (e.g. natural ligands, aptamers, etc.) or antibodies, preferably monoclonal antibodies in multiwell plates or similar or equivalent assay systems. All features and applications described above for the flow cytometry platform are also available in this platform.

Typically, in this assay format a specific binding of the binding agent to the red cell membrane protein present in the red cell membrane is measured.

By using enzyme-linked immuno-assay (ELISA) formats the sensitivity of the assay can be increased and the background strongly decreased. In addition, this assay systems provides the possibility for large capacity diagnostics for selected membrane proteins, that is allows the generation of high-throughput (HTS) applications.

As a preferred example, a rapid, simple and reliable microplate cellular fluorescence-based assay for the quantitative determination of an ABC transporter, preferably a multidrug transporter in human erythrocytes has been developed. The expression level of the membrane protein in the erythrocyte membranes was determined by using specific antibodies. A close correlation between the flow cytometry data and the plate reader results were found. For example, antibody recognition of the ABC transporter protein in blood samples individuals carrying the heterozygous mutations causing premature termination thereof was determined and a significantly lower level of ABC transporter expression was found. Since the red cell number is higher by more than 3 orders of magnitude than any white blood cell in a blood preparation, and the platelets can be removed by simple centrifugation protocols, the isolation of erythrocytes is not necessary to perform these studies. Thus, erythrocyte membrane expression level can be properly detected in microplate, immunosorbant or ELISA assays. Direct determination of erythrocyte membrane protein expression, as a validated biomarkers for personalized diagnostics, is possible in this setting.

In the following sections we provide examples for this platform application in a diagnostic setting.

Examples for Quantitative Determination of Erythrocyte Membrane Proteins

This patent application is related to the quantitative determination of the expression level of an erythrocyte membrane protein. The application includes, but is not restricted to the membrane protein examples described below, which have known medical relevance. Detailed references are provided at the description of detailed examples of this application.

As a highly preferred option, membrane transporters are assayed in the present invention. The membrane transporters may be one or more of the following type: ATP-dependent transporters, e.g. ABC membrane transporters, ATP dependent ion transporters; drug transporters; multidrug transporters; solute carrier (SLC) type transporters; membrane channels.

A preferred embodiment of the invention is the quantitative determination of ABC membrane transporters in the human erythrocyte membrane. ABC membrane transporters have been found to be present in the human erythrocyte membrane but apparently no rapid quantitative determination of their expression level is suggested. The determination of the ABC membrane transporter proteins in the human erythrocyte membrane allows the correlation of protein expression with polymorphic variants or mutations, which are involved in numerous cellular transport functions. As selected examples, ABCB1 (MDR1), ABCC1 (MRP1) and ABCG2 (BCRP/MXR) have been documented to affect the cellular metabolism of numerous toxic agents. Determination of their expression has a predictive value in cancer drug treatment, in ADME-TOX, and is applicable for determining potential efficacy and/or toxicity of drug treatments in diseases. ABCG2 expression has been documented to affect uric acid transport related conditions, e.g. gout development. Determination of the ABCB6 membrane protein in the human erythrocyte membrane has a potential predictive value in the ADME-TOX parameters and in hematological diseases, or related drug treatment. The ABCC4 (MRP4) membrane protein expression level in the human erythrocyte membrane is expected to show correlation with drug and cyclic nucleotide transport, and drug treatment of diseases. Determination of the ABCA1 membrane transporter expression level in the human erythrocyte membrane is expected to correlate with cholesterol transport from cells, lipid-related diseases, treatment of lipid disorders, stroke and atherosclerosis.

A preferred embodiment of the invention is the quantitative determination of ATP-dependent ion transporters in the human erythrocyte membrane but apparently no rapid quantitative determination of their expression level is suggested. These transporters are known to be abundantly present in the human erythrocyte membrane. As selected examples determination of the plasma membrane Na—K ATPase (ATP1A1, ATP1A2) membrane transporter, especially the selected isoforms of the alpha subunits in the human erythrocyte membrane and its correlation with polymorphic variants and mutations, is expected to have a predictive value in migraine and hematological diseases. Determination of the plasma membrane calcium ATPase (ATP2B1-4, PMCA1-4) membrane transporters in the human erythrocyte membrane and its correlation with polymorphic variants and mutations is expected to have a predictive value in complex brain and cardiac diseases, diabetes and oxidative stress-related conditions, hematological diseases and male infertility. These proteins may also serve as a potential standard markers for assay validation.

A preferred embodiment of the invention is the quantitative determination of solute carrier (SLC) type transporters in the human erythrocyte membrane. These transporters are also known to be present in the human erythrocyte membrane but the present inventors have no information on the quantitative determination of their membrane expression level in erythrocyte membranes. As selected examples, the determination of the plasma membrane glucose transporters, GLUT1-4 (SLC2A1-4) in the erythrocyte membrane is expected to have a predictive value in e.g. De Vivo disease, sugar transport in diabetes, obesity, oxidative stress, and drug treatment. Determination of the plasma membrane bicarbonate transporter Band3 (Diego blood group protein, SLC4A1-2), is expected to have a predictive value in malaria resistance, hemolytic diseases, renal tubular acidosis, oxidative stress, and drug treatments. Determination of the plasma membrane Na—Li(H) countertransport proteins (NHE1-4, SLC9A1-4) in the human erythrocyte membrane is expected to have a predictive value in hypertension, psychiatric diseases and drug treatments. Determination of the plasma membrane lactate and piruvate transporter protein (SLC16A1 MCT1, HHF7) in the human erythrocyte membrane is expected to have a predictive value in hyperinsulinemic hypoglycemia, diabetes, and drug treatments. Determination of the uric acid transporter protein (SLC2A9) is expected to have a predictive value in uric acid related conditions, gout, kidney stones, diabetes, and drug treatments. Expression level of the erythrocyte membrane urea transporter protein (SLC14A1-2, Kidd blood group protein) is expected to have a predictive value in diseases of protein metabolism. The expression level of the SLC42A1 ammonia transporter protein (RHAG blood group, CD241) is expected to be involved in several diseases related to ammonia transport. The expression of organic anion (SLCO) and organic cation (SLC22A) exchange transporters are currently not well characterized but the determination of these membrane transporters in the erythrocytes is expected to have a predictive value in drug and xenobiotics ADME-Tox parameters.

A preferred embodiment of the invention is the quantitative determination of membrane channels in the human erythrocyte membrane. A number of plasma membrane ion channels are known to be present in the human erythrocyte membrane, however, the present inventors have not found a specific report on their rapid quantitative determination in that membrane. Quantitative determination of the plasma membrane calcium-induced potassion channel (KCNN4, Intermediate conductance calcium-activated potassium channel protein 4, Gardos Channel) is expected to have a predictive value in cell survival (shrinkage, loss of KCl and water) and in sickle cell anemia treatment. Quantitative determination of the erythrocyte membrane aquaporins (AQP-1, Aquaporin CHIP, MIP, AQPO, Colton blood group, and AQP3, GIL blood group), responsible for rapid water and organic ion transport in many tissues, are expected to have predictive values in kidney diseases. The expression of other complex ion channels (e.g. SUR, ABCC8-9 type ion channels) in the erythrocyte membrane is currently unexplored, but may have predictive value in diabetes and other metabolic diseases, as well as in drug responses.

As a further preferred option, membrane receptors are assayed in the present invention.

A preferred embodiment of the invention is the Quantitative determination of transmembrane receptors in the human erythrocyte membrane. A number of plasma membrane receptors are known to be present in the human erythrocyte membrane, however, the present inventors have not found a specific report on their rapid quantitative determination in that membrane. Determination of the plasma membrane insulin receptor protein in the human erythrocyte membrane is expected to have a predictive value in the development and treatment of diabetes and related conditions. Determination of the plasma membrane beta adrenergic receptor protein in the human erythrocyte membrane is expected to have a predictive value in the treatment and development of malaria, allergic reactions, and in various other drug treatments. Reports indicate the presence of angiotensin receptors, LPA receptors, glycocorticoid receptors, and endothelin receptors in the red cell membrane, and their quantitative determination is expected to have a predictive value in complex diseases including hypertension, diabetes, or stroke.

A further embodiment of the invention is the quantitative determination of characteristic intracellular and extracellular membrane proteins and antigens in the human erythrocyte membrane. There are membrane proteins known to be abundantly present in the human erythrocyte membrane, and characterized mostly by antigenic or other binding features in medical diagnostics. These proteins may also be applied preferably as controls in the assays of the present invention. Specifically, determination of the plasma membrane Glycophorin A protein and in general, the wheat germ agglutinin binding proteins in the human erythrocyte membrane may serve as reference markers. Similarly, the determination of erythrocyte membrane actin, attached to the intracellular membrane surface, e.g. by specific phalloidin labeling, can be applied as a reference protein. Determination of the Flotillin 1-2 proteins is expected to have a predictive value in the development and therapy of diabetes, the basal cell adhesion molecule (BCAM, CD239, Lutheran blood group, receptor for laminin) may be predictive in epithelial cell cancer development and in vaso-occlusion in sickle cell disease, and the CD151 tetraspanin glycoprotein (RAPH/MER2 blood group) may also modulate cell adhesion, metastasis and tumor development. Basigin (CD147, OK blood group protein) has a key role as a receptor for malaria parasites, and modulates various immunological functions, thus its quantitation may provide valuable information related to various diseases. Direct and quantitative determination of rare blood group antigens represented by membrane glyco-proteins (e.g. the Kell, Dombrock, Duffy or Kidd antigens) may significantly help the development of transfusion and related therapies and the prevention of intrautherine fetal diseases (for details see the Blood Group Antigen Gene Mutation Database [Blumenfeld O O, Patnaik S K. Allelic genes of blood group antigens: a source of human mutations and cSNPs documented in the Blood Group Antigen Gene Mutation Database. Human Mutation. 2004 January; 23(1):8-16.] and the Blood Group Antigen Gene Mutation Database: http://www.ncbi.nlm.nih.gov/projects/gv/rbc/xslcgi.fcgi?cmd=bgmut/systems).

In accordance with the Examples and the teaching above several additional membrane proteins have been experimentally shown and quantitatively measured in the erythrocyte membrane. The results are shown in Table 1.

TABLE 1

List of membrane proteins detected in red blood cells, in addition to the specific examples presented, by specific monoclonal antibodies

| Symbols | Name | Maximum binding level + |
|---|---|---|
| ABCB11, BSEP | Bile Salt Export Pump | 2-3 |
| CD55, DAF | Cromer blood group | 50-60 |
| CD220, INSR | insulin receptor | 30-35 |
| CLIC3 | chloride intracellular channel 3 | 8-10 |
| INSRR | insulin receptor-related receptor | 50-60 |
| KCNN4 | potassium intermediate/small conductance calcium-activated channel, subfamily N, member 4, Gardos-channel | 7-9 |
| SLCO1A2, OATP1A2 | Solute carrier organic anion transporter family member 1A2 | 4-4.5 |
| SLCO2B1, OATP2B1 | Solute carrier organic anion transporter family member 2B1 | 7-8 |
| SLCO4A1, OATP4A1 | Solute carrier organic anion transporter family member 4A1 | 5-6 |
| SLC2A1, GLUT1 | solute carrier family 2 (facilitated glucose transporter), member 1 | 180-280 |
| SLC2A3, GLUT3 | solute carrier family 2 (facilitated glucose transporter), member 3 | 5-6 |
| SLC5A1, SGLT2 | Solute carrier family 5 (sodium/glucose cotransporter), member 1 | 12-16 |
| SLC5A2 | solute carrier family 5 (sodium/glucose cotransporter), member 2 | 25-30 |
| SLC6A14 | solute carrier family 6 (amino acid transporter), member 14 | 3-4 |
| SLC7A5 | solute carrier family 7 (amino acid transporter light chain, L system), member 5 | 3-4 |
| SLC9A1 | solute carrier family 9, subfamily A (NHE1, cation proton antiporter 1), member 1 | 7-8 |
| SLC10A1, NTCP | Na+-taurocholate cotransporting polypeptide | 2-3 |
| SLC14A1 | Solute carrier family 14 (urea transporter), member 1 (Kidd blood group) | 6-7 |
| SLC19A2 | solute carrier family 19 member 2 | 3-4 |
| SLC22A12, URAT1 | Solute carrier family 22 (organic anion/cation transporter), member 12 | 30-40 |
| SLC22A19, OAT5 | Organic anion transporter 5 | 4-5 |
| PIP4K2A | Phosphatidylinositol 5-phosphate 4-kinase type-2 alpha | 4-5 |
| PLSCR1 | phospholipid scramblase 1 | 15-20 |

+expressed as a ratio of specific antibody binding/isotype control

In a preferred embodiment the expression levels of the various ABC proteins in the erythrocyte membranes were determined by using specific monoclonal antibodies. Samples were obtained either from peripheral venous or capillary (finger-tip) blood. Thus, it has been proven that a very small amount of blood sample is sufficient. We found well measurable quantities for all the investigated human ABC transporters in the erythrocyte membrane. These results suggest that a direct determination of the erythrocyte membrane ABC protein expression, as a validated biomarkers for personalized diagnostics, is possible.

In preferred embodiments multiple proteins are measured simultaneously. In a preferred embodiment an integral membrane protein and a control protein is measured simultaneously. In a further preferred embodiments multiple integral membrane proteins are measured simultaneously, optionally in aliquots from the same blood sample (e.g. in plate format assays). Alternatively, multiple integral membrane proteins are measured with different binding agents in the same test sample (e.g. in a whole cell assay format or in a liquid phase format, e.g. in a flow cytometer assay).

In a particularly preferred embodiment of the invention a rapid, simple and reliable flow cytometry assay for the quantitative determination of ABC transporters in the human erythrocyte membrane is performed. The method has surprisingly revealed significant differences between the expression levels of a wild-type ABC transporter protein, ABCG2, and its heterozygous (Q141K) polymorphic variant. Moreover, individuals carrying mutations on one allele, causing premature termination of ABCG2 synthesis, have a 50% reduction in the erythrocyte expression of this protein.

Polymorphisms modify patient condition, e.g. essential pharmacokinetic parameters, for example, in the case of ABCG2, uric acid metabolism and cancer drug resistance. Therefore, a direct determination of the erythrocyte membrane ABCG2 protein expression provides valuable tool for assessing these conditions or for devising drug treatments. The present findings show that erythrocyte membrane protein levels reflect genotype-dependent overall tissue expression patterns.

In a variant of this method, the assay was adapted to human frozen stored blood samples. In particular, a flow cytometry was developed for the quantitative determination of an ABC transporter, the ABCG2 multidrug transporter in human frozen stored blood samples. Samples were obtained either from peripheral blood or bone marrow aspirates and stored at −20-80° C. for various time periods (one week to 5 years) The expression level of the protein in the erythrocyte membranes was determined by using specific antibodies. Similarly to that seen in freshly drawn blood cell samples, significant differences were found between the expression levels of the wild-type ABCG2 protein, the heterozygous Q141K polymorphic variants, or mutants with premature termination. Thus, fast and reliable quantitative determination of erythrocyte membrane protein expression is possible in frozen stored blood samples. This allows retrospective analysis, useful in patient monitoring, personalized diagnostics, and evaluation of the biological effect of drugs.

In a preferred embodiment patient samples were analyzed and found that whereas a part of the patients showed reduced expression of an ABC transporter the erythrocyte membrane expression of said ABC transporter was significantly up-regulated after long-term treatment with a drug treating the disease condition concerned. The assay of the invention is appropriate to follow dynamic, time-dependent alterations in membrane protein expression. A direct determination of the erythrocyte membrane protein expression, in particular ABC transporter expression, allows for a long period of patient observation or treatment. The membrane proteins in the context of the invention are useful e.g. as a validated biomarkers for diagnostics. In a preferred example the patients are hematological patients and/or cancer patients. The method for a quantitative determination of the membrane level, in particular of an ABC transporter allows a personalized approach in pharmacology. Highly preferably, an ABC transporter responsible for ADME-Tox properties and drug sensitivity is assayed. In an embodiment, the ABC transporter is a multidrug transporter, e.g. ABCG2.

In an exemplary method frozen-thawed blood samples of hematological patients with chronic granulomatous leukemia (CLL) were assayed. The samples were taken either at the onset of disease or during anticancer drug treatment. Altogether 300 blood samples were analysed and about 60 patients with the heterozygous ABCG2-Q141K polymorphism and 3 patients with ABCG2 genes homozygous for Q141K were found. Results indicate that the patients homozygous for the Q141K had significantly lower ABCG2 expression in their erythrocyte membranes, while drug treatment greatly increased ABCG2 expression, as the leverl significantly upregulated after long-term treatment with the drug Imatinib mesylate (Glivec).

These results further indicate the applicability of the erythrocyte membrane expression level as a diagnostic biomarker and allow retrospective studies.

In further embodiments, the ABC transporter is a transporter of the ABCA, ABCB, ABCC, ABCD, ABCE, ABCF or ABCG families. In the present example, the quantitative measurement of the following ABC transporters are exemplified below: ABCB1 (MDR1), ABCC1, ABCC4, ABCA1, and ABCC3.

In a further embodiment, the membrane expression levels of two or more ABC transporters are measured together. In an example, we found an inverse expression level of the ABCG2 and the ABCB1 proteins, suggesting an up-regulation of ABCB1 expression in subjects expressing low levels of ABCG2.

Moreover, plasma membrane CaATPases (PMCA) transporter proteins in human erythrocytes were determined. Samples again were obtained either from peripheral venous or capillary (finger-tip) blood. The expression levels of the PMCA isoforms in the erythrocyte membranes were determined by using specific monoclonal antibodies. We found well measurable quantities of the PMCA transporter, including PMCA4, especially the PMCA4b isoform, in the erythrocyte membrane. These results suggest that the methods of the invention allow a direct, quantitative determination of the erythrocyte membrane PMCA protein expression, including its isoforms, as validated biomarkers for personalized diagnostics.

According to an embodiment, an assay for the quantitative determination of membrane attached intracellular and extracellular proteins in human erythrocytes was applied. Samples were obtained either from peripheral venous or capillary (finger-tip) blood. The expression of known intracellular and extracellular proteins in the erythrocyte membranes were determined by using specific ligands. In the erythrocyte membrane a well measurable quantities of actin was shown, when using its specific ligand, phalloidin. Moreover, determination of extracellular lectin binding proteins, specifically wheat germ agglutinin binding proteins in the human erythrocyte membrane by using fluorescent wheat-germ agglutinin preparations was shown herein. These results suggest that a quantitative determination of these erythrocyte membrane proteins may help to obtain validated biomarkers for personalized diagnostics and in particular they may serve as appropriate reference or control protein.

Below certain specific an non-limiting examples are provided to illustrate the present invention.

EXAMPLES

Example 1

Flow Cytometry Based Quantitative Determination of the ABCG2 (BCRP, MXR) Membrane Protein in Freshly Drawn Peripheral Blood Erythrocyte Membranes by Using Monoclonal Antibodies—Correlation with Polymorphic Variants and Mutations—Parallel Determination of the Plasma Membrane Calcium Pump Protein (PMCA) and Glycophorin A in the Erythrocyte Membrane by Using Monoclonal Antibodies The ABCG2 multidrug transporter is preferentially expressed in pharmacological barriers, in the liver, kidney and stem cells. This protein modulates the absorption, metabolism and toxicity of numerous drugs and xenobiotics, and causes multidrug resistance in cancer [for reviews see Allen J D and Schinkel A H. Mol Cancer Ther. 2002(1): 427-434; Krishnamurthy P and Schuetz J D. Annu Rev Pharmacol Toxicol. 2006(46):381-410; Sarkadi B et al. Physiol Rev. 2006(86):1179-1236; Szakacs G et al. Drug Discov Today. 2008(13):379-393. Imai Y et al. Mol Cancer Ther. 2002(1):611-616]. Polymorphic variants or nonsense mutations of ABCG2 were found to be associated with interindividual variability in drug response to anticancer chemotherapy and the outcome of psoriasis or multiplex sclerosis treatments [Imai Y et al. Mol Cancer Ther. 2002 (1):611-616; Sparreboom A et al. Clin Pharmacol Ther. 2004(76):38-44, Gardner E R et al. Clin Pharmacol Ther. 2006(80):192-201; Akasaka K et al., Cancer Chemother Pharmacol. 2010(66):691-698]. Recently, a significant disease-association for an ABCG2 variant (Q141K) has been observed in gout (Matsuo H et al., Sci Transl Med. 2009 (1):5ra11; Yang Q et al., Circ Cardiovasc Genet. 2010(3): 523-530; Robey R W et al., Curr Pharm Biotechnol. 2011 (12):595-608; Morisaki K et al. Cancer Chemother Pharmacol. 2005(56):161-172; Ichida K. et al, Nature Communications, Apr. 3, 2012, DOI: 10.1038/ncomms1756].

Since membrane proteins undergo complex processing and trafficking, mRNA levels in many cases do not correspond to the final protein expression in the target membrane. In addition, mutations and polymorphisms may cause mis-trafficking and early degradation that may contribute to decreased protein expression. This is well documented in the case of the ABCG2-Q141K variant, which shows lower membrane protein expression in model cells despite unchanged mRNA levels [Robey R W et al. Curr Pharm Biotechnol. 2011(12):595-608; Morisaki K et al., Cancer Chemother Pharmacol. 2005(56):161-172; Furukawa T et al., Pharm Res. 2009(26):469-479]. Lower expression of ABCG2-Q141K has not been confirmed at physiologically relevant sites, given the difficulties in obtaining and processing human tissues. Recently, two papers have been published linking the blood group Jun to ABCG2 [Saison C et al. Nat Genet. 2012; 44:174-177; Zelinski T et al. Nat Genet. 2012; 44:131-132]. Since the erythrocytes contain functional ABCG2 [Maliepaard M et al. Cancer Res. 2001 (61):3458-3464; de Wolf C J et al. Febs J. 2007(274):439-450; Leimanis M L and Georges E. 2007(354):345-350.], we examined if red cell membrane ABCG2 protein levels correlate with polymorphisms that are known to influence protein expression.

Methods

Anticoagulated blood samples of healthy volunteers were fixed in paraformaldehyde (PFA), stained with monoclonal antibodies recognizing human ABCG2, and subjected to flow cytometry (FACS). In parallel, genomic DNA was isolated from the blood samples; common SNPs of the ABCG2 gene were screened by quantitative PCR, while mutations were determined by direct sequencing. Blood was obtained from healthy volunteers, and all subjects gave their written informed consent to participate in the study. This study was approved by the regional ethical committees, and all procedures were performed in accordance with the Declaration of Helsinki.

Flow Cytometry:

Unrelated, apparently healthy volunteers without any acute or chronic disorders requiring medical treatment participated in the study. For the flow cytometry studies freshly drawn human blood by using EDTA to prevent coagulation (25 uL) was diluted in 4 mL of phosphate buffered saline (PBS) containing 1% paraformaldehyde (PFA) and fixed for 60 min at 25° C., then antibody staining was performed in the fixed samples with specific monoclonal antibodies recognizing various membrane proteins. In preliminary experiments we have analyzed the effects of various PFA concentrations (0.5-4%), phosphate or Tris buffer concentrations, fixation periods (10-120 min) and fixation temperatures (4-37° C.), and found the above conditions allowing optimum formation of mixed intact red cell/ghost populations as well as antibody recognition.

After fixation the cells were centrifuged with 3,000×g for 10 min and the pellet resuspended in 100 uL PBS. Antibody staining was performed for 40 min at 37° C. by using the BXP34 and the BXP21 (generated by G. Scheffer [Scheffer G L, et al. *Cancer Res.* 2000(60):2589-2593], the 5D3 (BD-Pharmingen 562167) monoclonal antibodies specific for ABCG2, or the respective IgG control antibodies (IgG1: Invitrogen, MG100, IgG2a: Invitrogen, MG2A00, IgG2b: Invitrogen, MG2B00). It should be noted that BXP21 can also be used in the Western blots (see FIG. 27), while the BXP34 mAb does not recognize ABCG2 on Western blots but specifically interacts with the protein in tissue preparations [Diestra J E, et al. *J Pathol.* 2002(198):213-219]. For staining red cell membrane PMCA we have used the 5F10 monoclonal antibody (ABCAM, Ab2825), recognizing all 4 human PMCA isoforms [Caride A J, et al. Biochem J. 1996 316 (Pt 1):353-359].

After washing out the primary antibodies, secondary antibodies corresponding to the IgG type and labeled with phycoerythrin (PE) were added to the cells (Anti-mouse IgG1-PE: Invitrogen P21129, anti-mouse IgG2a-PE: Invitrogen P21139, anti-mouse IgG2b-PE: Invitrogen, P21149), incubated for 30 min at 37° C., washed and resuspended in PBS. In parallel tubes cells were directly stained with FITC-conjugated anti-Glycophorin A monoclonal antibody (Gly-A-FITC: Beckman Coulter, 2212).

Intact red cells and erythrocyte ghost were gated out based on the forward scatter (FSC) and side scatter (SSC) parameters. Both fractions were analyzed for antibody staining by a FACSCalibur flow cytometer (excitation wavelength: 488 nm (Argon ion laser) emission filters: 585/42 nm for PE, 530/30 for FITC). Under these conditions other blood cell types than erythrocytes are not visible for the flow cytometry because of their much lower abundance and the fixation conditions applied. A careful optimization for maximum antibody labeling was carried out for all monoclonal antibodies. After antibody titration all the relevant monoclonal antibodies were applied in concentrations exceeding maximum binding levels. In additional control experiments we have used rat red cells to analyze the specificity of the anti-ABCG2 antibodies applied. We found that the human-specific 5D3 antibody did not recognize ABCG2 in either intact or lysed rat red cells, while the other mAbs were not human specific.

Calculations

In order to use a combination of all relevant anti-ABCG2 antibodies for quantitating ABCG2 expression in the red cell membranes, we have calculated an avarage binding factor, based on the relative staining efficiencies observed. In all experiments BXP34 gave 3 times greater relative staining than either the BXP21 or the 5D3 antibodies (the exact epipotopes and the potential multiplicity of mAb binding are unknown), therefore in the calculated ABCG2 factor we used the following equation:

$$((BXP34/3)+BXP21+5D3)/3. \quad (i)$$

As documented in FIG. 4, a linear correlation between the weighted average binding of the to mAbs, BXP34 and BXP21, recognizing intracellular epitopes, and the binding of the cell-surface reactive, human-specific 5D3 mAb binding was observed.

Genetic Analysis:

For ABCG2 polymorphism and mutation studies genomic DNA was isolated from EDTA anticoagulated peripheral blood by Gentra Purege Blood Kit (Quiagen, Hamburg, Germany). The most common SNPs in ABCG2 [V12M (c.34G>A, p.12Val>Met in exon 2, SNP database ID: rs2231137) and Q141K (c.421C>A, p.141Gln>Lys in exon 5, SNP database ID: rs2231142] were genotyped using the LightCycler480 (Roche Diagnostics, Basle, Switzerland) allelic discrimination system as described previously in detail [Fischer S et al. Scand J Gastroenterol. 2007; 42:726-733.]. Sanger sequencing of the ABCG2 coding region and exon-intron boundaries (exons 2-16) was performed by Applied Biosystems 310 Genetic Analyzer (Life Technologies, Carlsbad, USA).

Western Blotting:

Membrane protein preparation of human red cells and Sf9 cells, expressing human ABCG2 protein was performed as described in [Özvegy C et al. J Biol Chem. 2002; 277: 47980-47990; Telbisz A et al. Biochim Biophys Acta. 2007; 1768:2698-2713.]. K562 cells were retrovirally transduced to express ABCG2 as describen in [Hegedüs C et al. Br J Pharmacol. 2009:1153-64. PMID: 19785662]. Membrane proteins were separated on 7.5% Laemmli-type SDS gel electrophoresis and electroblotted to PVDF membranes [Ichida K et al. Nature Communications, Apr. 3, 2012, DOI: 10.1038/ncomms1756].

Results and Discussion

We have established a whole cell based assay for the quantitative determination of ABCG2 expression in blood samples. If performed by FACS, the forward/side scatter plot delineates two major populations, corresponding to PFA-fixed erythrocytes and erythrocyte membrane "ghosts" (FIG. 1). Antibodies recognizing intracellular epitopes of ABCG2 bind to ghosts that are accessible from both sides of the membrane (FIG. 1B-C) [Scheffer G L et al. Cancer Res. 2000(60):2589-2593; Diestra J E et al. J Pathol. 2002(198): 213-219]. Conversely, the 5D3 monoclonal antibody, recognizing an extracellular epitope of the ABCG2 protein shows binding to PFA-fixed cells as well (FIG. 1D) [Özvegy-Laczka C et al. *J Biol Chem.* 2008(283):26059-26070]. This membrane orientation was confirmed using antibodies recognizing an extracellular Glycophorin A epitope (FIG. 1E), or the human plasma membrane calcium ATPase protein (PMCA, [Caride A J et al. Biochem J. 1996 (316 (Pt 1)):353-359.]).

As documented in FIG. 1, all three antibodies detect significant expression of ABCG2 in erythrocytes. In order to allow quantitative protein determination, we titrated the antibodies to obtain maximum binding. Under these conditions, the three anti-ABCG2 antibodies yielded consistent results that were expressed as the "RBC-G2 factor" or "Erythrocyte ABCG2 factor".

Next, we quantified the expression of erythrocyte ABCG2 in 47 unrelated, healthy individuals that were also screened for the presence of two prevalent ABCG2 polymorphic variants found in the Caucasian population (V12M and Q141K) (see Imai Y et al. Mol Cancer Ther. 2002(1):611-616; Sparreboom A et al. Clin Pharmacol Ther. 2004(76): 38-44; Gardner E R, Clin Pharmacol Ther. 2006(80):192-201; Akasaka K et al. Cancer Chemother Pharmacol. 2010 (66):691-698]. Significant ABCG2 levels, encompassing a wide range of expression were detected in the red blood cells of all individuals. Differences of the erythrocyte ABCG2 expression could not be attributed to age or sex. However, when the samples were grouped according to their genotypes, we found that the red blood cells of individuals carrying the heterozygous Q141K variant exhibited significantly lower expression of ABCG2 ($5.27\pm1.19$), as compared to homozygous wild-type individuals ($6.13\pm0.61$, $p=0.011$) (FIG. 2). There was no significant difference between the individuals carrying the wt ABCG2 or the V12M variant, although the number of the carriers of this variant was relatively low.

Interestingly, we found two individuals showing much lower (about 50%) erythrocyte ABCG2 expression ($2.65\pm0.29$) (FIG. 2/A). Sequencing of the entire ABCG2 gene revealed that these individuals carry heterozygous mutations resulting in premature termination (c.706C>T, R236X; and c.791_792delTT resulting in L264fsX13). In order to clarify if a direct relationship exists between the heterozygous stop mutations and the erythrocyte ABCG2 expression levels, we obtained blood samples from the family members of the donors carrying these stop mutations. As shown in FIG. 2B, we found a co-segregation of the reduced erythrocyte ABCG2 expression levels (about 50% reduction) and the respective mutations in the two families. These findings show a direct correlation between ABCG2 variants and erythrocyte membrane expression, and indicate a general bi-allelic expression pattern for ABCG2, as has been suggested based on mRNA data [Kobayashi D et al., Drug Metab Dispos. 2005(33):94-101].

In order to document the expression of ABCG2 in the red cell membrane and compare the expression levels to those in known expression systems, we have performed Western blot experiments by using isolated red cell membranes, isolated Sf9 insect cell membranes expressing the human ABCG2 protein, and A431 cells overexpressing ABCG2 [Szakacs G et al. Drug Discov Today. 2008(13):379-393; Imai Y et al. Mol Cancer Ther. 2002(1):611-616.]. As shown in FIG. 3, in accordance with previous data in the literature, [Sparreboom A et al. Clin Pharmacol Ther. 2004(76):38-44; Gardner E R et al, Clin Pharmacol Ther. 2006(80):192-201; Akasaka K et al. Cancer Chemother Pharmacol. 2010(66):691-698.] we could detect both the monomeric and dimeric forms of ABCG2 in the red cell membrane. Based on several similar blots and comparing ABCG2 expression in the Sf9 membranes (The ABCG2 protein corresponding to about 4% of total membrane proteins), and ABCG2 expression in the red cell membranes, we calculated an expression between 1-2,000 copies of ABCG2 in normal human erythrocytes.

In the flow cytometry experiments for all ABCG2 measurements we successfully used three monoclonal antibodies (BXP34, BXP21, and 5D3) and found a close correspondence among the relative expression of ABCG2 reported by the three antibodies. In order to obtain an average value for ABCG2 expression we used a weighted average, in which the BXP34 values were divided by 3 (see Methods). As documented in FIG. 4, a linear correlation between the calculated ABCG2 factor and the cell-surface reactive, human-specific 5D3 binding was observed.

In order to analyze the relative quantitative expression of membrane proteins, we have examined antibody recognition of several membrane bound red cell proteins. As an example, we document here the compared quantitative expression patterns of the calcium pump protein, PMCA, the Glycophorin A protein, and the ABCG2 protein in a family examined for genetic variations (FIG. 5). The 5F10 monoclonal antibody applied here recognizes all four PMCA isoforms, containing a common epitope [see Caride et al, (1996) and Krishnamurthy P and Schuetz J D. Annu Rev Pharmacol Toxicol. 2006(46):381-410]. As shown, while the pattern of ABCG2 expression showed significant differences corresponding to the presence of a heterozygous stop mutation (labeled as +/−), the PMCA or GlyA expression levels, although with some variations, were independent of the ABCG2 expression levels.

Regarding the ABCG2 genetic data, among the 47 donors we found 11 individuals with the heterozygous presence of the DNA sequence coding for the Q141K variant (23.4%), and 3 individuals with the heterozygous presence of the V12M variant (2.7%). These results correspond to the generally found polymorhisms distributions in the European populations (see Sarkadi B et al. Physiol Rev. 2006(86): 1179-1236). The nonsense mutation, causing an arginine to stop codon change at codon 236 in exon 7 (c.706C>T, p.R236X, rs140207606) [Akasaka K et al. *Cancer Chemother Pharmacol.* 2010(66):691-698; Matsuo H et al. *Sci Transl Med.* 2009(1):5ra11.] was found in heterozygous form in family 1. A small deletion (c.791_792delTT, L264HfsX13), described in the most recent paper by Saison et al, 2012 [Akasaka K et al. *Cancer Chemother Pharmacol.* 2010(66):691-698.], causing frameshift and the truncation of the protein after the next 14 amino acids, was found in family 2.

As a summary, we have developed a simple and reliable flow cytometry assay to quantitate the expression of the human ABCG2 protein in erythrocytes, and found a close correlation between protein expression and the ABCG2 genotype. Since erythrocyte ABCG2 levels reflect overall tissue expression patterns, the FACS-based method presented here may provide the basis of a membrane protein based biomarker. A quantitative measure of the expression of ABCG2, shaping ADME-Tox properties and drug sensitivity, should significantly promote a personalized approach in pharmacology. A study to evaluate time-dependent alterations of ABCG2 expression in the red cells of hematological patients, in the context of environmental factors or drug treatment is underway.

Personalized medicine requires the development of biomarker diagnostic assays, reflecting individual variations and thus allowing tailored therapeutic interventions. Membrane proteins play a key role in numerous human pathological conditions, while currently no simple assays are available for their quantitation. Human erythrocytes express numerous integral membrane proteins, including various transporters, receptors and membrane proteins with confirmed involvement in human diseases [Pasini E M et al. Blood. 2006(108):791-801.

Alexandre B M. Expert Rev Proteomics. 2010(7):165-168]. The availability of blood samples and a simple and rapid, quantitative membrane protein assay platform could make the erythrocyte membrane widely applicable for biomarker analysis.

Example 2

Flow Cytometry Based Quantitative Determination of the ABCG2 (BCRP, MXR) Erythrocyte Membrane Protein in Frozen Stored Human Peripheral Blood and Bone Marrow Aspirates by Using Monoclonal Antibodies—Correlation with Polymorphic Variants and Mutations. Retrospective Analysis of the Effect of Medical Treatment on ABCG2 Expression in Blood Samples of Hematological Patients The ABCG2 protein has been reported to be present and functional in the erythrocyte membrane [de Wolf C J et al. Febs J. 2007(274):439-450; Leimanis M L and Georges E Biochem Biophys Res Commun. 2007(354):345-350; Özvegy-Laczka C et al. J Biol Chem. 2008(283):26059-26070.].

Humans carrying polymorphic variants or mutations with premature termination of the ABCG2 gene were found to differently handle xenobiotics and cytotoxic agents. Moreover, chemotherapy outcome during cancer, psoriasis or multiple sclerosis treatments correlated with ABCG2-SNPs [Sparreboom A et al. Clin Pharmacol Ther. 2004(76):38-44; Gardner E R et al., Clin Pharmacol Ther. 2006(80):192-201; Akasaka K et al. Cancer Chemother Pharmacol. 2010(66): 691-698; Matsuo H et al. Sci Transl Med. 2009(1):5ra11].

In addition, treatment of hematological malignancies with cytotoxic or targeted anticancer drugs has been documented to increase ABCG2 expression (see Bram E E et al. Neoplasia 2009; 11(12):1359-70; Calcagno A M et al. Br J Cancer 2008; 98(9):1515-24). These are probably due to epigenetic alterations, rapidly inducing the expression of ABC multidrug transporters. Chronic imatinib treatment has been reported to induce the expression of the ABCG2 protein in the leukemic and colon adenocarcinoma cells [Szatmári I et al. J Biol Chem 2006; 281(33):23812-23; Tan K P et al. Mol Pharmacol 2010; 78(2):175-85].

In Example 1 we have worked out a quantitative assay for the red cell membrane ABCG2 protein and documented a correlation of ABCG2 transporter expression with genetic variations. In the present work we examined if a similar quantitative determination of the erythrocyte membrane ABCG2 protein expression can be performed from frozen blood samples, either of peripheral blood or of bone marrow aspirate origin.

Methods

For the membrane protein assays in flow cytometry, frozen peripheral blood or bone marrow aspirate samples of healthy volunteers and hematological patients drawn into EDTA as an anticoagulant were stored at −20° C. for more than 2 weeks. 25 ul of the thawed blood samples were fixed in paraformaldehyde (PFA), then antibody staining was performed by using specific monoclonal antibodies recognizing human ABCG2. In preliminary experiments we determined that a maximum mAb binding under these conditions could be obtained if 0.1% saponin was added to the samples during antibody binding.

Similarly to our previous experiments, for a flow cytometry assay to quantitate ABCG2 expression in the erythrocyte membrane we have used three ABCG2-specific monoclonal antibodies. Weighted average of the three mAbs was calculated based on the previously found ratio of their maximum binding capacity, that is BXP34 showing 3× higher relative binding values.

In parallel, genomic DNA was isolated from the blood samples and common SNPs in ABCG2 were detected by quantitative PCR, while mutations were determined by direct sequencing (for detailed Methods see Example 1).

Results and Discussion

Under the applied assay conditions, all the frozen-thawed erythrocytes became permeabilized as detected from the forward/side scatter view in flow cytometry (see peripheral blood and bone marrow samples FIGS. 6 and 7, respectively). We determined that these cells corresponded to erythrocyte membrane "ghosts", accessible from both sides of the membrane. This open membrane configuration, further assured by the presence of saponin during mAb binding, has been ascertained by using antibodies against known protein epitopes. The anti-Glycophorin A mAb, recognizing an extracellular epitope, and all three anti-ABCG2 antibodies, recognizing either intracellular (BXP34 and BXP21) or extracellular epitopes (5D3) provided similar binding levels in this cell population (FIG. 6B).

As documented in FIGS. 6B and 7B, in these cells all three anti-ABCG2 antibodies gave a clear recognition of the ABCG2 protein, well separable from the control IgG background. In order to allow quantitative protein determination, antibody titration was applied to obtain maximum binding for all mAbs applied, and a linear relationship between ABCG2 levels reported by the three mAbs was found (FIG. 8B).

After establishing the specific and reliable antibody recognition of the ABCG2 protein in the frozen-thawed erythrocyte membranes, we performed comparative studies in the samples of the 47 unrelated, healthy participants, as described in Example 1. In parallel experiments we have carried out the DNA-based genetic determination of the two major (in Europe the most frequent) polymorphic variants (V12M and Q141K) of the ABCG2 gene [see Sparreboom A et al. Clin Pharmacol Ther. 2004(76):38-44; Gardner E R et al. Clin Pharmacol Ther. 2006(80):192-201; Akasaka K et al. Cancer Chemother Pharmacol. 2010(66):691-698; Matsuo H et al. Sci Transl Med. 2009(1):5ra11].

When the level of erythrocyte ABCG2 protein expression was correlated with the coding variants (FIG. 8A), surprisingly a significant, about 20% lower expression in individuals carrying the heterozygous Q141K variant (3.84±0.53) was found, as compared to homozygous wild-type individuals (5.38±1.35, p=0.000014). Similarly to previous results, there was no significant difference between the individuals carrying the wt ABCG2 and the V12M variant, although in this case the number of carriers was relatively low. No significant differences between ABCG2 expression related to the age or sex of the donors was found.

We have also repeated the erythrocyte membrane ABCG2 measurements in frozen-thawed samples in a family carrying the heterozygous mutations causing premature termination of the ABCG2 gene (c.706C>T, R236X—see Example 1). Similarly to that observed in the fresh blood samples, we could properly distinguish the low level ABCG2 expression in the samples of donors carrying the stop mutations (see FIG. 8A).

In preliminary, currently extended studies we have examined frozen-thawed blood samples of hematological patients with chronic granulomatous leukemia (CLL). The samples were taken either at the onset of disease or during anticancer drug treatment. We have analyzed 300 blood samples and found about 60 patients with the heterozygous ABCG2-Q141K polymorphism and 3 patients with ABCG2 genes homozygous for Q141K. Preliminary results indicate that the patients homozygous for the Q141K had significantly lower ABCG2 expression in their erythrocyte membranes, while drug treatment greatly increased ABCG2 expression.

As a summary, we document that erythrocyte membrane expression level of the ABCG2 multidrug transporter can be properly performed in frozen stored blood samples. These results further indicate the applicability of the erythrocyte ABCG2 level as a diagnostic biomarker and allow retrospective studies. Moreover, the same type of assay is appropriate to follow dynamic, time-dependent alterations in ABCG2 protein expression. This extended method for a quantitative determination of the membrane level of the ABCG2 protein, responsible for ADME-Tox properties and drug sensitivity, allows a personalized approach in pharmacology.

Example 3

Microplate-Based Quantitative Determination of the ABCG2 (BCRP, MXR) Membrane Protein in the Human Erythrocyte Membrane by Using Monoclonal Antibodies The ABCG2 protein has been reported to be present and functional in the erythrocyte membrane. In Example 1 of this application we have worked out a quantitative assay for the red cell membrane ABCG2 protein and documented a correlation of ABCG2 transporter expression with genetic variations. In the present work we examined if a similar quantitative determination of the erythrocyte membrane ABCG2 protein expression can be performed in microplate-based fluorescence assays.

Methods

Erythrocytes were labeled by anti-ABCG2 mAbs as described in Example 1. 25 ul of the thawed blood samples were fixed in paraformaldehyde (PFA), then antibody staining was performed by using specific monoclonal antibodies recognizing human ABCG2. Labeled samples were transferred into 96 well microplates and fluorescence values were determined in a VICTOR fluorescence microplate reader.

In parallel, genomic DNA was isolated from the blood samples and common SNPs in ABCG2 were detected by quantitative PCR, while mutations were determined by direct sequencing (for detailed Methods see Example 1).

A cellular ELISA system by using unlabeled primary antibodies (BXP34, BXP21, 5D3) and peroxidase (HRP)-conjugated as well as alkaline phosphatase (AP) conjugated secondary antibodies, available from commercial sources is under current development. In order to avoid repeated centrifugation, we use multiwell plates coated with polylisine, which allows the permanent attachment of the red cell membranes to the plates. The reduction of the background staining and a reference staining with HRP or PA conjugated Glycophorin-A is currently developed to obtain standardized, quantitative red cell membrane expression levels in a microplate assay.

Results and Discussion

The pre-labeled red cell membrane preparations, when transferred into microtiter plates, provided well measurable fluorescence (FIG. 9). All three anti-ABCG2 antibodies, recognizing either intracellular (BXP34 and BXP21) or extracellular epitopes (5D3) provided appropriate binding levels in the plate reader, corresponding to the FACS data. All three anti-ABCG2 antibodies gave a clear recognition of the ABCG2 protein, well separable from the control IgG background.

With this method we have also determined antibody recognition of the ABCG2 protein in blood samples individuals carrying the heterozygous mutations causing premature termination of the ABCG2 gene, and found a significantly lower level of ABCG2 expression. A further validation and improvement of this microplate methodology is currently under progress.

As a summary, we document that erythrocyte membrane expression level of the ABCG2 multidrug transporter can be properly detected in microplate assays. This extended method for a quantitative determination of the ABCG2 protein, responsible for ADME-Tox properties and drug sensitivity, should significantly promote a personalized approach in pharmacology.

Example 4

Flow Cytometry Based Quantitative Determination of the ABCB6 Erythrocyte Membrane Protein in Freshly Drawn Peripheral Blood Erythrocyte Membranes by Using a Monoclonal Antibody—Correlation with Polymorphic Variants and Mutations Similarly to our previous experiments using a flow cytometry assay to quantitate ABCG2 expression in the erythrocyte membrane, we have determined the ABCB6 protein levels in red blood cells.

Methods

For the membrane protein assays in flow cytometry, peripheral venous or capillary blood samples of healthy volunteers were used. 25 ul of the blood samples were diluted and fixed in 4 mL of phosphate buffered saline (PBS) containing 0.5% bovine serum albumin (BSA), then antibody staining was performed by using the OSK43 specific monoclonal antibody, recognizing the human ABCB6 protein.

Genetic Analysis:

For ABCB6 polymorphism and mutation studies genomic DNA was isolated from EDTA anticoagulated peripheral blood by Gentra Purege Blood Kit (Quiagen, Hamburg, Germany). Sanger sequencing of the ABCB6 coding region and exon-intron boundaries (exons 1-19) was performed by Applied Biosystems 310 Genetic Analyzer (Life Technologies, Carlsbad, USA).

Results and Discussion

We have quantified the expression of erythrocyte ABCB6 in 47 unrelated, healthy individuals. Similar ABCB6 levels were detected in the red blood cells of most individuals (9.46±1.45). However, we found three individuals showing much lower (about 60%) erythrocyte ABCB6 expression (5.26±0.99) (FIG. 13B). Sequencing of the entire ABCB6 gene revealed that these individuals carry heterozygous mutations in this gene.

In order to investigate if a direct relationship exists between the mutations and the erythrocyte ABCB6 expression levels (as detected in case of ABCG2), we obtained blood samples from the family members of the donors carrying the ABCB6 mutations. As shown in FIG. 2, we found a co-segregation of the reduced erythrocyte ABCB6 expression levels and the mutations, and detected about 75% reduction in the subject carrying mutations in both alleles of the ABCB6 gene.

Example 5

Quantitative Determination of the ABCA1, ABCB1 (MDR1), ABCC1 (MRP1), ABCC3 (MRP3) and ABCC4 (MRP4) Membrane Proteins in the Human Erythrocyte Membrane by Using Monoclonal Antibodies. Use of Freshly Drawn Venous or Capillary Blood for Performing Quantitative Assays The ABCB1, ABCC1, and ABCC4 proteins have been reported to be present in the erythrocyte membrane [Pasini E M et al., Blood. 2006(108):791-801; Alexandre B M et al., Expert Rev Proteomics. 2010(7):165-168; de Wolf C J et al., Febs J. 2007(274):439-450; Leimanis M L et al., Biochem Biophys Res Commun. 2007(354):345-350. http://www.ncbi.nlm.nih.gov/projects/gv/rbc/xslcgi.fcgi?cmd=bgmut/systems)].

In Example 1 we have worked out a quantitative assay for the determination of the red cell membrane ABCG2 protein expression and documented a correlation of ABCG2 transporter expression with genetic variations. In the present Example we examined if a similar quantitative determination of the erythrocyte membrane ABC protein expression can be performed for the above specific ABC transporter proteins. Previously ABCA1 and ABCC3 were not shown to be present in the red cell membrane and we explored if these proteins may also be detected by sensitive antibody binding assays in the erythrocytes.

Methods

For the membrane protein assays in flow cytometry, peripheral venous or capillary blood samples of healthy volunteers were used. 25 ul of the blood samples were fixed in paraformaldehyde (PFA), then antibody staining was performed by using specific monoclonal antibodies recognizing human ABC transporters. In preliminary experiments we determined that in some cases a maximum mAb binding could be obtained if 0.1% saponin was added to the samples during antibody binding. We have also examined the potential use of frozen-thawed blood samples for quantitative determination of these membrane proteins.

Similarly to our previous experiments using a flow cytometry assay to quantitate ABCG2 expression in the erythrocyte membrane, we have used ABC protein-specific monoclonal antibodies.

Results and Discussion

1. When examining the presence of ABCB1/MDR1 in the human red cell membrane, we used two ABCB1 specific monoclonal antibodies (MRK16 and UIC2), reacting with a cell-surface epitope of human ABCB1. Since these antibodies were reported to interact with complex epitopes and this interaction greatly depend on the conformation or fixation of the membrane protein we used both freshly drawn and frozen and thawed blood cells, fixed in 0.1% PFA, and in some cases permeabilized with 1% saponin (FIGS. 10 to 12).

2. ABCC1 was detected in human red cells by two monoclonal antibodies (M6, a mouse monoclonal antibody, and R1, a rat monoclonal antibody) reacting with intracellular epitopes of the human ABCC1 protein. Cells were obtained from freshly drawn blood, membranes were not fixed in this experiment (FIG. 14).

3. ABCC4 was detected in human red cells by a mouse monoclonal antibody (M4-1-10) reacting with an intracellular epitope of the human ABCC4 protein. Blood cells were freshly drawn and the membranes were not fixed (FIG. 15).

Figure 16A:
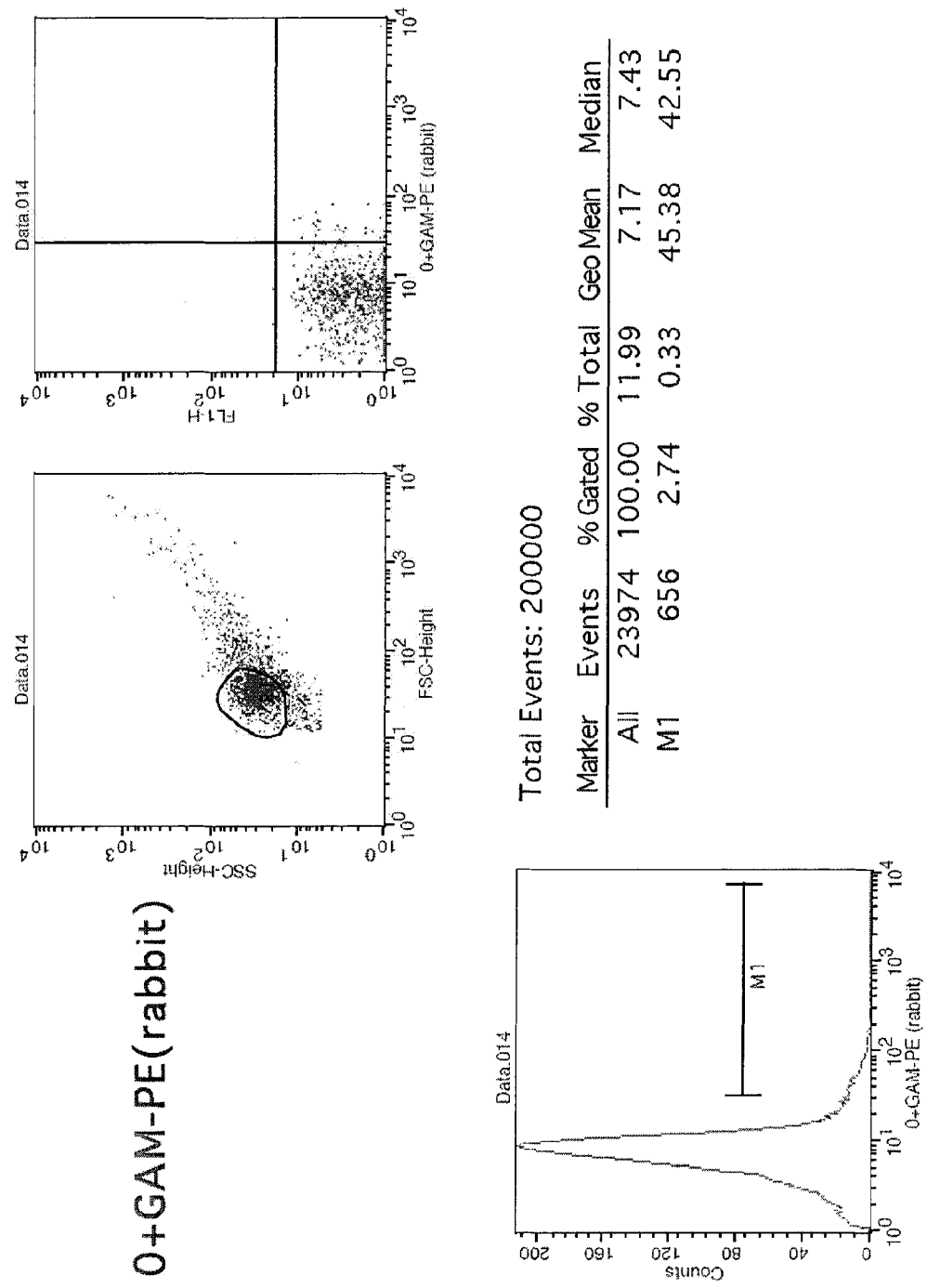
Figure 16B:
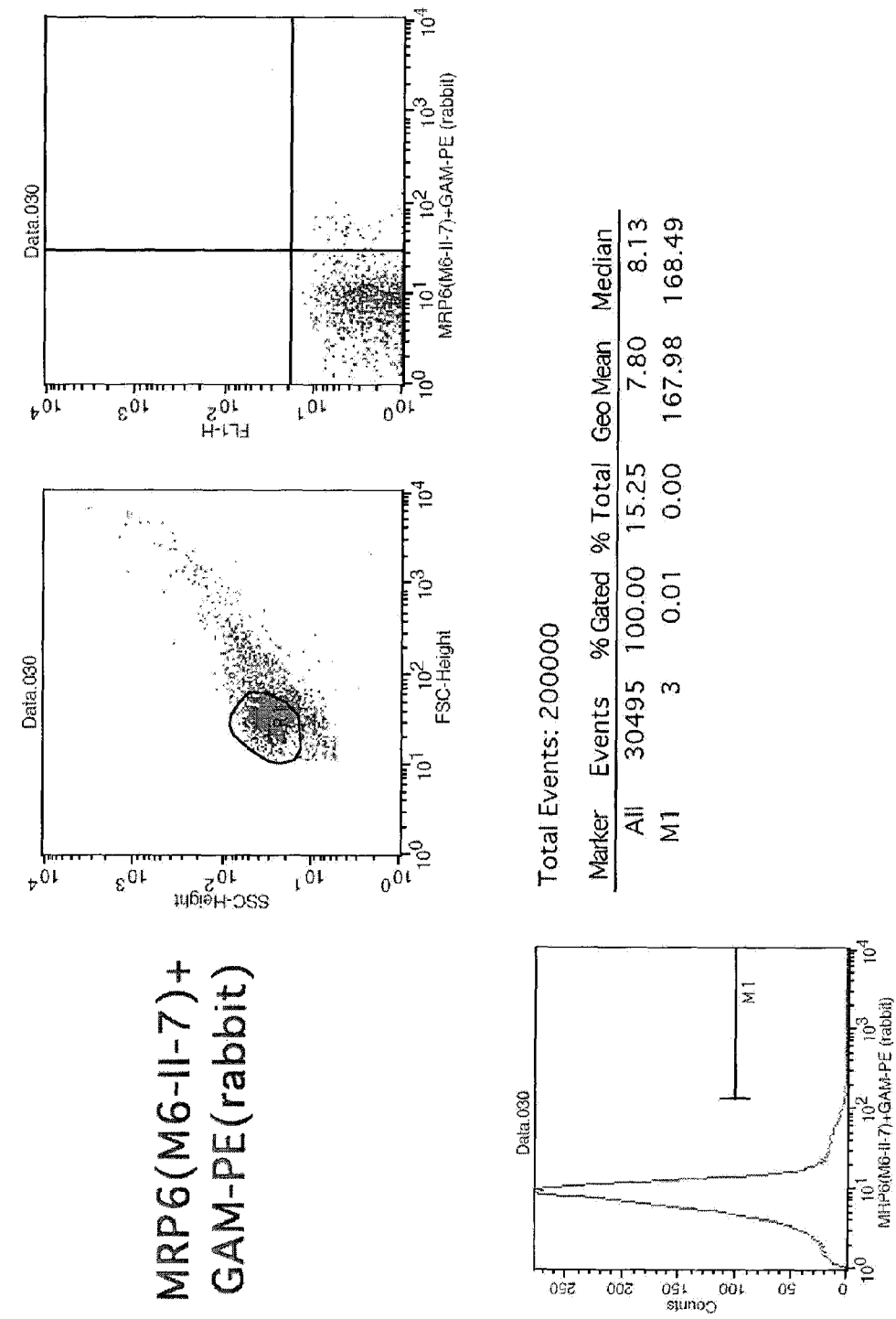
Figure 16C:
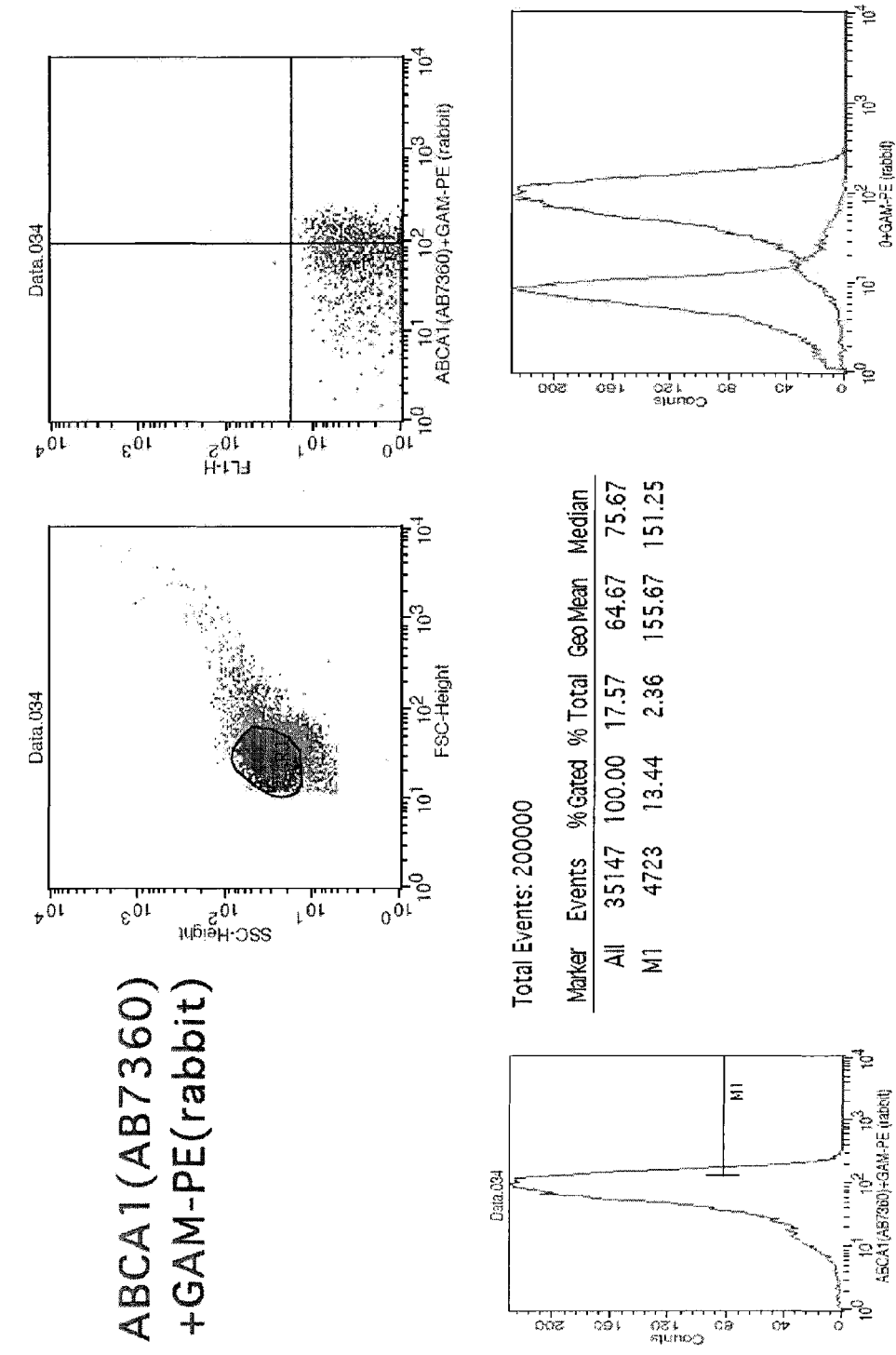
Figure 16D:
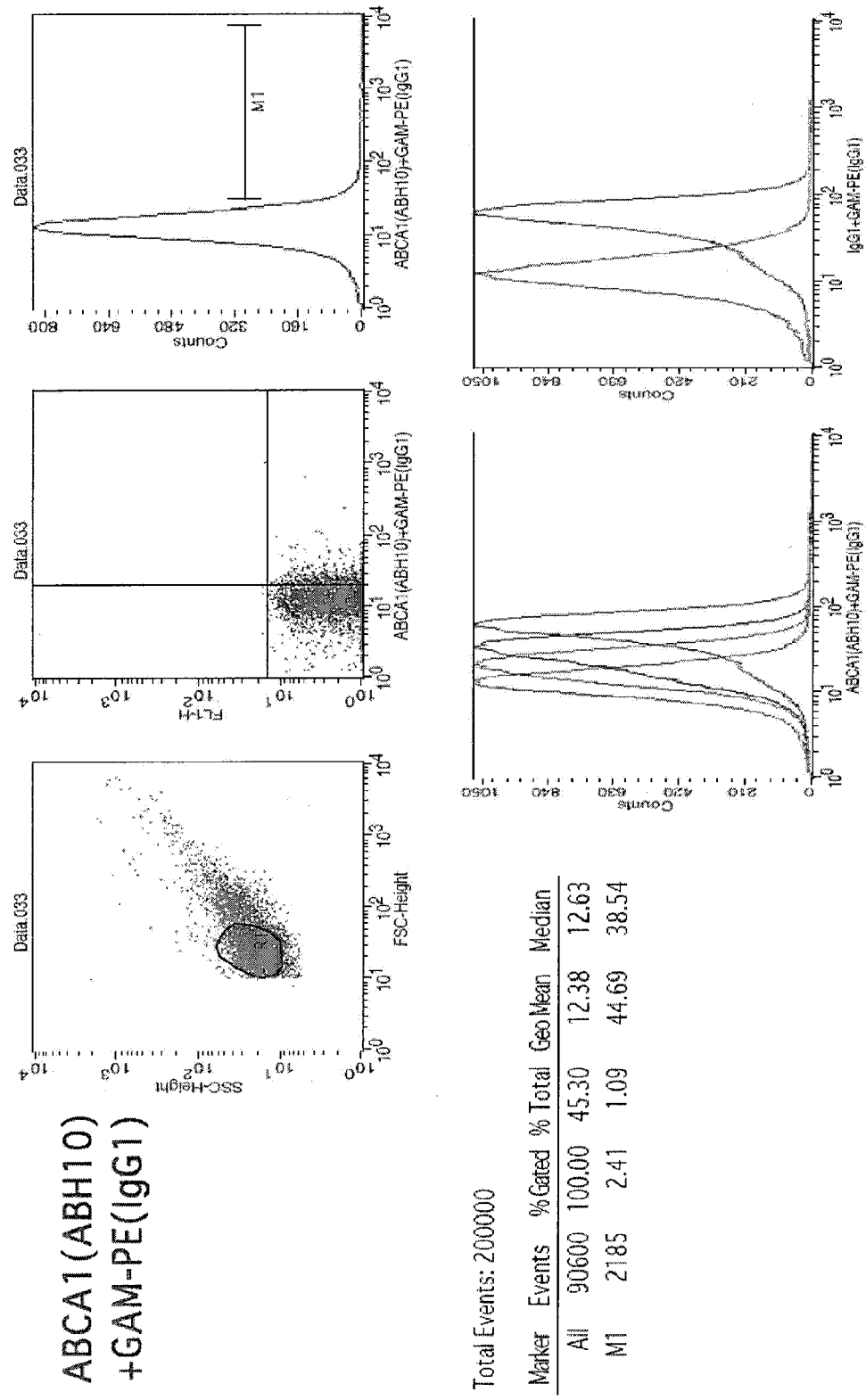

4. ABCA1 was measured in human red cells by two monoclonal antibodies (FIG. 16, Panel A: AB7360, a rabbit plyclonal antibody, and Panel B: ABH10, a mouse monoclonal antibody) reacting with intracellular epitopes of the human ABCA1 protein. Blood cells were freshly drawn and the membranes were not fixed (FIG. 16). As a control, the lack of ABCC6 protein in the red cell membrane is indicated by using the M6-II-7, ABCC6-specific monoclonal antibody. To obtain saturation binding, the ABH10 antibody was used to titrate the binding sites (FIG. 16B).

5. ABCC3 was measured in human red cells by a monoclonal antibody M3-II-9, reacting with an intracellular epitope of the human ABCC3 protein. Blood cells were freshly drawn and fixed in 1% PFA, To obtain saturation binding, the M3-II-9, antibody was used to titrate the binding sites (FIG. 17).

Example 6

Quantitative Determination of a Characteristic Intracellular and Extracellular Membrane Proteins in the Human Erythrocyte Membrane. Quantitative Determination of Erythrocyte Membrane Actin by a Specific Natural Ligand, Phalloidin Labeling. Determination of the Plasma Membrane Wheat Germ Agglutinin Binding Proteins in the Human Erythrocyte Membrane by Using Fluorescent Wheat-Germ Agglutinin Preparations Methods For the membrane protein assays in flow cytometry, peripheral venous or capillary blood samples of healthy volunteers were used. 25 ul of the blood samples were fixed in paraformaldehyde (PFA), then fluorescent ligand staining was performed by using TRITC-labeled phalloidin for actin, or Alexa 647 labeled WGA for lectin-binding proteins. We have also examined the potential use of frozen-thawed blood samples for quantitative determination of these membrane proteins.

Results and Discussion

Membrane bound actin was detected in human red cells by TRITC-Phalloidin binding. Freshly drawn human blood cells were fixed in 1% PFA. Specific labeling only in the ghost fraction (Panel A) was detected, addition of saponin (Panel C) did not alter phalloidin binding. Saturation of phalloidin binding was observed already at the addition of low amounts (0.125 uL) of labeled phalloidin (FIG. 18).

In a further experiment extracellular WGA binding proteins were measured in human red cells. Freshly drawn human blood cells were fixed in 1% PFA. Specific WGA labeling was obtained both in the ghost fraction (FIG. 19A), and the intact red cell fraction (FIG. 19B), saponin did not alter WGA binding (not shown). A saturation of WGA binding was achieved only by the addition of high amounts (over 0.25 uL) of labeled WGA.

Example 7

Flow Cytometry Based Quantitative Determination of the Plasma Membrane Calcium ATPase (PMCA) Membrane Transporter and its Isoforms in the Human Erythrocyte Membrane The plasma membrane CaATPases (PMCA1-4, or ATP2B1-4) play an important role in keeping the intracellular calcium concentration at a low level. The human red cells contain preferentially two isoforms of the pump namely ATP2B1-PMCA1, ATP2B4-PMCA4.

Three PMCA isoforms, PMCA1-4, occur in varying distributions in the tissues, the PMCA1 is ubiquitous in all humans tissues. Improperly functioning PMCA proteins have been found associated with human conditions such as impaired hearing or balance, brain disfuntions and infertility [see Carafoli, E *Physiological Reviews* 71 (1): 129-153. (1991); Strehler, E E and Zacharias D A, *Physiological Reviews* 81 (1): 21-50. (2001); Holton, M L et al. World J Biol Chem. 2010 June 26; 1(6): 201-208]. Changes in PMCA expression are associated with other diseases including cataract formation, carciniogenesis, diabetes, and cardiac hypertension and hypertrophy. Severity of these diseases may be affected by subtle changes in expression of the PMCA isoforms expressed in those tissues [Tempel B L and Shilling D J. Subcell Biochem. (2007); 45:365-83. Brini M. Pflugers Arch. 2009, 457(3):657-64.]. The PMCA4 isoform seems to have a special importance in sperm maturation and the lack of this protein causes male infertility [Brandenburger T, et al., J Biol Chem. (2011) Mar. 11; 286(10):7938-46. Epub 2010 Dec. 27.].

Determination of the PMCA protein, which is expected to be relatively constant, may help to quantitate the calcium transporter at a general, individual level. In addition, the application of isoform-specific monoclonal antibodies allows a direct determination of the PMCA isoforms in the erythrocytes. Quantitaive determination of the general level of the PMCA proteins and especially the PMCA4 isoform in the human erythrocytes should be applicable for diagnostic purposes.

Methods

For the membrane protein assays in flow cytometry, peripheral venous or capillary blood samples of healthy volunteers were used. 25 ul of the blood samples were fixed in paraformaldehyde (PFA), then antibody staining was performed by using specific monoclonal antibodies recognizing human PMCA transporters. In preliminary experiments we determined that in some cases a maximum mAb binding could be obtained if 0.1% saponin was added to the samples during antibody binding. We have also examined the potential use of frozen-thawed blood samples for quantitative determination of the PMCA proteins. Similarly to our previous experiments using a flow cytometry assay to quantitate ABCG2 expression in the erythrocyte membrane (see Example 1), we have used PMCA protein-specific monoclonal antibodies.

Results and Discussion

A. Determination of the ATP2B-PMCA Proteins by the 5F10 Monoclonal Antibody.

The 5F10 monoclonal antibody recognizes all PMCA isoforms [Caride A J et al. *Biochem J.* (1996) 316 (Pt 1)):353-359.] It has a linear intracellular epitope for PMCA interaction which can be strongly reduced by the addition of a specific peptide, mimicking the epitope [Caride A J et al., (1996), see above].

In the experiments we have used the erythrocyte fixation method described in the methods section and performed FACS studies for quantitative PMCA determination. We found that PMCA staining was obtained in the ghost fraction (FIG. 20), low concentrations of 5F10 provided saturation and maximum labeling (FIG. 21), and saponin permeabilization had no major effect on the quantitative staining results (FIG. 22). In experiments not documented here, we also found that the specific epitope peptide strongly inhibited 5F10 labeling in the red cell membranes. In order to obtain saturating labeling with the 5F10 antibody the calibration of antibody binding was performed and maximum labeling conditions were used to quantitate PMCA expression levels.

B. Determination of the ATP2B4-PMCA4 Protein by the JA9 Monoclonal Antibody.

The JA9 monoclonal antibody selectively recognizes the PMCA4, which is the most abundant PMCA isoform in the human red cell membrane [Caride et al, (1996)]. It has a linear intracellular epitope for PMCA interaction which can be strongly reduced by the addition of a specific peptide, mimicking the epitope [Caride A J et al., (1996), see above].

In the experiments we have used the erythrocyte fixation method described in the methods section and performed FACS studies for quantitative PMCA determination. We found that PMCA4 staining was obtained in the ghost fraction, JA9 provided saturation and maximum labeling (FIG. 23), and saponin permabilization increased the quantitative staining results (FIG. 24).

C. Determination of the ATP2B4b-PMCA4b Protein by the JA3 Monoclonal Antibody.

The JA3 monoclonal antibody selectively recognizes the PMCA4b isoform, which is the most abundant PMCA isoform in the human red cell membrane [Caride et al, (1996)]. It has a linear intracellular epitope for PMCA4b interaction which can be strongly reduced by the addition of a specific peptide, mimicking the epitope [Caride et al, (1996)].

In the experiments we have used the erythrocyte fixation method described in the methods section and performed FACS studies for quantitative PMCA4b determination. We found that PMCA4b staining was obtained in the ghost fraction, JA3 provided saturation and maximum labeling (FIG. 25). In order to obtain saturating labeling with the JA3 monoclonal antibody, the calibration of antibody binding was performed and maximum labeling conditions were used to quantitate PMCA4b isoform expression levels.

Example 8

Flow Cytometry Based Quantitative Parallel Determination of the ABCG2 (BCRP, MXR) and the ABCB1 (MDR1) Membrane Proteins in Freshly Drawn Peripheral Blood Erythrocyte Membranes by Using Selective Monoclonal Antibodies—Inverse Correlation of the Expression of the Two ABC Transporters Methods For details see Examples 1 and 3. Anticoagulated blood samples were fixed in paraformaldehyde (PFA), stained with monoclonal antibodies recognizing human ABCG2 or ABCB1, and subjected to flow cytometry (FACS). Intact red cells and erythrocyte ghost were gated out based on the forward scatter (FSC) and side scatter (SSC) parameters. Both fractions were analyzed for antibody staining by a FACSCalibur flow cytometer (excitation wavelength: 488 nm (Argon ion laser) emission filters: 585/42 nm for PE, 530/30 for FITC).

Results and Discussion

When we examined ABCG2 and ABCB1 expression in the same blood samples, we found that individuals with a low level of ABCG2 expression expressed higher levels of the ABCB1 protein. This was especially significant in the family members examined in Example 1, carrying heterozygous stop mutations of ABCG2. As shown in FIG. 26, family members with low ABCG2 levels had similar Glycophorin A expression levels (see Example 6), but the expression of ABCG2 and ABCB1 showed a practically inverse correlations. Detailed studies regarding this phenomenon, probably based on the up-regulation of ABCB1 expression in individuals with low ABCG2 expression levels, are currently underway in our laboratory.

Example 9

Reference Example

Western Blot Experiments

A. In order to document the expression of ABCG2 in the red cell membrane and compare the expression levels to those in known expression systems, we have performed numerous Western blot experiments by using isolated red cell membranes, isolated Sf9 insect cell membranes expressing the human ABCG2 protein, and A431 cells overexpressing ABCG2 [Özvegy C. et al., (2002), Telbisz A. et al., (2007)] As shown in FIG. 27, in accordance with previous data in the literature [Leimanis M. L., (2007), Saison C. et al., (2012)], we detected both the monomeric and dimeric forms of ABCG2 in the red cell membrane preparations. Based on several similar blots and comparing expression in the Sf9 membranes (corresponding to about 4% of total membrane proteins), and expression in the red cell membranes, we calculated an expression between 1-2,000 copies of ABCG2 in normal human erythrocytes.

B. In order to compare the relative expression of ABCG2 in the various donor red cells we performed Western blot experiments by using intact red cells from donors with a heterozygous stop mutation, compared to wild-type donors.

We compared the expression levels of the ABCG2 protein in intact red cells to that in isolated membranes of Sf9 cells expressing the human ABCG2 protein (FIG. 28, lane 1), K562 human erythroleukemia cells (lane 3, control) and K562 cells expressing ABCG2 based on lentiviral transduction (lane 2, K562-ABCG2). Total red cell preparations (15 µl of blood) were dissolved in 85 µl special disaggregation buffer, containing SDS and urea. Samples were applied from freshly drown blood of a donor homozygous for wt ABCG2 (lane 4), and of a donor heterozygous for an ABCG2 stop mutation (lane 5).

Note: When using an SDS+urea disaggreagation buffer and fresh red cells, only the monomeric form of ABCG2 is detected. The ABCG2 protein expressed in Sf9 cells is under-glycosylated, a high level glycosylation is observed in the K562 cells, while an intermediate level of glycosylation is seen in the red blood cells.

As documented, the ABCG2 bands are well visible, but there is no appreciable difference in the ABCG2 bands of these individuals by this technology (as reinforced by several similar blotting experiments). These experiments clearly point that this technology, while laborious and time consuming, cannot be used to evaluate small differences in the expression levels between various blood samples.

Example 10

Reference Example

Analysis of Intra- and Inter-Assay Variations

A detailed analysis of the intra- and inter-assay variations obtained in this study (see Results) is presented in Table 2.

TABLE 2

Characteristics of the assay performances described by intra- and interassay coefficients of variation (CV %).

| | Intraassay CV % | Interassay CV % |
|---|---|---|
| 5D3 whole cell | 3.8% | 7.1% |
| 5D3 ghost | 7.8% | 17.9% |
| BXP21 | 6.2% | 16.6% |
| BXP34 | 11.2% | 12.4% |
| ABCG2 factor | 5.3% | 10.1% |

INDUSTRIAL APPLICABILITY

This invention offers diagnostic tool-kits for determining quantitative expression of plasma membrane proteins as biomarkers in the erythrocyte membrane. The invention includes simple, validated, quantitative assay platforms which can be made available in most diagnostic laboratories. The platforms involve the processing of small amount of blood samples used for quantitative erythrocyte membrane protein measurements using high affinity specific interactions, preferably antibody-based methods. From the same blood sample parallel DNA-based assays can validate the genetic background of the observed quantitative protein expression level. The platform allows performing personalized, quantitative tests for the direct expression level of a wide range of membrane proteins and connecting them to individual genetic variability, disease conditions, disease stages and complications, treatment protocols, pharmacological responses, or toxic side effects.

REFERENCES

Akasaka K, Kaburagi T, Yasuda S, et al. Impact of functional ABCG2 polymorphisms on the adverse effects of gefitinib in Japanese patients with non-small-cell lung cancer. Cancer Chemother Pharmacol. (2010) (66):691-698.

Alexandre, B. M. Proteomic mining of the red blood cell: focus on the membrane proteome. Expert Rev Proteomics (2010) 7(2): 165-8.

Allen J D, Schinkel A H. Multidrug resistance and pharmacological protection mediated by the breast cancer resistance protein (BCRP/ABCG2) Mol Cancer Ther. (2002) (1):427-434.

Antonelou M. H. et al. Apolipoprotein J/Clusterin Is a Novel Structural Component of Human Erythrocytes and a Biomarker of Cellular Stress and Senescence PLoS ONE, (2011) 6(10) e26032 1-9

Blumenfeld O O, Patnaik S K. Allelic genes of blood group antigens: a source of human mutations and cSNPs documented in the Blood Group Antigen Gene Mutation Database. Human Mutation. (2004) January; 23(1):8-16.

Brandenburger T, Strehler E E, Filoteo A G, Caride A J, Aumüller G, Post H, Schwarz A, Wilhelm B. Switch of PMCA4 splice variants in bovine epididymis results in altered isoform expression during functional sperm maturation. J Biol Chem. (2011) Mar. 11; 286(10):7938-46. Epub (2010) Dec. 27.

Brini M. Plasma membrane Ca(2+)-ATPase: from a housekeeping function to a versatile signaling role. Pflugers Arch. (2009), 457(3):657-64.

Brozik, A., C. Hegedus, et al. Tyrosine kinase inhibitors as modulators of ATP binding cassette multidrug transporters: substrates, chemosensitizers or inducers of acquired multidrug resistance? Expert Opin Drug Metab Toxicol (2011) 7(5): 623-42.

Buchwalow I. B. and Böcker W., Immunohistochemistry: Basics and Methods Springer (2010)

Carafoli, E Calcium pump of the plasma membrane. Physiological Reviews (1991) 71 (1): 129-153.

Caride A J, Filoteo A G, Enyedi A, Verma A K, Penniston J T. Detection of isoform 4 of the plasma membrane calcium pump in human tissues by using isoform-specific monoclonal antibodies. Biochem J. (1996) May 15; 316 (Pt 1):353-9.

Cartron, J. P. and C. Rahuel. Human erythrocyte glycophorins: protein and gene structure analyses. Transfus Med Rev (1992) 6(2): 63-92.

Cusatis, G., V. Gregorc, et al. Pharmacogenetics of ABCG2 and adverse reactions to gefitinib. J Natl Cancer Inst (2006) 98(23): 1739-42.

de Wolf C J, Yamaguchi H, van der Heijden I, et al. cGMP transport by vesicles from human and mouse erythrocytes. Febs J. (2007) (274):439-450.

Deak B, et al., Diabetes and erythrocyte Na—Li exchanger, Acta Diabetol (2003) 40:9-13).

Diestra J E, Scheffer G L, Catala I, et al. Frequent expression of the multi-drug resistance-associated protein BCRP/MXR/ABCP/ABCG2 in human tumours detected by the BXP-21 monoclonal antibody in paraffin-embedded material. J Pathol. (2002) (198):213-219.

Doyle, L. A., W. Yang, et al. A multidrug resistance transporter from human MCF-7 breast cancer cells. Proc Natl Acad Sci USA (1998) 95(26): 15665-70.

Fischer, S., P. L. Lakatos, et al. ATP-binding cassette transporter ABCG2 (BCRP) and ABCB1 (MDR1) variants are not associated with disease susceptibility, disease phenotype response to medical therapy or need for surgeryin Hungarian patients with inflammatory bowel diseases. Scand J Gastroenterol (2007) 42(6): 726-33.

Furukawa T, Wakabayashi K, Tamura A, et al. Major SNP (Q141K) variant of human ABC transporter ABCG2 undergoes lysosomal and proteasomal degradations. Pharm Res. (2009) (26):469-479.

Gardner E R, Burger H, van Schaik R H, et al. Association of enzyme and transporter genotypes with the pharmacokinetics of imatinib. Clin Pharmacol Ther. (2006) (80): 192-201.

Glavinas, H., P. Krajcsi, et al. The role of ABC transporters in drug resistance, metabolism and toxicity. Curr Drug Deliv (2004) 1(1): 27-42.

Goodman, S. R., A. Kurdia, et al. The human red blood cell proteome and interactome. Exp Biol Med (Maywood) (2007) 232(11): 1391-408.

Hernández-Hernández A et al., Alterations in erythrocyte membrane protein composition in advanced non-small cell lung cancer Blood Cells Mol Dis. (2006) 36(3):355-63

Honjo, Y., K. Morisaki, et al. Single-nucleotide polymorphism (SNP) analysis in the ABC half-transporter ABCG2 (MXR/BCRP/ABCP1). Cancer Biol Ther (2002) 1(6): 696-702.

Ichida K. et al, Nature Communications, Apr. 3, 2012, DOI: 10.1038/ncomms1756

Imai, Y., M. Nakane, et al. C421A polymorphism in the human breast cancer resistance protein gene is associated with low expression of Q141K protein and low-level drug resistance. Mol Cancer Ther (2002) 1(8): 611-6.

Itoda, M., Y. Saito, et al. Eight novel single nucleotide polymorphisms in ABCG2/BCRP in Japanese cancer patients administered irinotacan. Drug Metab Pharmacokinet (2003) 18(3): 212-7.

Jonker, J. W., M. Buitelaar, et al. The breast cancer resistance protein protects against a major chlorophyll-derived dietary phototoxin and protoporphyria. Proc Natl Acad Sci USA (2002) 99(24): 15649-54.

Kast, H. R., B. Goodwin, et al. Regulation of multidrug resistance-associated protein 2 (ABCC2) by the nuclear receptors pregnane X receptor, farnesoid X-activated receptor, and constitutive androstane receptor. J Biol Chem (2002) 277(4): 2908-15.

Kobayashi D, Ieiri I, Hirota T, et al. Functional assessment of ABCG2 (BCRP) gene polymorphisms to protein expression in human placenta. Drug Metab Dispos. (2005) (33):94-101.

Kondo, C., H. Suzuki, et al. Functional analysis of SNPs variants of BCRP/ABCG2. Pharm Res (2004) 21(10): 1895-903.

Koren W, et al., Enhanced erythrocyte Na+/H+ exchange predicts diabetic nephropathy in patients with IDDM. Diabetologia. (1998) February; 41(2):201-5;

Krishnamurthy P, Schuetz J D. Role of ABCG2/BCRP in biology and medicine. Annu Rev Pharmacol Toxicol. (2006) (46):381-410.

Leimanis M L, Georges E. ABCG2 membrane transporter in mature human erythrocytes is exclusively homodimer. Biochem Biophys Res Commun. (2007) (354):345-350.

Li, J. et al. Association of variant ABCG2 and the pharmacokinetics of epidermal growth factor receptor tyrosine kinase inhibitors in cancer patients. Cancer Biol Ther (2007) 6(3): 432-8.

Maliepaard M, Scheffer G L, Faneyte I F, et al. Subcellular localization and distribution of the breast cancer resistance protein transporter in normal human tissues. Cancer Res. (2001) (61):3458-3464.

Mary Louisa Holton, Weiguang Wang, Michael Emerson, Ludwig Neyses and Angel L Armesilla. Plasma membrane calcium ATPase proteins as novel regulators of signal transduction pathways. World J Biol Chem. (2010) June 26; 1(6): 201-208.

Matsuo H, Takada T, Ichida K, et al. Common defects of ABCG2, a high-capacity urate exporter, cause gout: a function-based genetic analysis in a Japanese population. Sci Transl Med. (2009) (1):5ra11.

Miyake, K., L. Mickley, et al. Molecular cloning of cDNAs which are highly overexpressed in mitoxantrone-resistant cells: demonstration of homology to ABC transport genes. Cancer Res (1999) 59(1): 8-13.

Mizuarai, S., N. Aozasa, et al. Single nucleotide polymorphisms result in impaired membrane localization and reduced atpase activity in multidrug transporter ABCG2. Int J Cancer (2004) 109(2): 238-46.

Morisaki K, Robey R W, Ozvegy-Laczka C, et al. Single nucleotide polymorphisms modify the transporter activity of ABCG2. Cancer Chemother Pharmacol. (2005) (56): 161-172.

Nakanishi, T., K. Shiozawa, et al. Complex interaction of BCRP/ABCG2 and imatinib in BCR-ABL-expressing cells: BCRP-mediated resistance to imatinib is attenuated by imatinib-induced reduction of BCRP expression. Blood (2006) 108(2): 678-84.

Oliver, Constance; Jamur, Maria Célia, Immunocytochemical Methods and Protocols Series: Methods in Molecular Biology, Springer, Vol. 588, (2009)

Ozvegy C, Varadi A, Sarkadi B. Characterization of drug transport, ATP hydrolysis, and nucleotide trapping by the human ABCG2 multidrug transporter. Modulation of substrate specificity by a point mutation. J Biol Chem. (2002) 277:47980-47990.

Ozvegy-Laczka C, Laczko R, Hegedus C, et al. Interaction with the 5D3 monoclonal antibody is regulated by intramolecular rearrangements but not by covalent dimer formation of the human ABCG2 multidrug transporter. J Biol Chem. (2008) (283):26059-26070.

Ozvegy-Laczka, C., G. Varady, et al. Function-dependent conformational changes of the ABCG2 multidrug transporter modify its interaction with a monoclonal antibody on the cell surface. J Biol Chem (2005) 280(6): 4219-27.

Ozvegy-Laczka, C., R. Laczko, et al. Interaction with the 5D3 monoclonal antibody is regulated by intramolecular rearrangements but not by covalent dimer formation of the human ABCG2 multidrug transporter. J Biol Chem (2008) 283(38): 26059-70.

Pasini E M, Kirkegaard M, Mortensen P, Lutz H U, Thomas A W, Mann M. In-depth analysis of the membrane and cytosolic proteome of red blood cells. Blood. (2006) (108):791-801.

Pasini, E. M., H. U. Lutz, et al. Red blood cell (RBC) membrane proteomics—Part I: Proteomics and RBC physiology. J Proteomics (2010) 73(3): 403-20.

Phipps-Green, A. J., J. E. Hollis-Moffatt, et al. A strong role for the ABCG2 gene in susceptibility to gout in New Zealand Pacific Island and Caucasian, but not Maori, case and control sample sets. Hum Mol Genet (2010) 19(24): 4813-9.

Poguntke, M., E. Hazai, et al. Drug transport by breast cancer resistance protein. Expert Opin Drug Metab Toxicol (2010) 6(11): 1363-84.

Renshaw, Simon Immunohistochemistry, Methods Express Series, Edited by, Scion Publishing Ltd. (2006).

Robey R W, Ierano C, Zhan Z, Bates S E. The challenge of exploiting ABCG2 in the clinic. Curr Pharm Biotechnol. (2011) (12):595-608.

Robey, R. W., O. Polgar, et al. ABCG2: determining its relevance in clinical drug resistance. Cancer Metastasis Rev (2007) 26(1): 39-57.

Robey, R. W., W. Y. Medina-Perez, et al. Overexpression of the ATP-binding cassette half-transporter, ABCG2 (Mxr/BCrp/ABCP1), in flavopiridol-resistant human breast cancer cells. Clin Cancer Res (2001) 7(1): 145-52.

Ross, D. D., J. E. Karp, et al. Expression of breast cancer resistance protein in blast cells from patients with acute leukemia. (2000) Blood 96(1): 365-8.

Saison C, Helias V, Ballif B A, et al. Null alleles of ABCG2 encoding the breast cancer resistance protein define the new blood group system Junior. Nat Genet. (2012) 44:174-177.

Sarkadi B, Homolya L, Szakacs G, Varadi A. Human multidrug resistance ABCB and ABCG transporters: participation in a chemoimmunity defense system. Physiol Rev. (2006) (86):1179-1236.

Sarkadi, B. and G. Szakacs Understanding transport through pharmacological barriers—are we there yet? Nat Rev Drug Discov (2010) 9(11): 897-8.

Sarkadi, B., C. Ozvegy-Laczka, et al. ABCG2—a transporter for all seasons. FEBS Lett (2004) 567(1): 116-20.

Scheffer G L, Maliepaard M, Pijnenborg A C, et al. Breast cancer resistance protein is localized at the plasma membrane in mitoxantrone- and topotecan-resistant cell lines. Cancer Res. (2000) (60):2589-2593.

Sparreboom A, Gelderblom H, Marsh S, et al. Diflomotecan pharmacokinetics in relation to ABCG2 421C>A genotype. Clin Pharmacol Ther. (2004) (76):38-44.

Sprague R. S. et al. Reduced Expressoin of Gi in Erythrocytes of Humans With Type 2 Diabetes Is Associated With Impairment of Both cAMP Generation and ATP Release Diabetes (2006) 55 3588-3593
Strehler, E E; Zacharias D A Role of alternative splicing in generating isoform diversity among plasma membrane calcium pumps. Physiological Reviews (2001) 81 (1): 21-50.
Szakacs G, Varadi A, Ozvegy-Laczka C, Sarkadi B. The role of ABC transporters in drug absorption, distribution, metabolism, excretion and toxicity (ADME-Tox). Drug Discov Today. (2008) (13):379-393.
Szatmari, I. et al. Peroxisome proliferator-activated receptor gamma-regulated ABCG2 expression confers cytoprotection to human dendritic cells. J Biol Chem (2006) 281 (33): 23812-23.
Tamura, A., Y. Onishi, et al. In vitro evaluation of photosensitivity risk related to genetic polymorphisms of human ABC transporter ABCG2 and inhibition by drugs. Drug Metab Pharmacokinet (2007) 22(6): 428-40.
Telbisz A, Muller M, Ozvegy-Laczka C, et al. Membrane cholesterol selectively modulates the activity of the human ABCG2 multidrug transporter. Biochim Biophys Acta. (2007) 1768:2698-2713.
Tempel B L, Shilling D J. The plasma membrane calcium ATPase and disease. Subcell Biochem. (2007) 45:365-83.
Vlaming, M. L., J. S. Lagas, et al. Physiological and pharmacological roles of ABCG2 (BCRP): recent findings in Abcg2 knockout mice. Adv Drug Deliv Rev (2009) 61(1): 14-25.
Weder A. B. et al. Erythrocyte Sodium-Lithium Countertransport and Blood Pressure, Hypertension (2003) 41:842-846,
Yang Q, Kottgen A, Dehghan A, et al. Multiple genetic loci influence serum urate levels and their relationship with gout and cardiovascular disease risk factors. Circ Cardiovasc Genet. (2010) (3):523-530.
Zelinski T, Coghlan G, Liu X Q, Reid M E. ABCG2 null alleles define the Jr(a−) blood group phenotype. Nat Genet. (2012) 44:131-132.
Zhou, S., J. D. Schuetz, et al. The ABC transporter Bcrp1/ABCG2 is expressed in a wide variety of stem cells and is a molecular determinant of the side-population phenotype. Nat Med (2001) 7(9): 1028-34.
Zhou, S., J. J. Morris, et al. Bcrp1 gene expression is required for normal numbers of side population stem cells in mice, and confers relative protection to mitoxantrone in hematopoietic cells in vivo. Proc Natl Acad Sci USA (2002) 99(19): 12339-44.
Zhou, S., Y. Zong, et al. Increased expression of the Abcg2 transporter during erythroid maturation plays a role in decreasing cellular protoporphyrin IX levels. Blood (2005) 105(6): 2571-6.

The invention claimed is:

1. A method for assessing a condition related to expression of a cell membrane protein (CMP) of interest in a subject by quantitative measurement of the expression level of said CMP of interest in erythrocyte membranes of said subject, wherein the normal membrane expression range of said CMP of interest in the erythrocyte membrane is predetermined or known and wherein the condition in said subject is related to altered expression of said CMP of interest in a tissue other than erythrocytes in said subject,
said method comprising the steps of
providing a blood sample taken from said subject, said blood sample comprising erythrocytes,
preparing an erythrocyte test sample from the blood sample, wherein one or more epitope(s) of said CMP of interest present in the erythrocyte membrane is/are made available to a first CMP binding agent capable of specifically binding to said one or more epitope(s) and wherein the erythrocytes are whole cells including intact erythrocyte fraction and ghost erythrocyte fraction,
adding the first CMP binding agent to the test sample under conditions wherein said first CMP binding agent is specifically bound to said one or more epitope(s) of the CMP of interest present in the erythrocyte membrane in a saturating amount,
wherein either the first CMP binding agent is capable of binding to the intracellular portion of the CMP of interest of an erythrocyte ghost, or a second control CMP binding agent capable of binding to the intracellular portion of a control CMP of an erythrocyte ghost is also added to the test sample, or both, and wherein the membrane of at least a part of the erythrocytes is permeabilized to obtain erythrocyte ghosts and to allow intracellular binding of the first and/or second CMP binding agent,
obtaining signal elicited by the specific binding in a cellular detection experiment wherein the erythrocyte membranes are presented in the form of whole cells and wherein the first CMP binding agent is bound to said CMP of interest present in the erythrocyte membrane in the test sample, wherein
either one or both of (a) a signal elicited by the binding events in intact erythrocyte fraction and (b) a signal elicited by the binding events in erythrocyte ghost fraction is/are obtained,
converting the obtained signal into a value correlating with the amount of the molecules of said CMP of interest present in the membrane of said erythrocytes in each fraction, wherein said value is considered as the membrane expression level of said CMP of interest,
comparing the obtained membrane expression level of said CMP of interest in said subject with the normal membrane expression range of said CMP of interest in the erythrocyte membrane, and
a lack of difference from the normal membrane expression range is considered as indicative of a normal condition in the tissue other than erythrocytes in said subject,
a difference from the normal membrane expression range is considered as indicative of a condition different from normal in the tissue other than erythrocytes in said subject.

2. The method according to claim 1 wherein the CMP of interest is a membrane integrated protein, which is a cell membrane transporter protein (CMTP).

3. The method according to claim 2 wherein the condition related to expression of a CMP of interest in said subject is selected from the group consisting of genetic variations, genetic diseases, conditions due to a mutation in the gene of said CMP of interest, conditions due to up-regulation or down-regulation of the gene expression of said CMP of interest or conditions changing the specific membrane expression level of said CMP of interest, or different membrane expression levels due to different isoforms of said CMP of interest.

4. The method of claim 1 wherein the signal is obtained in a flow cytometry experiment and the number of cells comprising the CMP of interest in their membranes is assessed, or wherein the signal is obtained in an assay wherein parallel samples are handled in a plate format assay and the amount of signal is assessed.

5. The method of claim 1 wherein in the preparation of the erythrocyte test sample
   fixation is used and/or
   permeabilization is used wherein the membrane of at least a part of the erythrocytes is permeabilized to obtain erythrocyte ghosts and to allow intracellular binding of the first CMP binding agent and
   wherein both of (a) the signal elicited by the binding events in intact erythrocyte fraction and (b) a signal elicited by the binding events in erythrocyte ghost fraction are obtained.

6. The method of claim 1 wherein the steps of the method are repeated multiple times and thereby any alteration in the condition of said subject is monitored.

7. The method according to claim 1 wherein the normal membrane expression range of said CMP of interest in the erythrocyte membrane is determined by a method comprising the steps of
   providing blood samples comprising erythrocytes from a cohort or plurality of subjects in a population,
   preparing erythrocyte test samples from the blood samples wherein one or more epitope(s) of the CMP of interest present in the erythrocyte membrane is/are made available to a CMP binding agent capable of specifically binding to said one or more epitope(s) and wherein the erythrocytes are whole cells,
   adding the CMP binding agent to the test samples under conditions wherein said CMP binding agent is specifically bound to said one or more epitope(s) of the CMP of interest present in the erythrocyte membrane in a saturating amount,
   obtaining signal elicited by the specific binding in a cellular detection experiment wherein the erythrocyte membranes are presented in the form of whole cells and wherein the CMP binding agent is bound to the CMP of interest present in the erythrocyte membrane in the test samples,
   converting the obtained signal into a set of values correlating with the amount of the molecules of the CMP of interest present in the membrane of said erythrocytes, wherein said set of values are considered as a set of membrane expression levels of said CMP in the subjects,
   defining a normal membrane expression range indicative of a normal condition in the population of said subjects by analysing the set of membrane expression levels and, if desired, by comparing the membrane expression levels to subjects of normal condition and subjects of not normal condition identified in said cohort or plurality of subjects preferably by one or more independent method or experiment.

8. The method according to claim 1 wherein the CMP of interest is a membrane integrated protein selected from
   a cell membrane receptor,
   a cell membrane enzyme, or
   a cell membrane binding protein.

9. The method according to claim 1 wherein both a CMP binding agent capable of binding to the intracellular portion of the CMP of interest and a CMP binding agent capable of binding to the extracellular portion of the CMP of interest are applied.

10. The method of claim 4 wherein the signal is obtained in an immunosorbant assay.

11. The method of claim 1 wherein the first CMP binding agent is a monoclonal antibody.

12. The method according to claim 1 wherein the condition related to expression of a CMP of interest in said subject is selected from the group consisting of genetic variations, genetic diseases, conditions due to a mutation in the gene of said CMP of interest, conditions due to up-regulation or down-regulation of the gene expression of said CMP of interest or conditions changing the specific membrane expression level of said CMP of interest, or different membrane expression levels due to different isoforms of said CMP of interest.

* * * * *